(12) United States Patent
Grunwald et al.

(10) Patent No.: US 10,368,837 B2
(45) Date of Patent: Aug. 6, 2019

(54) APPARATUS AND METHOD FOR VASCULAR ACCESS

(71) Applicant: ARROW INTERNATIONAL, INC., Wayne, PA (US)

(72) Inventors: Sorin Grunwald, Palo Alto, CA (US); Fiona Maria Sander, Los Altos Hills, CA (US); Wilfred J. Samson, Saratoga, CA (US); Bradley Hill, Santa Clara, CA (US)

(73) Assignee: ARROW INTERNATIONAL, INC., Wayne, PA (US)

( * ) Notice: Subject to any disclaimer, the term of this patent is extended or adjusted under 35 U.S.C. 154(b) by 0 days.

(21) Appl. No.: 15/092,588

(22) Filed: Apr. 6, 2016

(65) Prior Publication Data

US 2016/0220226 A1    Aug. 4, 2016

Related U.S. Application Data

(60) Division of application No. 12/147,413, filed on Jun. 26, 2008, now abandoned, which is a
(Continued)

(51) Int. Cl.
*A61B 8/06* (2006.01)
*A61B 8/12* (2006.01)
(Continued)

(52) U.S. Cl.
CPC .............. *A61B 8/12* (2013.01); *A61B 5/06* (2013.01); *A61B 5/411* (2013.01); *A61B 7/00* (2013.01);
(Continued)

(58) Field of Classification Search
CPC ....................................... A61B 8/12
See application file for complete search history.

(56) References Cited

U.S. PATENT DOCUMENTS

| 3,565,062 A | 2/1971 | Kuris |
| 4,143,650 A | 3/1979 | Hatke |

(Continued)

FOREIGN PATENT DOCUMENTS

| CN | 2031655 U | 2/1989 |
| CN | 1628602 A | 6/2005 |

(Continued)

OTHER PUBLICATIONS

Benchimol et al.; Bidirectional blood flow velocity in the cardiac chambers and great vessels studied with the doppler ultrasonic flowmeter; The Amer. J. of Med.; vol. 52; pp. 467-473; 1972.
(Continued)

*Primary Examiner* — Rochelle D Turchen
(74) *Attorney, Agent, or Firm* — Baker & Hostetler LLP

(57) ABSTRACT

In an aspect, embodiments of the invention relate to the effective and accurate placement of intravascular devices such as central venous catheters, in particular such as peripherally inserted central catheters or PICC. One aspect of the present invention relates to vascular access. It describes devices and methods for imaging guided vascular access and more effective sterile packaging and handling of such devices. A second aspect of the present invention relates to the guidance, positioning and placement confirmation of intravascular devices without the help of X-ray imaging. A third aspect of the present invention relates to devices and methods for the skin securement of intravascular devices and post-placement verification of location of such devices. A forth aspect of the present invention relates to improvement of the workflow required for the placement of intravascular devices.

19 Claims, 31 Drawing Sheets

Device for single beam imaging guidance of Vascular Access

Related U.S. Application Data continuation-in-part of application No. 11/431,140, filed on May 8, 2006, now Pat. No. 9,204,819, and a continuation-in-part of application No. 11/431,118, filed on May 8, 2006, now Pat. No. 9,198,600, and a continuation-in-part of application No. 11/431,093, filed on May 8, 2006, now abandoned, and a continuation-in-part of application No. 11/430,511, filed on May 8, 2006, now Pat. No. 8,409,103.

(60) Provisional application No. 60/678,209, filed on May 6, 2005, provisional application No. 60/682,002, filed on May 18, 2005, provisional application No. 60/937,280, filed on Jun. 26, 2007.

(51) Int. Cl.
| | | |
|---|---|---|
| *A61B 5/06* | (2006.01) | |
| *A61B 5/00* | (2006.01) | |
| *A61B 7/00* | (2006.01) | |
| *A61B 8/08* | (2006.01) | |
| *A61B 8/00* | (2006.01) | |
| *G06Q 50/22* | (2018.01) | |
| *A61B 90/11* | (2016.01) | |
| *A61B 5/0402* | (2006.01) | |
| *A61B 5/1459* | (2006.01) | |
| *A61B 17/00* | (2006.01) | |
| *A61B 90/00* | (2016.01) | |
| *A61B 34/20* | (2016.01) | |

(52) U.S. Cl.
CPC .............. *A61B 8/06* (2013.01); *A61B 8/0841* (2013.01); *A61B 8/42* (2013.01); *A61B 8/445* (2013.01); *A61B 90/11* (2016.02); *G06Q 50/22* (2013.01); *A61B 5/0402* (2013.01); *A61B 5/1459* (2013.01); *A61B 8/461* (2013.01); *A61B 34/20* (2016.02); *A61B 2017/003* (2013.01); *A61B 2017/00106* (2013.01); *A61B 2090/378* (2016.02); *A61B 2090/3782* (2016.02); *A61B 2090/3929* (2016.02)

(56) References Cited

U.S. PATENT DOCUMENTS

| | | |
|---|---|---|
| 4,319,580 A | 3/1982 | Colley et al. |
| 4,324,258 A | 4/1982 | Huebscher et al. |
| 4,354,502 A | 10/1982 | Colley et al. |
| 4,362,166 A | 12/1982 | Furler et al. |
| 4,503,861 A | 3/1985 | Entrekin |
| 4,549,879 A | 10/1985 | Groshong et al. |
| 4,583,552 A | 4/1986 | Iinuma |
| 4,637,401 A | 1/1987 | Johnston |
| 4,644,960 A | 2/1987 | Johans |
| 4,660,565 A | 4/1987 | Shirasaka |
| 4,667,679 A | 5/1987 | Sahota |
| 4,692,148 A | 9/1987 | Kantrowitz et al. |
| 4,706,681 A | 11/1987 | Breyer et al. |
| 4,790,831 A | 12/1988 | Skribiski |
| 4,849,172 A | 7/1989 | Yafuso et al. |
| 4,856,529 A | 8/1989 | Segal |
| 4,896,677 A | 1/1990 | Kaneko et al. |
| 4,966,148 A | 10/1990 | Millar |
| 4,967,753 A | 11/1990 | Haase et al. |
| 4,979,510 A | 12/1990 | Franz et al. |
| 5,038,789 A | 8/1991 | Frazin |
| 5,046,497 A | 9/1991 | Millar |
| 5,047,930 A | 9/1991 | Martens et al. |
| 5,058,597 A | 10/1991 | Onoda et al. |
| 5,078,148 A | 1/1992 | Nassi et al. |
| 5,078,678 A | 1/1992 | Katims |
| 5,105,818 A | 4/1992 | Christian et al. |
| 5,107,841 A | 4/1992 | Sturgill |
| 5,125,410 A | 6/1992 | Misono et al. |
| 5,174,295 A | 12/1992 | Christian et al. |
| 5,190,045 A | 3/1993 | Frazin |
| 5,207,226 A | 5/1993 | Bailin et al. |
| 5,220,924 A | 6/1993 | Frazin |
| 5,226,421 A | 7/1993 | Frisbie et al. |
| 5,269,289 A | 12/1993 | Takehana et al. |
| 5,271,404 A | 12/1993 | Corl et al. |
| 5,311,871 A | 5/1994 | Yock |
| 5,325,860 A | 7/1994 | Seward et al. |
| 5,421,338 A | 6/1995 | Crowley et al. |
| 5,431,628 A | 7/1995 | Millar |
| 5,477,858 A | 12/1995 | Norris et al. |
| 5,492,125 A | 2/1996 | Kim et al. |
| 5,546,949 A | 8/1996 | Frazin et al. |
| 5,560,306 A | 10/1996 | Kyuno et al. |
| 5,566,674 A | 10/1996 | Weng |
| 5,575,286 A | 11/1996 | Weng et al. |
| 5,588,432 A | 12/1996 | Crowley |
| 5,640,961 A | 6/1997 | Verdonk |
| 5,657,760 A | 8/1997 | Ying et al. |
| 5,666,958 A | 9/1997 | Rothenberg et al. |
| 5,669,389 A | 9/1997 | Rotteveel et al. |
| 5,693,032 A | 12/1997 | Bierman |
| 5,697,377 A | 12/1997 | Wittkampf |
| 5,709,210 A | 1/1998 | Green et al. |
| 5,722,959 A | 3/1998 | Bierman |
| 5,733,323 A | 3/1998 | Buck et al. |
| 5,749,364 A | 5/1998 | Sliwa, Jr. et al. |
| 5,782,766 A | 7/1998 | Weng et al. |
| 5,785,657 A | 7/1998 | Breyer et al. |
| 5,795,298 A | 8/1998 | Vesely et al. |
| 5,803,083 A | 9/1998 | Buck et al. |
| 5,836,882 A | 11/1998 | Frazin |
| 5,857,973 A | 1/1999 | Ma et al. |
| 5,860,951 A | 1/1999 | Eggers et al. |
| 5,876,342 A | 3/1999 | Chen et al. |
| 5,878,746 A | 3/1999 | Lemelson et al. |
| 5,891,036 A | 4/1999 | Izumi |
| 5,897,488 A | 4/1999 | Ueda |
| 5,908,385 A | 6/1999 | Chechelski et al. |
| 5,935,143 A | 8/1999 | Hood |
| 5,938,603 A | 8/1999 | Ponzi |
| 5,999,846 A | 12/1999 | Pardey et al. |
| 6,007,491 A | 12/1999 | Ling et al. |
| 6,022,336 A * | 2/2000 | Zadno-Azizi .......... A61B 17/22 604/101.05 |
| 6,036,687 A * | 3/2000 | Laufer .................... A61B 18/08 604/113 |
| 6,059,731 A | 5/2000 | Seward et al. |
| 6,083,170 A * | 7/2000 | Ben-Haim .......... A61B 5/0422 600/462 |
| 6,120,445 A | 9/2000 | Grunwald |
| 6,141,576 A | 10/2000 | Littmann et al. |
| 6,179,781 B1 | 1/2001 | Phillips |
| 6,179,782 B1 | 1/2001 | Cuce |
| 6,213,947 B1 | 4/2001 | Phillips |
| 6,251,073 B1 | 6/2001 | Imran et al. |
| 6,264,611 B1 | 7/2001 | Ishikawa et al. |
| 6,364,838 B1 | 4/2002 | Freiburger et al. |
| 6,368,285 B1 | 4/2002 | Osadchy et al. |
| 6,496,712 B1 | 12/2002 | Dahl et al. |
| 6,500,130 B2 | 12/2002 | Kinsella et al. |
| 6,520,916 B1 | 2/2003 | Brennen |
| 6,542,626 B1 | 4/2003 | Brouwer et al. |
| 6,551,244 B1 | 4/2003 | Gee |
| 6,556,695 B1 | 4/2003 | Packer et al. |
| 6,561,979 B1 | 5/2003 | Wood et al. |
| 6,591,144 B2 | 7/2003 | Pigott |
| 6,594,524 B2 | 7/2003 | Esteller et al. |
| 6,612,992 B1 | 9/2003 | Hossack et al. |
| 6,638,243 B2 | 10/2003 | Kupiecki |
| 6,685,648 B2 | 2/2004 | Flaherty et al. |
| 6,689,119 B1 | 2/2004 | Di Caprio et al. |
| 6,695,785 B2 | 2/2004 | Brisken et al. |
| 6,695,865 B2 * | 2/2004 | Boyle .................. A61B 17/221 606/200 |
| 6,704,590 B2 | 3/2004 | Haldeman |
| 6,719,756 B1 | 4/2004 | Muntermann |

(56) References Cited

U.S. PATENT DOCUMENTS

| | | | |
|---|---|---|---|
| 6,733,454 B1 | 5/2004 | Bakircioglu et al. |
| 6,740,590 B1 | 5/2004 | Yano et al. |
| 6,749,606 B2 | 6/2004 | Keast et al. |
| 6,814,702 B2 | 11/2004 | Redano |
| 6,866,677 B2 | 3/2005 | Douk et al. |
| 6,896,658 B2 | 5/2005 | Ji et al. |
| 6,931,269 B2 | 8/2005 | Terry |
| 6,973,352 B1 | 12/2005 | Tsutsui et al. |
| 7,037,290 B2 | 5/2006 | Gardeski et al. |
| 7,043,293 B1 | 5/2006 | Baura |
| 7,150,716 B2 | 12/2006 | Jones et al. |
| 7,200,435 B2 | 4/2007 | Ricci et al. |
| 7,204,798 B2 | 4/2007 | Zdeblick et al. |
| 7,225,013 B2 | 5/2007 | Geva et al. |
| 7,228,164 B2 | 6/2007 | Fuimaono et al. |
| 7,346,393 B2 | 3/2008 | Spinelli et al. |
| 7,366,563 B2 | 4/2008 | Kleen et al. |
| 7,367,949 B2 | 5/2008 | Korhonen et al. |
| 7,384,411 B1 | 6/2008 | Condado |
| 7,393,501 B2 | 7/2008 | Zumeris et al. |
| 7,422,563 B2 | 9/2008 | Roschak et al. |
| 7,433,853 B2 | 10/2008 | Brockway et al. |
| 7,479,141 B2 | 1/2009 | Kleen et al. |
| 7,485,095 B2 | 2/2009 | Shusterman |
| 7,599,730 B2 | 10/2009 | Hunter et al. |
| 7,627,386 B2 | 12/2009 | Mo et al. |
| 7,640,055 B2 | 12/2009 | Geva et al. |
| 7,668,579 B2 | 2/2010 | Lynn |
| 7,697,972 B2 | 4/2010 | Verard et al. |
| 7,708,696 B2 | 5/2010 | Ritter et al. |
| 7,733,224 B2 | 6/2010 | Tran |
| 7,794,407 B2 | 9/2010 | Rothenberg |
| 7,833,221 B2 | 11/2010 | Voegele et al. |
| 7,966,061 B2 | 6/2011 | Al-Abed et al. |
| 7,981,038 B2 | 7/2011 | Kanade et al. |
| 7,991,458 B2 | 8/2011 | Hardahl et al. |
| 7,996,061 B2 | 8/2011 | Mollard et al. |
| 8,046,052 B2 | 10/2011 | Verard et al. |
| 8,052,648 B2 | 11/2011 | Dikeman et al. |
| 8,060,185 B2 | 11/2011 | Hunter et al. |
| 8,208,989 B2 | 6/2012 | Maschke et al. |
| 8,409,103 B2 | 4/2013 | Grunwald et al. |
| 8,645,962 B2 | 2/2014 | Kono et al. |
| 8,965,490 B2 | 2/2015 | Lee et al. |
| 2002/0010461 A1 | 1/2002 | KenKnight et al. |
| 2002/0045810 A1 | 4/2002 | Ben-Haim |
| 2002/0087156 A1 | 7/2002 | Maguire et al. |
| 2002/0111548 A1 | 8/2002 | Swanson et al. |
| 2002/0151790 A1 | 10/2002 | Abend |
| 2002/0156363 A1 | 10/2002 | Hunter et al. |
| 2002/0165535 A1* | 11/2002 | Lesh ............ A61B 17/2202 |
| | | | 606/41 |
| 2002/0168618 A1 | 11/2002 | Anderson et al. |
| 2002/0188257 A1 | 12/2002 | Bierman |
| 2003/0083717 A1 | 5/2003 | Mlynski et al. |
| 2003/0109785 A1 | 6/2003 | Buck et al. |
| 2003/0111548 A1 | 6/2003 | Buck |
| 2003/0204187 A1 | 10/2003 | Hintringer et al. |
| 2003/0220568 A1 | 11/2003 | Hansmann et al. |
| 2004/0011358 A1 | 1/2004 | Smaldone et al. |
| 2004/0039436 A1 | 2/2004 | Spenser et al. |
| 2004/0102719 A1 | 5/2004 | Keith et al. |
| 2004/0116809 A1 | 6/2004 | Chow et al. |
| 2004/0116969 A1 | 6/2004 | Owen et al. |
| 2004/0158143 A1 | 8/2004 | Flaherty et al. |
| 2004/0220471 A1 | 11/2004 | Schwartz |
| 2004/0225215 A1 | 11/2004 | Querleux et al. |
| 2004/0254523 A1 | 12/2004 | Fitzgerald et al. |
| 2005/0075662 A1* | 4/2005 | Pedersen ............ A61B 17/22 |
| | | | 606/194 |
| 2005/0085718 A1 | 4/2005 | Shahidi |
| 2005/0085769 A1 | 4/2005 | MacMahon et al. |
| 2005/0148836 A1 | 7/2005 | Kleen et al. |
| 2005/0159738 A1 | 7/2005 | Visram et al. |
| 2005/0203360 A1 | 9/2005 | Brauker et al. |
| 2006/0079868 A1 | 4/2006 | Makin et al. |
| 2006/0084883 A1 | 4/2006 | Linker |
| 2006/0094923 A1 | 5/2006 | Mate |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0167738 A1 | 7/2007 | Timinger et al. |
| 2007/0248640 A1* | 10/2007 | Karabey ............ A61B 17/0057 |
| | | | 424/423 |
| 2007/0265526 A1 | 11/2007 | Govari et al. |
| 2007/0276334 A1 | 11/2007 | Bierman et al. |
| 2008/0058607 A1 | 3/2008 | Watrous |
| 2008/0161669 A1 | 7/2008 | Hauck et al. |
| 2008/0188740 A1 | 8/2008 | Diaz et al. |
| 2009/0005675 A1 | 1/2009 | Grunwald et al. |
| 2009/0118612 A1 | 5/2009 | Grunwald et al. |
| 2009/0143740 A1 | 6/2009 | Bierman et al. |
| 2009/0156926 A1 | 6/2009 | Messerly et al. |
| 2009/0177090 A1 | 7/2009 | Grunwald et al. |
| 2009/0182283 A1 | 7/2009 | Sloan |
| 2009/0234328 A1 | 9/2009 | Cox et al. |
| 2009/0259124 A1 | 10/2009 | Rothenberg |
| 2009/0262977 A1 | 10/2009 | Huang et al. |
| 2009/0287070 A1 | 11/2009 | Baker, Jr. |
| 2009/0287191 A1 | 11/2009 | Ferren et al. |
| 2010/0036227 A1 | 2/2010 | Cox et al. |
| 2010/0204569 A1 | 8/2010 | Burnside et al. |
| 2011/0257600 A1 | 10/2011 | Kessler |
| 2012/0035434 A1 | 2/2012 | Ferren et al. |
| 2012/0136242 A1 | 5/2012 | Qi et al. |
| 2013/0289417 A1 | 10/2013 | Grunwald et al. |
| 2013/0296693 A1 | 11/2013 | Wenzel et al. |
| 2013/0296725 A1 | 11/2013 | Lee et al. |

FOREIGN PATENT DOCUMENTS

| | | |
|---|---|---|
| CN | 1899222 A | 1/2007 |
| DE | 4319033 C1 | 6/1994 |
| EP | 0238791 A2 | 9/1987 |
| EP | 0917069 A1 | 5/1999 |
| EP | 1181895 A2 | 2/2002 |
| EP | 1393674 A1 | 3/2004 |
| EP | 1509866 A1 | 3/2005 |
| JP | 62500703 A | 3/1987 |
| JP | S62236532 A | 10/1987 |
| JP | H0417843 B2 | 1/1992 |
| JP | H04501972 A | 4/1992 |
| JP | H073608 A | 1/1995 |
| JP | H07505791 A | 6/1995 |
| JP | 08229044 A | 9/1996 |
| JP | 09253084 A | 9/1997 |
| JP | 10277039 A | 10/1998 |
| JP | 2000514320 A | 10/2000 |
| JP | 3205040 B2 | 9/2001 |
| JP | 2004500210 A | 1/2004 |
| JP | 2004130114 A | 4/2004 |
| JP | 2005152654 A | 6/2005 |
| JP | 2006513731 A | 4/2006 |
| WO | WO8602540 A1 | 5/1986 |
| WO | WO9104707 A1 | 4/1991 |
| WO | WO9308738 A1 | 5/1993 |
| WO | WO9808440 A1 | 3/1998 |
| WO | WO9927994 A1 | 6/1999 |
| WO | WO0170303 A2 | 9/2001 |
| WO | WO0174249 A1 | 10/2001 |
| WO | WO2004030753 A1 | 4/2004 |
| WO | WO2006051523 A2 | 5/2006 |
| WO | WO2006122001 A2 | 11/2006 |
| WO | WO2007017771 A2 | 2/2007 |
| WO | WO2007047360 A2 | 4/2007 |
| WO | WO2007082093 A2 | 7/2007 |

OTHER PUBLICATIONS

Benchimol et al.; Right atrium and superior vena cava flow velocity in man measured with the doppler-catheter flowmeter-telemetry system; The Amer. J. of Med.; vol. 48; pp. 303-309; 1970.

(56) References Cited

OTHER PUBLICATIONS

Bidoggia et al.; Transseptal left heart catheterization; usefulness of the intracavitary electrocardiogram in the localization of the fossa ovalis; Catheterization and Cardiovascular Diagnosis; New York, NY; vol. 24; No. 3; pp. 221-225; Nov. 1, 1991.

Bossert etg al.; Swan-Ganz catheter-induced severe complications in cardiac surgery; right ventricular perforation, (knotting, and rupture of a pulmonary artery; J. Car. Surg.; vol. 21; No. 3; pp. 292-295; May/Jun. 2006.

Brunner, Eberhard; Ultrasound system considerations and their impact on front-end components; Analog Devices, Inc.; pp. 1-19; May-Jun. 2002.

Fearon et al.; Evaluating intermediate coronary lesions in the cardiac catheterization laboratory; Rev Cardiovasc Med; vol. 4; No. 1; pp. 1-7; 2003.

Hellerstein et al.; Recording of intracavity potentials through a single lumen, saline filled cardiac catheter; P.S.E.B.M.,; vol. 71; pp. 58-60; 1949.

Kalmanson et al.; Letter to the Editor; "Directional vs bidirectional doppler velocimeter"; Am. Heart J.; vol. 83; No. 3; pp. 437; Mar. 1972.

Lewis et al.; A Study of Normal and abnormal femoral venous flow velocity using a directional doppler; Br. J. Surg: vol. 59; No. 4; pp. 303; Apr. 1972.

McGee, et al.; Accurate placement of central venous catheters: A prospective, randomized, multicenter trial; Critical Care Medicine, vol. 21, No. 8, pp. 1118-1123, Aug. 1993.

Naylor; Reduction of malposition in peripherally inserted central catheters with tip location system; JAVA; vol. 12; No. 1; pp. 29-31; 2007.

Pittiruti et al.; The EKG method for positioning the tip of PICCs; results from two preliminary studies; JAVA; vol. 13; No. 4; pp. 112-119; 2008.

Radke et al.; control of the placement of a central venous catheter using doppler ultrasound; Der Anaesthesist 1990-05; vol. 39; No. 5; pp. 283-287; May 1990.

Schummer et al.; Central venous catheters-the inability of 'infra-atrial ECG' to prove adequate positioning; British Jour. of Anaesthesia, vol. 93, No. 2; pp. 193-198, 2004.

Starr, et al.; EKG guided placement of subclavian CVP catheters using J-wire; Ann. Surg.; vol. 204, No. 6, pp. 673-676, Dec. 1986.

Stas et al.; Peroperative intravasal electrographic control of catheter tip position in access ports placed by venous cut-down technique; EJSO; vol. 27; pp. 316-320; 2001.

Joshi et al, Optimal positioning of right-sided internal jugular venous catheters: Comparison of intra-atrial electrocardiography versus Peres' formula, Indian J Grit Care Med, Jan.-Mar. 2008 vol. 12 Issue 1.

"Madias,Intracardiac (superior vena cava/ right atrial) ECGs using saline solution as the conductive medium for the proper positioning of the Shiley hemodialysis catheter: is it not time to forgo the postinsertion chestradiograph?, Chest, American College of Chest Physicians, Dec. 2003, vol. 124, No. 6."

\* cited by examiner

Device for single beam imaging guidance of Vascular Access

Endovascular (24, 25, 29) and Transcutaneous Doppler (20, 21, 23) ultrasound systems with optional synchronization (26)

The catheter-based Doppler sensor (27) interacts with the Doppler imaging transducer (23) when it is situated in the transducer's field of view determined by the axis 28, distance $d$ and angle.

Example of Workflow Tracking

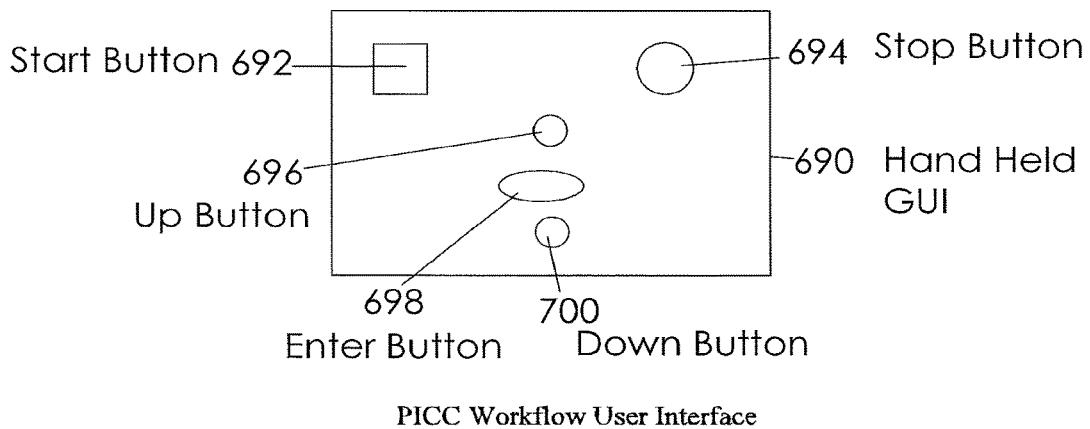

PICC Workflow User Interface

FIG. 46

PICC WORKFLOW/DATA TRACKING

Patient: Joe Smith    MRN: 09346721    Date: 05/01/2008

- Receive consult                                                            08:45 – 09:10

- Work types
  - Gather patient data (check history, allergies, labs, etc.)    09:10 – 09:20
  - Transportation to case (cart/supplies) and patient consent   09:20 – 09:35
  - Sterile setu•                                                              09:35 – 09:45
  - Venipuncture                                                           09:45 –
  - Catheter insertion/placement
  - Verification of tip position
  - Secure catheter
  - Order/wait for x-ray
  - Confirm catheter ready for use

- Change times

PICC Workflow Tracking

FIG. 47

APPARATUS AND METHOD FOR VASCULAR ACCESS

CROSS-REFERENCE TO RELATED APPLICATIONS

This application is a divisional application of U.S. patent application Ser. No. 12/147,413, filed Jun. 26, 2008, which claims the benefit of U.S. Provisional Patent App. No. 60/937,280, filed on Jun. 26, 2007, which is incorporated herein by reference in its entirety.

This application is also a continuation-in-part of U.S. patent application Ser. No. 11/431,140, filed May 8, 2006, and now U.S. Pat. No. 9,204,819, issued Dec. 8, 2015; U.S. patent application Ser. No. 11/431,118, filed May 8, 2006, and now U.S. Pat. No. 9,198,600, issued Dec. 1, 2015; U.S. patent application Ser. No. 11/431,093 filed May 8, 2006, and now U.S. Patent App. Publication No. 2007-0016069; and U.S. patent application Ser. No. 11/430,511, filed May 8, 2006, and now U.S. Pat. No. 8,409,103, issued Apr. 2, 2013, all of which claim the benefit of U.S. Provisional Patent App. No. 60/678,209, filed May 6, 2005, and U.S. Provisional Patent App. No. 60/682,002, filed May 18, 2005, each of which is incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The field of the invention relates to guided cannulation of veins and arteries. The field of the invention also relates to the guidance, positioning and placement confirmation of intravascular devices without the help of X-ray imaging. The field of the invention further relates to the workflow of vascular access procedures, in particular at the bedside.

BACKGROUND

Currently, preparing the patient for and performing vein and artery cannulation is time consuming, challenging in terms of locating the blood vessels and, under circumstances, ensuring the desired vessel is accessed (e.g., vein vs. artery). Current guided cannulation devices are either too expensive or difficult to use. General purpose imaging systems are gaining acceptance but they are expensive and represent an increase in workflow complexity because they are not sterile. In addition, general imaging systems are limited in terms of their ability to image in near field, i.e., closed to the surface of the skin. There is a need for improved placant devices.

Additional challenges remain unaddressed in many areas related to endovascular devices. One challenge that remains is for devices and methods endovascular positioning within or towards the center of a vessel. Another challenge that remains are devices and methods that rely on acoustic triangulation or positioning to localize and place endovascular devices. Another challenge related to work flow efficiency and monitoring of the placement and confirmation of endovascular device locations. There remains a need in the endovascular field for devices, systems and methods that address these challenges.

In addition RFID (radio frequency identification) tags are currently being used for a number of applications including medical, in particular for inventory management. The idea of using RFID to optimize processes has been applied for tracking documents in a workflow.

SUMMARY OF THE INVENTION

In an aspect, embodiments of the invention relate to the effective and accurate placement of intravascular devices such as central venous catheters, in particular such as peripherally inserted central catheters or PICC. One aspect of the present invention relates to vascular access. It describes devices and methods for imaging guided vascular access and more effective sterile packaging and handling of such devices. A second aspect of the present invention relates to the guidance, positioning and placement confirmation of intravascular devices without the help of X-ray imaging. A third aspect of the present invention relates to devices and methods for the skin securement of intravascular devices and post-placement verification of location of such devices. A forth aspect of the present invention relates to improvement of the workflow required for the placement of intravascular devices.

Some embodiments of the invention provide devices and methods to substantially reduce the amount of time required to place an intravascular device using conventional devices and methods. Some embodiments of the invention provide devices and methods to substantially reduce the need for X-ray imaging related to placing such device. Some embodiments of the invention provide devices and methods to increase placement reliability and accuracy and to verify device location post-placement.

Other aspects of the various embodiments are outlined in the detailed description that follows.

An aspect of the invention includes a transcutaneous ultrasound vascular access guiding system comprising: a single element ultrasound device providing A-Mode imaging, Doppler and correlation-based blood velocity estimation; a processor to process and correlate ultrasound information; and a system for information output. The transcutaneous ultrasound vascular access guiding system may also comprise a lens which controls the single element ultrasound beam shape. The transcutaneous ultrasound vascular access guiding system may also comprise a lens which provides a matching layer between the ultrasound transducer and the skin. transcutaneous ultrasound vascular access guiding system comprising can be constructed as a single-use device. Also, the information can be output as a scrolling chart. The Doppler information can be bidirectional. The Doppler acquisition can be pulsed or continuous wave (PW or CW).

Another aspect of the invention includes an endovascular device guide attached to the imaging device capable of guiding several types of endovascular devices comprising a needle, a stylet, a catheter, and an introducer. The device may include adaptors to match the outer diameter of the endovascular guided device to the inner diameter of the guide. The device having the ability to slide or otherwise move with respect to the imaging device as to provide single hand deployment capability of the endovascular guided device.

Another aspect of the invention comprises a method of accessing a blood vessel comprising the steps of: preparing sterile vascular access site on patient's skin; sliding an access needle or any other type of access device in the device guide, flush align with the tip of the imaging element, and lock in position; positioning the assembly on the patient's skin on the sterile site without the use of ultrasound gel; orienting the assembly like a flashlight until the desired vessel can be seen on the scrolling chart display; advancing the endovascular element into the vasculature by sliding the guide element over the imaging device; and monitoring the advancement of the endovascular device towards the desired target by using at least one element from a list including A-mode imaging, Doppler flow information, and/or correlation-based blood flow information.

Another aspect of the invention comprises an endovascular device capable of emitting audible sounds. The sound emitting element or elements may be placed anywhere along the endovascular member. The sound generating elements may be actuated by pushing and pulling wires manually. The sound generating elements may be actuated by motorized movement of moving connective parts. The sound generating elements may be actuated by delivering a gas through a lumen of the endovascular device. The sound generating elements may be actuated by delivering fluid through a lumen of the endovascular device. The sound generating elements may be actuated through interaction with the blood or anatomical sites. The sound waves may be generated by rubbing together of notched or serrated components. The sound waves may be generated by hitting a stylet against a solid member in order to generate a repetitive ping. The sound waves may be generated by a moving membrane. The sound waves may be generated by a moving membrane configured to amplify sound. A device lumen is configured to amplify sound.

Another aspect of the invention comprises an auscultation system comprising one or more sound sensitive elements. The system includes a sound processor and an information output device. The several auscultation devices can be synchronized to provide acoustic triangulation for accurate detection of the endovascular sound source.

Another aspect of the invention includes a guiding method for endovascular devices comprising the steps of: 1) one or more sound sensitive elements are placed on the patient's chest; 2) he sound emitting endovascular device is inserted in the patient's vasculature; 3) The endovascular device emits sound continuously, intermittently or on demand; and 4) Sound sensitive elements detect the sound generated by the endovascular device. The sound intensity can be used to estimate the distance between the sound emitting element and the sound sensitive element. The sound detected by several sound sensitive elements can be triangulate as to find the location of the sound source with respect to the sound detecting elements.

Another aspect of the invention includes a method to locate an endovascular device comprising an ultrasound sensor using one or several transcutaneous ultrasound systems comprising the steps of: 1) introducing an endovascular member containing an ultrasound sensor into the vasculature of a body; 2) sending and receiving ultrasound waves in the vasculature using the ultrasound sensor; 3) placing one or more transcutaneous ultrasound systems on the patient's body; detecting the interference between the endovascular ultrasound device and the transcutaneous ultrasound systems with either the endovascular sensor or with either of transcutaneous systems; notifying the user when interference has been detected such the user becomes aware of the presence of the endovascular device in the field of view of the transcutaneous systems. The endovascular device is able to emit ultrasound signals. The endovascular device is able to receive ultrasound signals. The transcutaneous ultrasound system is able to emit ultrasound signals. The transcutaneous ultrasound system is able to receive ultrasound signals transcutaneous ultrasound system. The transcutaneous ultrasound system can be an ultrasound imaging scan head connecting to an ultrasound imaging system. Several transcutaneous ultrasound systems can be used to triangulate the location of the endovascular ultrasound sensor. The endovascular ultrasound device is connected to the one or more transcutaneous system such as to allow synchronization of transmitting and receiving ultrasound waves in the same region of the body.

Another aspect of the invention includes an endovascular device comprising means to separate its tip from the inner blood vessel wall while maintaining the blood stream flow. A distal segment of the endovascular device is flexible and made of metal or polymer, and the polymer may be reinforced to increase tensile strength. The separation from the wall is provided by a star shaped balloon. The separation from the wall is provided by a 2 piece displaced asymmetrical shaped balloon. The separation from the wall is provided by a deployable circular braid. The separation from the wall is provided by a deployable balloon. The separation from the wall is provided by strips cut in the device material and deployed using a deployment member. The separation from the wall is provided by a deployable basket.

Another aspect of the invention includes an endovascular device comprising means to align its tip with the blood stream while maintaining the blood stream flow. The means comprises axial alignment that is facilitated by a tether component. The alignment with the blood stream is provided by a star shaped balloon. The alignment with the blood stream is provided by a 2 piece displaced asymmetrical shaped balloon. The alignment with the blood stream is provided by a deployable circular braid. The alignment with the blood stream is provided by a deployable balloon. The alignment with the blood stream is provided by strips cut in the device material and deployed using a deployment member. The alignment with the blood stream is provided by a deployable basket.

Another aspect of the invention includes a securement device for an endovascular member which provides electrical and optical sensor connectors and actuation elements to connect and control sensors and devices attached at the distal end of the endovascular members.

Another aspect of the invention includes a system for tracking clinical procedures and improve workflow efficiency comprising: a workflow processor; an input interface; an output interface; a code reader; a communication component; and a database interface. The workflow processor stores information about procedure times, device information, patient and operator information, calculates parameters of the procedure like time duration and elapsed time between activities, and provides statistical data analysis of such parameters. The information about the endovascular procedure can be input into the system through a dedicated user interface guiding data acquisition. The output interface presents results of procedure workflow analysis. The code reader can be an RFID reader, a bar code reader or a reader of any computer readable label. The communication component can communicate over the network (wired or wireless) with the hospital information system. The communication component can communicate with other systems for tracking clinical procedures and establish a network of such systems. The database interface allows the procedure and workflow information to be archived.

Another aspect of the invention includes a method for tracking clinical procedures and improve workflow efficiency comprising the steps of: 1) Input to the time when a consult request has been received; 2) Input the time when a work step is started; and 3) Input the time when a work step is finished. The a work step comprises the following activities:

a. Gather patient data (check history, allergies, lab results, etc)
b. Transportation to case (cart/supplies)
c. Obtain patient consent
d. Gain vascular access, e.g., venipuncture
e. Place endovascular device or any other type of device
f. Provide therapy through the endovascular device
g. Remove or secure the endovascular device
h. Order/wait for x-ray or other confirmatory imaging modality
i. Reposition device in case x-ray does not confirm location; and
j. Document that endovascular device is ready for use In one aspect of the invention, there is a transcutaneous ultrasound vascular access guiding system having one or more of: an elongate body having a handle; a guide on the elongate body configured to receive a vascular access device; a single element ultrasound device on the elongate body configured to provide A-Mode imaging, Doppler and correlation-based blood velocity estimation; a processor to process and correlate ultrasound information from the single element ultrasound device; and a system for information output based on the output of the processor.

The guiding system may also include a lens positioned to control the single element ultrasound beam shape or a lens positioned on the ultrasound device configured to provide a matching layer between the ultrasound transducer and the skin.

Numerous alternatives are possible such as being constructed as a single-use device or where the information output is a scrolling chart. Additionally, the Doppler information can be bidirectional and/or the Doppler acquisition can be pulsed wave or continuous wave. Additionally, the guide attached to the imaging device is configured to guide one of the endovascular device selected from the group consisting of: a needle; a stylet; a catheter; and an introducer. There may also be an adaptor to match the outer diameter of the endovascular guided device to the inner diameter of the guide. The endovascular device may also be configured to slide or move with respect to the imaging device as to provide single hand deployment capability of the endovascular guided devices described herein.

In another aspect, there is a method of accessing a blood vessel comprising one or more of the steps of:
preparing sterile vascular access site on patient's skin; sliding a vascular access device in the device guide, flush aligning with the tip of the imaging element, and locking in position; positioning the assembly on the patient's skin on the sterile site without the use of ultrasound gel; orienting the assembly like a flashlight until the desired vessel can be seen on the scrolling chart display; advancing the endovascular element into the vasculature by sliding the guide element over the imaging device; and monitoring the advancement of the endovascular device towards the desired target by using at least one element from a list including: A-mode imaging, Doppler flow information, and correlation-based blood flow information.

In another aspect, there is an endovascular device having an elongate body; an element on or in the elongate body configured to generate, emit or produce sound waves; and a device to control the generation, emission or production of sound waves from the element. The element may be placed on or in the elongate body. In one aspect, the device to control may operate by pushing and pulling wires manually. In another aspect, the device to control may be actuated by motorized movement of moving connective parts. The device to control generation of the element may be actuated by delivering a gas through a lumen on or in the elongate body. The sound generating elements may be actuated by delivering fluid through a lumen of the endovascular device. The sound generating elements may be actuated through interaction with the blood or an anatomical site. The sound waves may be generated by rubbing notched or serrated components. The sound waves may be generated by hitting a stylet against a solid member in order to generate a repetitive ping. The sound waves may be generated by a moving membrane. The sound waves may be generated by a moving membrane configured to amplify sound. There may also be a device lumen is configured to amplify sound.

In another aspect, there is an auscultation system having one or more of: one or more sound sensitive elements; a sound processor in communication with the one or more sound sensitive elements; and an information output device in communication with the sound processor. In one aspect, the sound processor is configured such that a plurality of auscultation devices can be synchronized to provide acoustic triangulation for accurate detection of an endovascular sound source.

In another aspect, there is a guiding method for endovascular devices performed by one or more of the steps of: positioning one or more sound sensitive elements on a patient's chest; inserting a sound emitting endovascular device into the patient's vasculature; emitting, producing or generating sound or pressure waves from the endovascular device; and detecting the sound or pressure waves from the emitting step with the sound sensitive elements. In one aspect, the emitting step is performed continuously, intermittently or on demand. In another aspect, the sound intensity measured in the detecting step is used to estimate the distance between the sound emitting endovascular device and the one or more sound sensitive elements. The method may also include the step of triangulating the sounds from the detecting step to locate the sound emitting endovascular device with respect to the one or more sound sensitive elements.

In still another aspect, there is a method to locate an endovascular device comprising an ultrasound sensor using one or more transcutaneous ultrasound systems by performing the steps of: introducing an endovascular member containing an ultrasound sensor into the vasculature of a body; sending and receiving ultrasound waves in the vasculature using the ultrasound sensor; placing one or more transcutaneous ultrasound systems on the patient's body; detecting the interference between the endovascular ultrasound device and the transcutaneous ultrasound systems using either the endovascular sensor or with any of the transcutaneous systems; and notifying the user when interference has been detected such the user becomes aware of the presence of the endovascular device in the field of view of the transcutaneous systems. In one alternative, the endovascular device is configured to emit or receive ultrasound signals. In one alternative, the transcutaneous ultrasound system is configured to emit or receive ultrasound signals. In another aspect, the transcutaneous ultrasound system is configured as an ultrasound imaging scan head connecting to an ultrasound imaging system. The information in the detecting step from several transcutaneous ultrasound systems is used for triangulating and/or locating the endovascular ultrasound sensor. In another alternative, the endovascular ultrasound device is connected to the one or more transcutaneous system such as to allow synchronization of transmitting and receiving ultrasound waves in the same region of the body.

In another alternative embodiment, there is an endovascular device with an elongate body sized for insertion into the vasculature; a sensor on the distal end of the elongate body; and a structure on or in the elongate body to move its tip from an inner blood vessel wall while maintaining the blood stream flow when the endovascular device is in a blood vessel. The elongate body may also include a distal segment that is flexible and made of metal or polymer, and the polymer may be reinforced to increase tensile strength. The structure is a star shaped balloon on or about the elongate body; or a 2 piece displaced asymmetrical shaped balloon; or a deployable circular braid; or deployable balloon; or a deployable basket. In one aspect, the structure also includes strips cut in the elongate body material; and the strips are adapted to be deployed to move the endovascular device from a wall using a deployment member.

In still another aspect, there is an endovascular device having an elongate body sized for insertion into the vasculature; a sensor on the distal end of the elongate body; and a structure configured to align the elongate body tip or the sensor with the blood stream while maintaining the blood stream flow. The structure may include axial alignment or alignment within the bloodstream facilitated by a tether component attached to the elongate body; or provided by a star shaped balloon; or provided by a 2 piece displaced asymmetrical shaped balloon; or provided by a deployable circular braid; or provided by a deployable balloon; or provided by strips cut in the elongate body material and deployed using a deployment member; or provided by a deployable basket.

In another alternative embodiment, there is a securement device for an endovascular member that provides electrical and optical sensor connectors and actuation elements to connect and control sensors and devices attached at the distal end of the endovascular members.

In another aspect, there is a system for tracking clinical procedures and workflow having one or more of: a workflow processor; an input interface; an output interface; a code reader; a communication component; and a database interface. The workflow processor may store information about procedure times, device information, patient and operator information, calculate parameters of the procedure like time duration and elapsed time between activities, and provide statistical data analysis of such parameters. The information about the endovascular procedure may be input into the system through a dedicated user interface guiding data acquisition. The output interface may present results of procedure workflow analysis. The code reader can be an RFID reader, a bar code reader or a reader of any computer readable label. The communication component can communicate over a wired network or a wireless network with a hospital information system. The communication component can communicate with other systems for tracking clinical procedures and establish a network of such systems. The database interface allows the procedure and workflow information to be archived.

In another aspect, there is a method for tracking clinical procedures and workflow, having one or more of the steps of: entering a time when a consult request is received; entering a time when a work step is started; and entering a time when a work step is finished. The work step may include one or more of the following activities: gathering patient data; transporting to a case; obtaining patient consent; gaining vascular access; placing an endovascular device or any other type of device; providing therapy through the endovascular device; removing or securing an endovascular device; ordering or waiting for x-ray or other confirmatory imaging modality; repositioning a device based on input from an imaging modality; and documenting that an endovascular device is ready for use.

BRIEF DESCRIPTION OF THE DRAWINGS

FIG. 12 illustrated the concept of orienting the transducer a minimum distance from the vessel wall as seen in.

FIGS. 13A and 13B illustrate the concept of aligning the transducer at an angle from the flow axis as shown in.

FIG. 14 shows a transition section made of a relatively much more flexible material than what the proximal or distal sections are made of.

FIG. 46 illustrates a VasoNova handheld GUI has a menu feature that indicates which workflow interval is being tracked and the operator can modify or change the present task by using the 'up' and 'down' buttons on the data entry device.

FIG. 47 illustrates a GUI that will display the tasks and with the present task highlighted as illustrated in.

DETAILED DESCRIPTION

Figure 1:
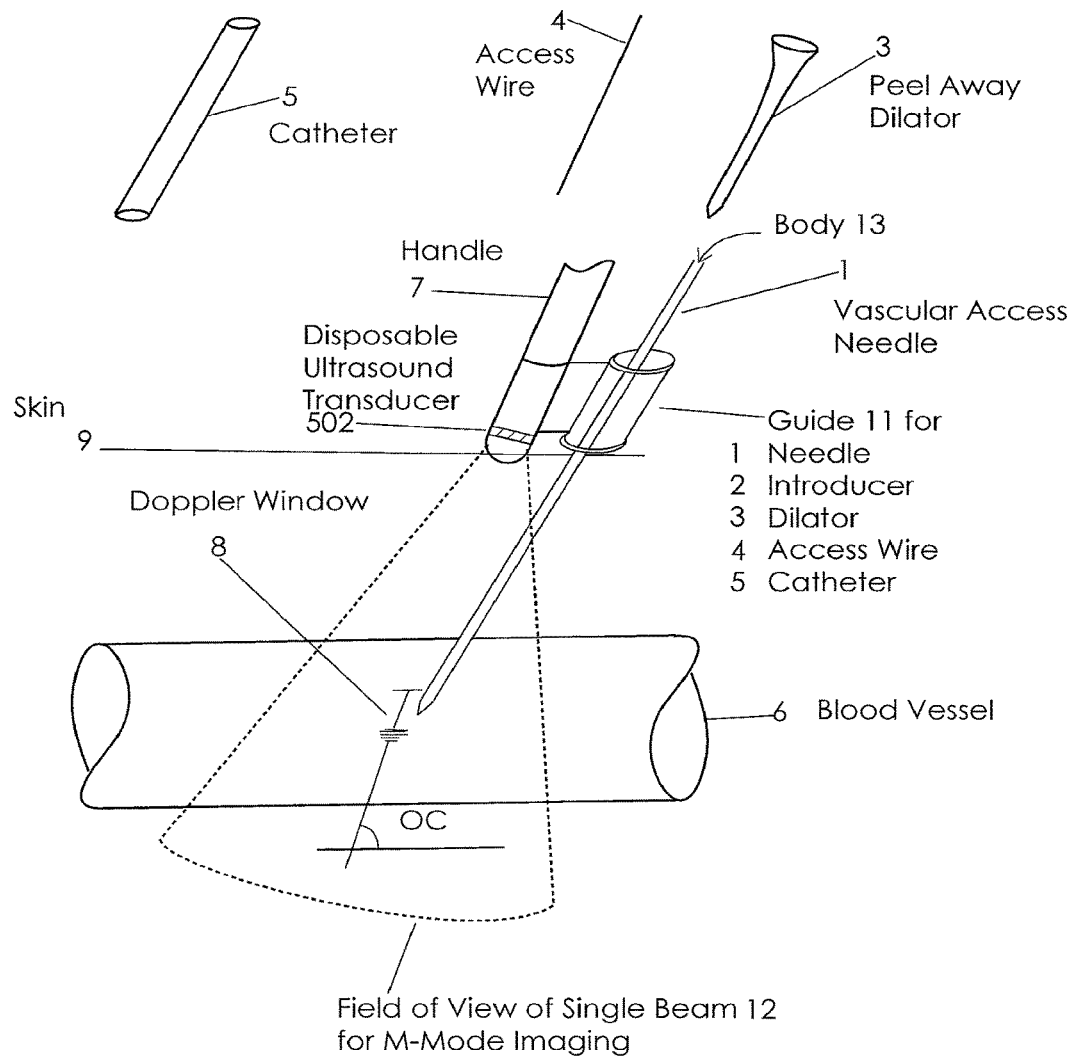
FIG. 1 illustrates a disposable or reusable imaging and guiding device for vascular access.

An aspect of the invention includes a transcutaneous ultrasound vascular access guiding system comprising: a single element ultrasound device providing A-Mode imaging, Doppler and correlation-based blood velocity estimation; a processor to process and correlate ultrasound information; and a system for information output. The transcutaneous ultrasound vascular access guiding system may also comprise a lens which controls the single element ultrasound beam shape. The transcutaneous ultrasound vascular access guiding system may also comprise a lens which provides a matching layer between the ultrasound transducer and the skin. transcutaneous ultrasound vascular access guiding system comprising can be constructed as a single-use device. Also, the information can be output as a scrolling chart. The Doppler information can be bidirectional. The Doppler acquisition can be pulsed or continuous wave (PW or CW).

Another aspect of the invention includes an endovascular device guide attached to the imaging device capable of guiding several types of endovascular devices comprising a needle, a stylet, a catheter, and an introducer. The device may include adaptors to match the outer diameter of the endovascular guided device to the inner diameter of the guide. The device having the ability to slide or otherwise move with respect to the imaging device as to provide single hand deployment capability of the endovascular guided device.

Another aspect of the invention comprises a method of accessing a blood vessel comprising the steps of: preparing sterile vascular access site on patient's skin; sliding an access needle or any other type of access device in the device guide, flush align with the tip of the imaging element, and lock in position; positioning the assembly on the patient's skin on the sterile site without the use of ultrasound gel; orienting the assembly like a flashlight until the desired vessel can be seen on the scrolling chart display; advancing the endovascular element into the vasculature by sliding the guide element over the imaging device; and monitoring the advancement of the endovascular device towards the desired target by using at least one element from a list including A-mode imaging, Doppler flow information, and/or correlation-based blood flow information.

Another aspect of the invention comprises an endovascular device capable of emitting audible sounds. The sound emitting element or elements may be placed anywhere along the endovascular member. The sound generating elements may be actuated by pushing and pulling wires manually. The sound generating elements may be actuated by motorized movement of moving connective parts. The sound generating elements may be actuated by delivering a gas through a lumen of the endovascular device. The sound generating elements may be actuated by delivering fluid through a lumen of the endovascular device. The sound generating elements may be actuated through interaction with the blood or anatomical sites. The sound waves may be generated by rubbing together of notched or serrated components. The sound waves may be generated by hitting a stylet against a solid member in order to generate a repetitive ping. The sound waves may be generated by a moving membrane. The sound waves may be generated by a moving membrane configured to amplify sound. A device lumen is configured to amplify sound.

Another aspect of the invention comprises an auscultation system comprising one or more sound sensitive elements. The system includes a sound processor and an information output device. The several auscultation devices can be synchronized to provide acoustic triangulation for accurate detection of the endovascular sound source.

Another aspect of the invention includes a guiding method for endovascular devices comprising the steps of: 1) one or more sound sensitive elements are placed on the patient's chest; 2) he sound emitting endovascular device is inserted in the patient's vasculature; 3) The endovascular device emits sound continuously, intermittently or on demand; and 4) Sound sensitive elements detect the sound generated by the endovascular device. The sound intensity can be used to estimate the distance between the sound emitting element and the sound sensitive element. The sound detected by several sound sensitive elements can be triangulate as to find the location of the sound source with respect to the sound detecting elements.

Another aspect of the invention includes a method to locate an endovascular device comprising an ultrasound sensor using one or several transcutaneous ultrasound systems comprising the steps of: 1) introducing an endovascular member containing an ultrasound sensor into the vasculature of a body; 2) sending and receiving ultrasound waves in the vasculature using the ultrasound sensor; 3) placing one or more transcutaneous ultrasound systems on the patient's body; detecting the interference between the endovascular ultrasound device and the transcutaneous ultrasound systems with either the endovascular sensor or with either of transcutaneous systems; notifying the user when interference has been detected such the user becomes aware of the presence of the endovascular device in the field of view of the transcutaneous systems. The endovascular device is able to emit ultrasound signals. The endovascular device is able to receive ultrasound signals. The transcutaneous ultrasound system is able to emit ultrasound signals. The transcutaneous ultrasound system is able to receive ultrasound signals transcutaneous ultrasound system. The transcutaneous ultrasound system can be an ultrasound imaging scan head connecting to an ultrasound imaging system. Several transcutaneous ultrasound systems can be used to triangulate the location of the endovascular ultrasound sensor. The endovascular ultrasound device is connected to the one or more transcutaneous system such as to allow synchronization of transmitting and receiving ultrasound waves in the same region of the body.

Another aspect of the invention includes an endovascular device comprising means to separate its tip from the inner blood vessel wall while maintaining the blood stream flow. A distal segment of the endovascular device is flexible and made of metal or polymer, and the polymer may be reinforced to increase tensile strength. The separation from the wall is provided by a star shaped balloon. The separation from the wall is provided by a 2 piece displaced asymmetrical shaped balloon. The separation from the wall is provided by a deployable circular braid. The separation from the wall is provided by a deployable balloon. The separation from the wall is provided by strips cut in the device material and deployed using a deployment member. The separation from the wall is provided by a deployable basket.

Another aspect of the invention includes an endovascular device comprising means to align its tip with the blood stream while maintaining the blood stream flow. The means comprises axial alignment that is facilitated by a tether component. The alignment with the blood stream is provided by a star shaped balloon. The alignment with the blood stream is provided by a 2 piece displaced asymmetrical shaped balloon. The alignment with the blood stream is provided by a deployable circular braid. The alignment with the blood stream is provided by a deployable balloon. The alignment with the blood stream is provided by strips cut in the device material and deployed using a deployment member. The alignment with the blood stream is provided by a deployable basket.

Another aspect of the invention includes a securement device for an endovascular member which provides electrical and optical sensor connectors and actuation elements to connect and control sensors and devices attached at the distal end of the endovascular members.

Another aspect of the invention includes a system for tracking clinical procedures and improve workflow efficiency comprising: a workflow processor; an input interface; an output interface; a code reader; a communication component; and a database interface. The workflow processor stores information about procedure times, device information, patient and operator information, calculates parameters of the procedure like time duration and elapsed time between activities, and provides statistical data analysis of such parameters. The information about the endovascular procedure can be input into the system through a dedicated user interface guiding data acquisition. The output interface presents results of procedure workflow analysis. The code reader can be an RFID reader, a bar code reader or a reader of any computer readable label. The communication component can communicate over the network (wired or wireless) with the hospital information system. The communication component can communicate with other systems for tracking clinical procedures and establish a network of such systems. The database interface allows the procedure and workflow information to be archived.

Another aspect of the invention includes a method for tracking clinical procedures and improve workflow efficiency comprising the steps of: 1) Input to the time when a consult request has been received; 2) Input the time when a work step is started; and 3) Input the time when a work step is finished. The a work step comprises the following activities:

a. Gather patient data (check history, allergies, lab results, etc)

b. Transportation to case (cart/supplies)
c. Obtain patient consent
d. Gain vascular access, e.g., venipuncture
e. Place endovascular device or any other type of device
f. Provide therapy through the endovascular device
g. Remove or secure the endovascular device
h. Order/wait for x-ray or other confirmatory imaging modality
i. Reposition device in case x-ray does not confirm location; and
j. Document that endovascular device is ready for use 1.0 System for Guided and Sterile Vascular Access Aspects of the following embodiments may share some or all of the following characteristics such as disposable imaging device, an imaging device with a needle guide and the ability to cannulate a vessel in a single disposable sterile bag or container.

Free-Hand A-Mode Imaging

The free-hand A-mode imaging preferably includes a disposable, inexpensive, accurate vascular placement device that reduces access time as compared to conventional vascular placement devices and methods. The free-hand A-mode imaging preferably enables a procedure for bedside central line placement.

The patient's arm and axilla/shoulder are prepped in the usual sterile fashion. A ribbon of latex or other type tourniquet is used on the upper arm to help distend the veins.

FIG. 1 illustrates a disposable or reusable imaging and guiding device for vascular access. The device in FIG. 1 includes an elongate body 13, guide 11, a needle 1, an introducer 2, a dilator 3, an access wire 4, a catheter 5, a handle 7 and an ultrasound transducer 502. In particular, FIG. 1 illustrates an A-mode device that has a pencil or other shaped handheld device with the ultrasound device (i.e., disposable ultrasound transducer 502) at a distal tip, which may be perpendicular or at a 30, 45, 60 or other degree angle relative to an axis of the handheld device. A needle 1/guide 11 or catheter 5/needle 1 combination may also be configured as part of the device such that a beam 12 of the ultrasound transducer 502 crosses a set needle path as it pierces skin 9 and traverses subcutaneous tissues. This arrangement allows an operator to visualize the needle 1 as it punctures a blood vessel 6 of interest. The device presented in FIG. 1 may be delivered in a sterile package and is disposable.

Once a most superficial wall of a vein has been punctured a flash of blood is visualized at a hub end of the catheter 5/needle 1. The access wire 4 is then advanced through the needle 1 and the catheter 5 (if present) is then advanced over the access wire 4 into the blood vessel 6. The guiding device, needle 1/access wire 4 (as in an Angiocath combination) is then removed, leaving in place only the catheter 5. The catheter 5 is of sufficient size to allow passage of a larger access wire 4, 0.035" or larger for example, to enable placement of a peel-away sheath and dilator 3. The dilator 3 and access wire 4 are then removed and the PICC is inserted through the peel-away sheath. Alternatively, access wire 4 is advanced into the blood vessel 6 through the needle 1 and no Angiocath is utilized. The guiding device and needle 1 are then removed and the peel-away sheath and dilator 3 are advanced over the access wire 4. Once the sheath is all the way in the dilator 3 and access wire 4 are removed and the PICC is inserted through the peel-away sheath.

The guiding device connects to a VasoNova handheld with GUI by a cord or with wireless connectivity. The guiding device may be disposable or sterilizable/reusable. The catheter 5/needle 1/access wire 4 component is disposable and may be integrated with the ultrasound device if the catheter 5/needle 1/access wire 4 is disposable. The catheter 5/needle 1/access wire 4 may be inserted or attached to a reusable ultrasound device. The primary ultrasound modality is A-mode for visualizing the tissues on gray-scale with real time analysis; however the modality can also be switched manually or automatically to Doppler mode within the blood vessel lumen to confirm venous flow versus arterial flow based on velocity of blood flow and pulsatility pattern.

A handheld component of ultrasound-guided blood vessel access system may be ergonomically designed in order to optimize user positioning and angle of contact with the patient's skin. This may involve placing the ultrasound device in an enclosure that resembles a computer mouse, a pencil-shaped device, short stubby cylindrical device or other shaped handheld that can also incorporate the needle 1/access wire 4 introduction system as described above. The device may provide for the ability to swivel the ultrasound and needle guiding components to optimize position relative to the portion that is held in place by the operator and the blood vessel to be punctured.

The ultrasound-guided blood vessel access system is not exclusively intended for use in placing PICCs. The ultrasound-guided blood vessel access system may also be used for blood vessel puncture in general when the blood vessel of interest is not visible or easily palpable to the operator's satisfaction and ultrasound confirmation and guidance is desired for puncturing the blood vessel. As such the ultrasound-guided blood vessel access system may be used for accessing veins, such as peripheral veins such as the cephalic, basilica, median cubital, brachial, antecubital, or other veins of the arm, the long and short saphenous or other superficial veins in the legs, or for accessing more centrally located veins such as axillary, subclavian, internal or external jugular veins, or common femoral veins for example. The ultrasound-guided blood vessel access system may be used to identify arteries such as the radial, ulnar, brachial, axillary, femoral, or other for puncture or simple detection of blood flow, such as with a "Doppler check" as when a nurse assesses a patient's arterial blood flow in an extremity after a vascular operation during the postoperative phase.

1.1 Ultrasound-Guided Apparatus and Method for Blood Vessel Access

The Apparatus

As noted above, the apparatus in FIG. 1 includes an elongate body 13, guide 11, a needle 1, an introducer 2, a dilator 3, an access wire 4, a catheter 5, a handle 7 and an ultrasound transducer 502. The apparatus illustrated in FIG. 1 includes a single element imaging element comprising a body 13, shaped like a pen or a flashlight. The single element imaging element consist of a handle 7 and an ultrasound transducer 502. The ultrasound transducer 502 emits a single beam 12 and can consist of a single or multiple elements, e.g., piezoelectric crystals. The beam 12 can be focused, unprocessed, or divergent. Frequency of operation should be such as to allow near field imaging and penetration to the vessels of interest for cannulation, for example 7 to 10 MHz.

The apparatus contains further a detachable or fixed guide 11 which allows for sliding a needle 1, a dilator 3, an access wire 4 or a catheter 5 through the guide 11 into the blood vessel 6 and into the field of view of the ultrasound beam.

The apparatus is further capable of providing blood flow velocity and direction information using non-directional or bi-directional CW or PW Doppler or cross-correlation methods similarly to the system described in the VasoNova patent applications.

The ultrasound device (i.e. ultrasound transducer 502) is connected to an instrument for processing (i.e., processor) and displaying single beam ultrasound images in an amplitude (A-Mode) display. The type of vascular access imaging may be free hand A-Mode obtained with the device. The imaging may be color A-mode imaging, whereby the colors indicate bidirectional blood flow velocities obtained using Doppler or cross-correlation calculations, or duplex A-Mode imaging mode, where the bidirectional Doppler spectral distribution (velocity distribution) is in a sample window.

The handle 7 further comprises one or more buttons that allow for single finger operation of any component controlled by the handle 7, e.g., turning the Doppler mode on and off or adjusting the depth of the sample window.

The guide comprises a lumen adaptor to accommodate different size devices, such as for example, a dilator, an access wire, a catheter and the like.

Guided Cannulation Method

In one embodiment, a guided cannulation method includes the following steps:
1. Prepare the sterile field for cannulation;
2. Connect the sterile apparatus to the ultrasound device;
3. Use the apparatus like a flashlight to look for a target vessel using A-Mode imaging;
4. Optionally use Doppler to double check if the target vessel is a vein or an artery based on flow characteristics;
5. Attach the needle 1 to the guide 11 and insert needle 1 until needle 1 can be seen on the
A-Mode image as reaching the vessel of interest. Insert the access wire 4, dilator 3/introducer 2 and any other desired endovascular member under ultrasound visualization; and/or
6. Detach the apparatus from the inserted endovascular member, disconnect from the ultrasound device and dispose of the single use component.

2.0 Guided Endovascular Access Device
  2.1 Energy Element (Sensor and Source)
    2.1.1 Acoustic Triangulation Sound waves are generated at the catheter tip and detected by strategically placed electronically amplified auscultation devices that are in contact with the patient's skin.

The sound waves may be generated by the mechanical interaction of solid components, by transduction of vibrational energy along a stylet, by vibration of valve flaps near the catheter tip, or by pneumatic activation of a membrane that is at the interface of a gas or liquid filled catheter lumen/cavity and the patient's blood.

Figure 2:
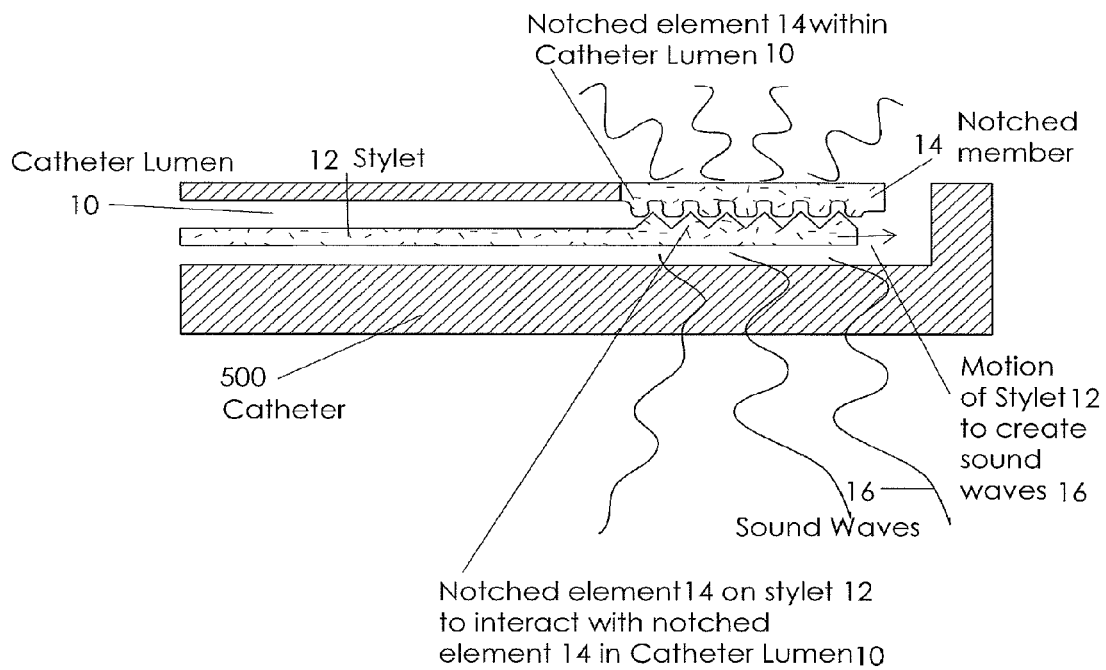
FIG. 2 illustrates interaction of solid components rubbing together of notched components at the catheter tip with similar notched or serrated components at the distal end of a stylet that passes through one of the catheter lumens.

Interaction of solid components may involve rubbing together of notched components at the catheter 500 tip with similar notched element 14 or serrated components at the distal end of a stylet 12 that passes through one of the catheter lumens 10 (FIG. 2). FIG. 2 includes a catheter 500, a catheter lumen 10, a stylet 12, a notched element 14 within catheter lumen 10, a notched member 14, sound waves 16, motion of stylet 12 to create sound waves 16 and notched element 14 on stylet 12 to interact with notched element 14 in catheter lumen 10. This type of sound wave 16 generation is similar to stridulation in certain insect species that use rubbing together of exoskeletal prominences to create sound that is necessary for identifying the location of potential mates. To generate the sound, the stylet 12 must be advanced forward and backward in rapid succession. In order to accomplish the necessary motion, the end of the stylet 12 at the hub end of the catheter 500 may be attached to a motorized device that can move the stylet 12 the correct distance, which may be from less than one centimeter of displacement up to 2 centimeters and at the correct speed in order to optimize the sound that is created.

Figure 3:
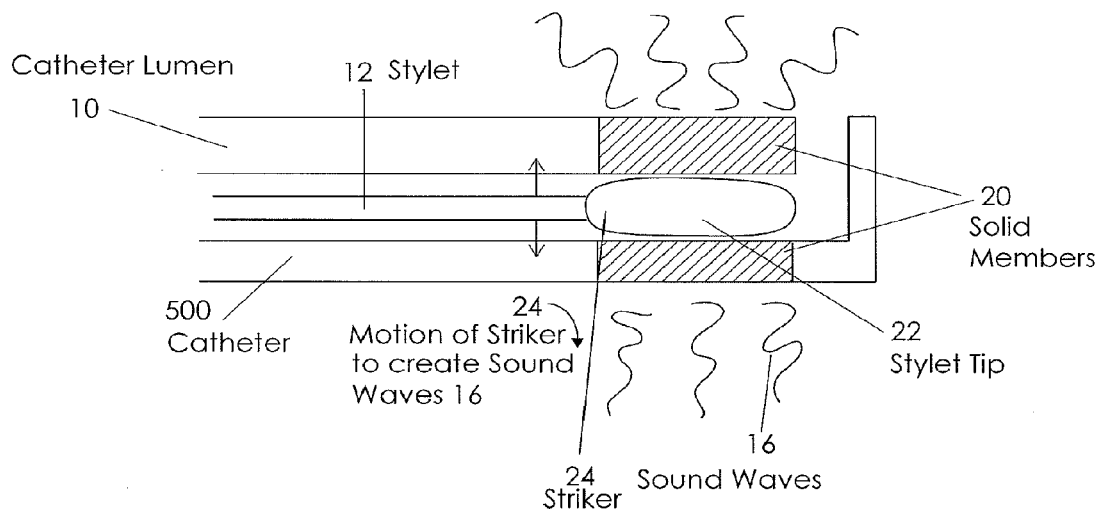
FIG. 3 shows an embodiment in which the motion required is perpendicular to the stylet axis.
Figure 4:
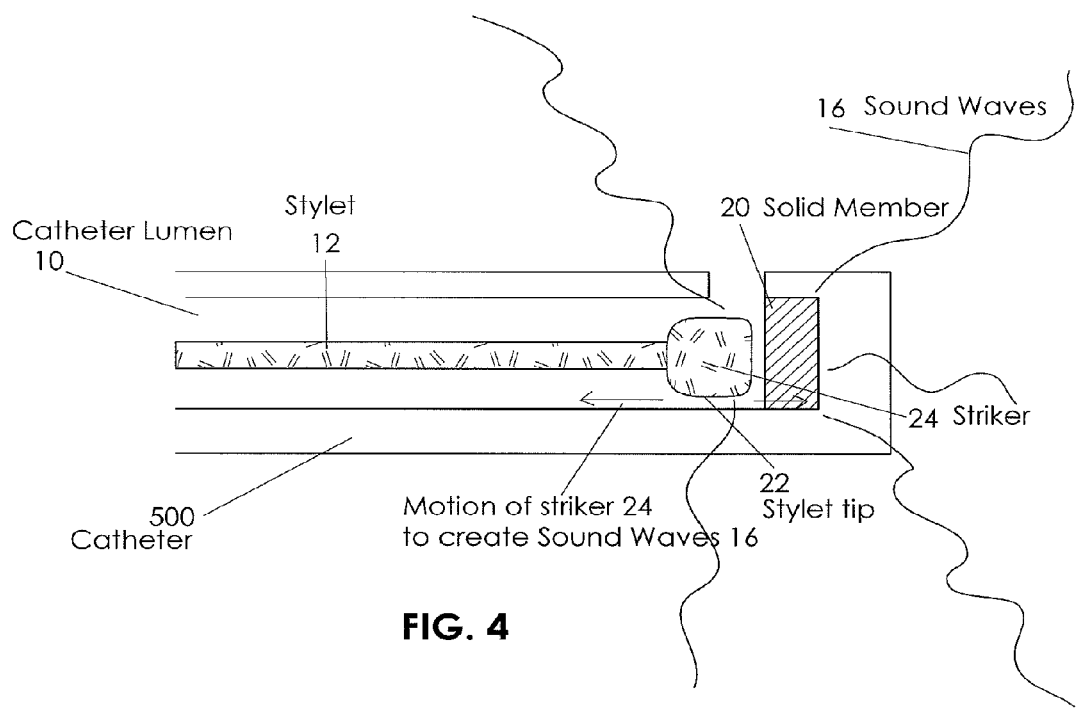
FIG. 4 shows an embodiment in which the motion required is parallel to the stylet axis.

Another method of sound generation may involve the stylet 12 hitting against a solid member at the catheter 500 tip to generate a repetitive ping. This vibratory sound generation would require that the stylet 12 be actuated or maneuvered by a motorized process that is controlled at the proximal end of the stylet 12, which is outside the patient. The stylet 12 is attached to a motorized device that will cause the stylet to move in the appropriate direction and the appropriate distance in order to optimize the sound. FIG. 3 shows an embodiment in which the motion required is perpendicular to the stylet 12 axis and FIG. 4 shows an embodiment in which the motion required is parallel to the stylet 12 axis. FIG. 3 includes catheter 500, catheter lumen 10, stylet 12, sound waves 16, stylet tip 22, solid members 20, striker 24 and motion of striker 24 to create sound waves 16. FIG. 4 includes catheter 500, catheter lumen 10, stylet 12, sound waves 16, stylet tip 22, solid member 20, striker 24 and motion of striker 24 to create sound waves 16.

Figure 5:
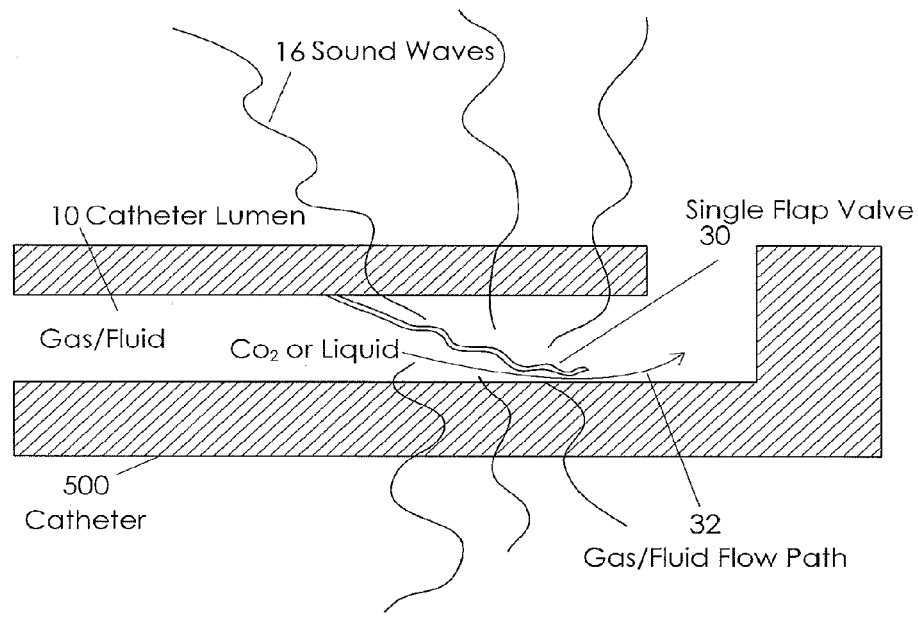
FIG. 5 illustrated motion of the valve flap or flaps is induced by the rapid injection of a liquid or gas such as $CO_2$ through the catheter lumen within which valve resides.
Figure 6:
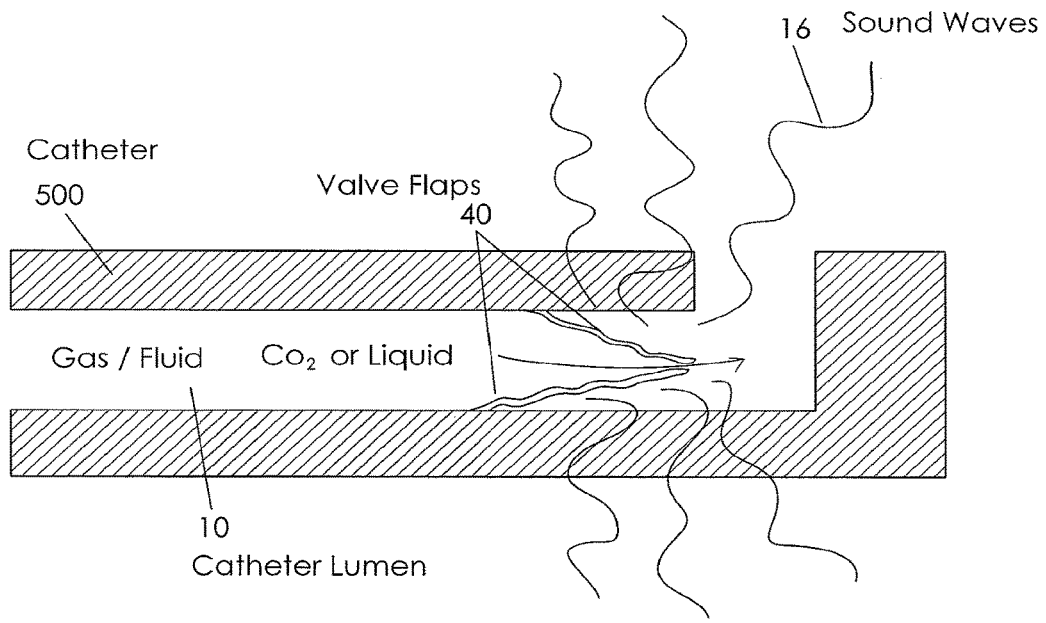
FIG. 6 illustrated motion of the valve flap or flaps is induced by the rapid injection of a liquid or gas such as $CO_2$ through the catheter lumen within which valve resides.
Figure 7:
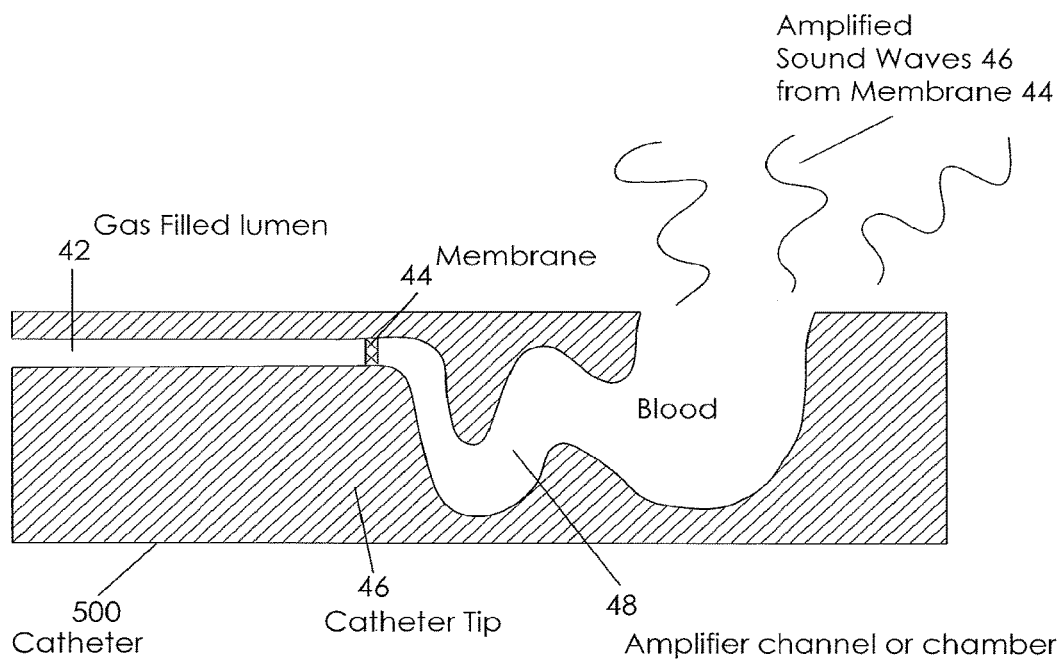
FIG. 7 illustrates an embodiment, in which a convoluted lumen acts as an amplifier, thus enabling a smaller sized membrane that can be positioned in the more proximal lumen or located at the tip of an insertable catheter that can then be removed after performing the sound triangulation procedure for verification of catheter tip position.

If a vibrating valve is used to produce sound, motion of a valve flap 30 or valve flaps 40 is induced by the rapid injection of a liquid or gas such as $CO_2$ through the catheter lumen 10 within which valve resides (FIGS. 5 and 6). FIG. 5 includes catheter 500, catheter lumen 10, sound waves 16, single flap valve 30 and gas/fluid flow path 32. FIG. 6 includes catheter 500, catheter lumen 10, sound waves 16, valve flaps 40 and gas/fluid flow path 32. The sound generated by the flap motion may be amplified by the shape of the more distal catheter lumen 10 and exit port distal to the flap as illustrated in FIG. 7. FIG. 7 includes catheter 500, catheter tip 46, amplified channel or chamber 48, gas filled lumen 42, membrane 44 and amplified sound waves 46 from membrane 44.

Figure 8:
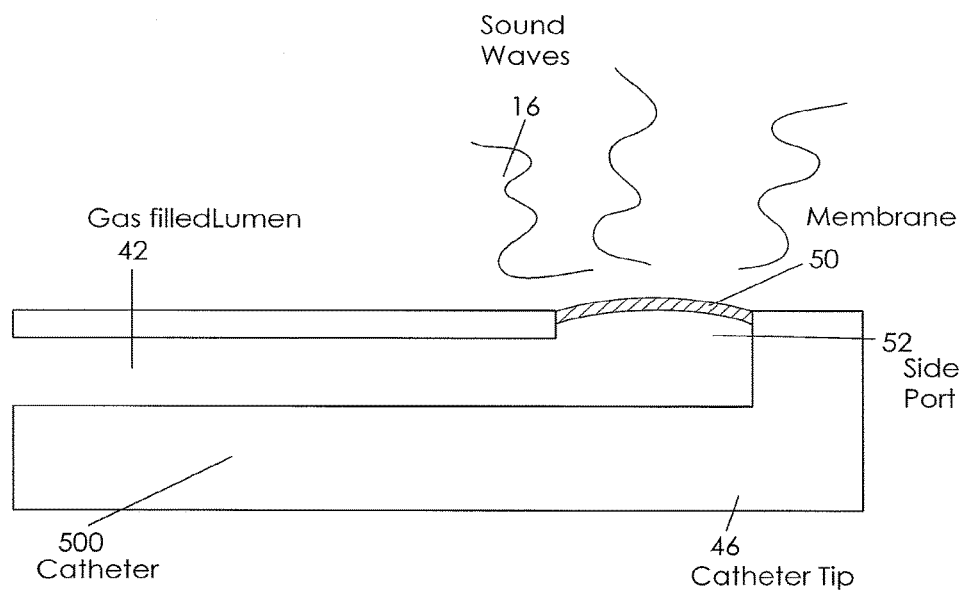
FIG. 8 illustrates a simplified embodiment in which the membrane is situated at the terminal side port of a lumen.

If a pneumatic system is employed, the catheter lumen 10 that is in contact with the membrane 44 at the catheter 500 tip is attached at the catheter 500 hub to a gas compressor device that causes rapid pneumatic pressure fluctuation, thereby distending the membrane 44 at an optimal frequency, thereby generating a sound wave that propagates through the patient's blood and adjacent soft tissues such that it can be detected by the auscultation devices that are placed on the patient's skin. FIG. 8 illustrates a simplified embodiment in which the membrane 44 is situated at the terminal side port of a lumen 10. FIG. 8 includes catheter 500, catheter tip 46, gas filled lumen 42, membrane 50, sound waves 16 and side port 52. FIG. 7 illustrates an embodiment, in which a convoluted lumen 10 acts as an amplifier, thus enabling a smaller sized membrane 44 that can be positioned in the more proximal lumen or located at the tip of an insertable catheter 500 that can then be removed after performing the sound triangulation procedure for verification of catheter tip position.

The sound waves that are generated by all methods described above are optimized for best detection by the amplified auscultation devices that are placed on the patient's skin by means of an adhesive attachment. The placement of the auscultation devices may be such as to optimize sound detection and triangulation to determine the sound source. For example, auscultation detectors should be placed in areas that will permit propagation of the sound waves in a direct path through solid tissue from the source to the detector instead of areas of the skin where a direct path from the catheter tip to the detector would pass through lung tissue for example. Potential ideal locations for detecting sound generated within the caval-atrial junction or lower ⅓ of the IVC along a direct path include but may not be limited to:

1) skin overlying the right internal jugular vein at the base of the neck,
2) skin overlying the right 4th intercostals space adjacent to the sternum,
3) skin overlying over the ipsilateral and/or contralateral subclavicular space (relative to the side of catheter insertion) at the junction of the medial ⅔ and lateral ⅓ of the calvicle, two fingerbreadths below the clavicle.

Figure 9:
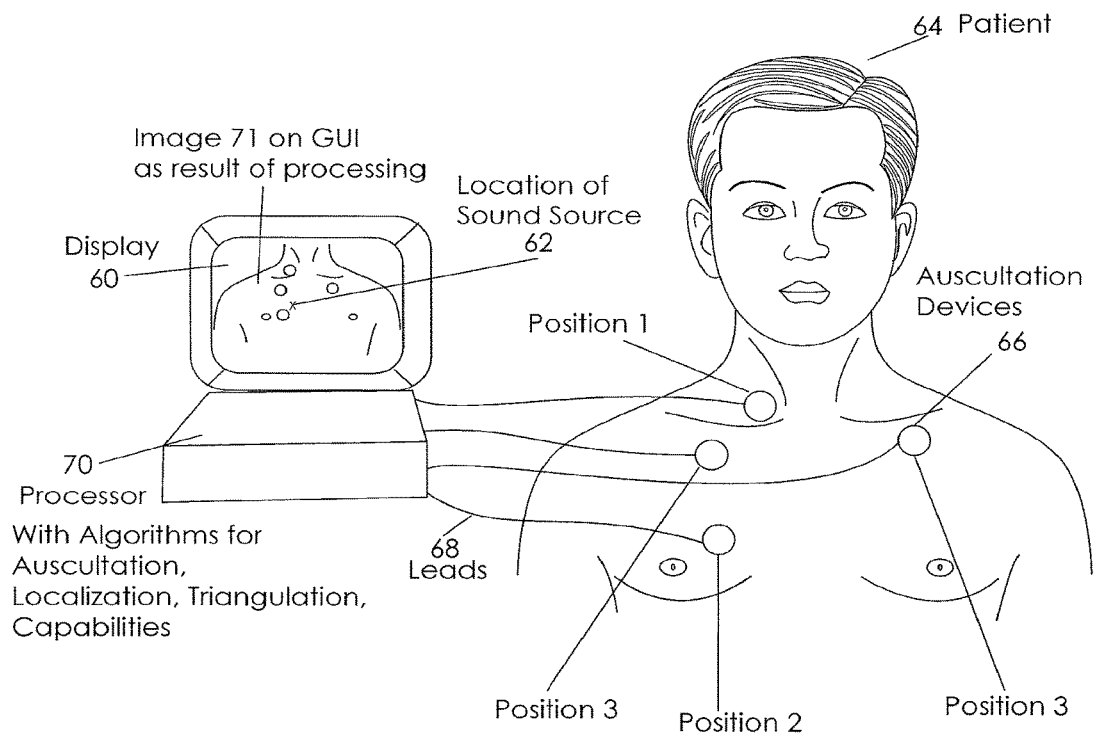
FIG. 9 illustrates the basic configuration of auscultation devices and user interface.

Detected sound frequencies and amplitudes are analyzed and processed by the handheld system according to specific algorithms and a the sound source is displayed on the handheld GUI, with the source shown relative to the auscultation devices that are depicted as reference points on a graphical human torso. FIG. 9 illustrates the basic configuration of auscultation devices and user interface. FIG. 9 includes a patient 64, auscultation devices 66, position 1, position 2, position 3, leads 68, location of sound source 62, display 60, processor 70 and image 71 on GUI as a result of processing.

2.1.2 Interaction with Transcutaneous Energy Source

An aspect of the invention relates to using two or more focused energy transmitters and receivers in order to detect each others presence in each others field of view. The overlap region between the fields of view of the two or more energy elements is indicative of the relative location of the energy elements with respect to each other. Techniques triangulation (Brisken), marking with active/passive elements (Breyer), synchronized imaging (Frazin).

Aspects of the following embodiments share some or all of the following characteristics:

1. Use of the effect of interference between two ultrasound energy elements on the Doppler frequency shift. The Doppler capable detecting elements detects the presence of the other element or of the energy emitted by the other element in its field of view by detecting artifacts in the Doppler frequency shift.
2. Visualization of small targets without requiring synchronization between energy elements.
3. Use of an endovascular element to detect the presence of the field of view of the imaging device.
4. The ability of an endovascular Doppler sensor to detect Doppler frequency shifts as a result of interference with another ultrasound energy source working at a different frequency and unsynchronized.
5. Methods to determine position of an energy element in the anatomy without X-ray imaging, without expensive automatic triangulation and with the accuracy of the region of overlap between the fields of view of the two energy elements.

These and other aspects of the various embodiments of the invention will be appreciated in the description that follows.

Figure 10:
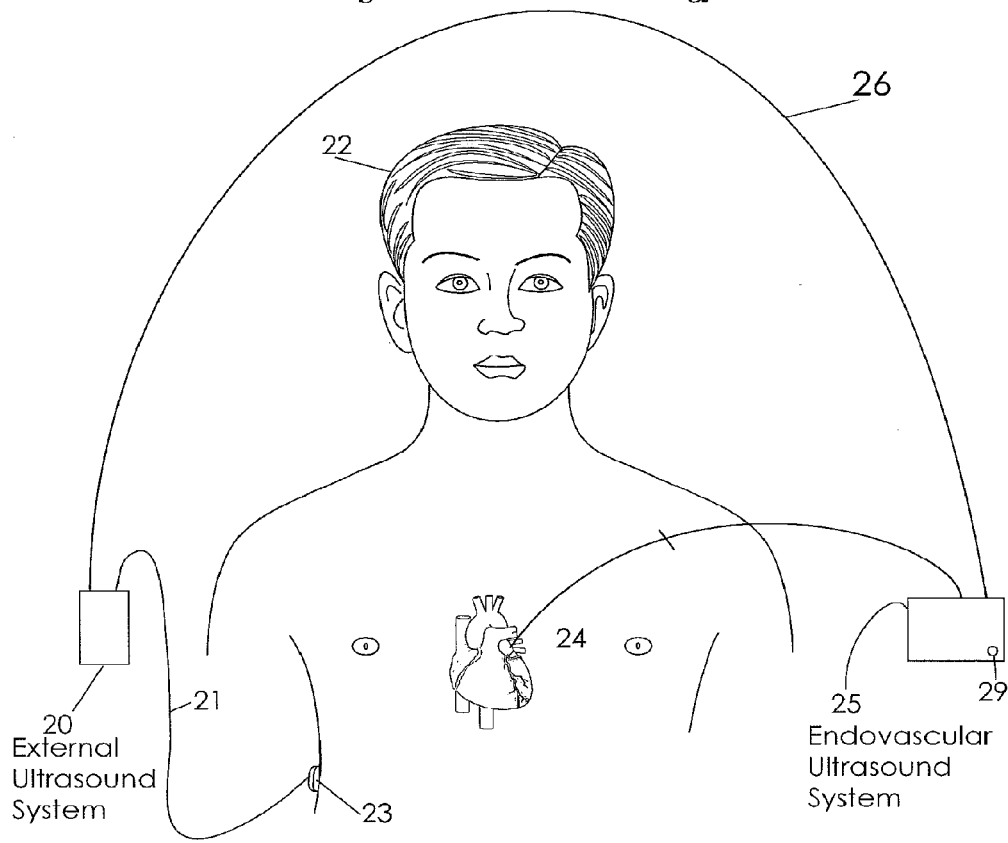
In FIG. 10 an ultrasound system (20) and transducer (23) are used as an external (transcutaneous or transesophageal) energy source.

FIG. 10 includes an external ultrasound system 20, transducer 23, wire 21, endovascular ultrasound system 25, endovascular probe 24, external connection 26 and patient 22. In FIG. 10 an ultrasound system (74) and transducer (23) are used as an external (transcutaneous or transesophageal) energy source. The system (20) may be Doppler capable. An endovascular probe (24, catheter, wire, stylet) has an ultrasound sensor attached to it and is connected to a Doppler capable ultrasound system (25). The external and the endovascular Doppler systems may be synchronized via an external connection (26).

The system (20) may be one like the Bard SiteRite (www.bardaccess.com) or the SonoSite iLook (www.sonosite.com) system working at frequencies between 4 and 8 MHz. The Doppler endovascular probe (24) may work at 10 MHz and be similar to those described in the VasoNova patent applications.

Figure 11:
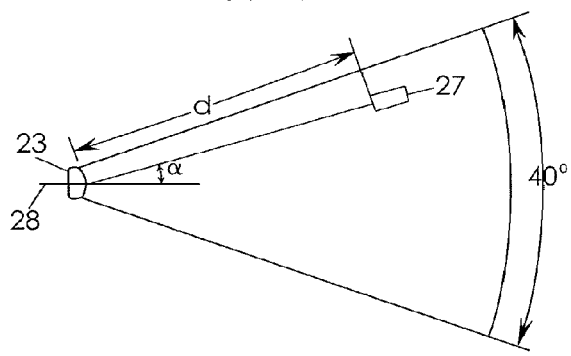
FIG. 11 illustrates possible ultrasound beam geometry as generated by the transducer 23, called field of view.

FIG. 11 illustrates possible ultrasound beam geometry as generated by the transducer 23, called field of view. FIG. 11 includes transducer 23, sensor 27 and axis 28. FIG. 11 also illustrates the ultrasound beam geometry (field of view) generated by the ultrasound sensor of the endovascular probe. When the field of view of the endovascular ultrasound sensors overlaps with the field of view of the transducer (23) energy interference patterns can be detected by both systems.

The interference patterns may be created either a) by direct transfer of energy from one ultrasound sensor to another in the field of view or b) through perturbations in the medium created by one sensor which are detected by the other sensor. For example, the transducer (23) can generate waves in the blood within the vessel where the endovascular probe resides and the endovascular Doppler sensor detects the effect of such waves on blood. The interference, i.e. the transfer of acoustic energy may occur at the central or harmonic frequencies as well as at any other resulting interference frequency which is within the bandwidth of the individual ultrasound sensors.

Interference patterns are detected by the system (20) through the sensor (23). Additionally or alternatively the interference patterns may be detected by the endovascular ultrasound Doppler system.

In one embodiment an ultrasound imaging system like SiteRite or SonoSite is used to image the heart towards the caval-atrial junction. An intravascular device (catheter, wire, and stylet) with a Doppler-capable sensor is inserted through the vasculature and guided towards the heart. The endovascular sensor is connected to a Doppler system which produces signals in accordance with the Doppler frequency shift detected by the sensor. When the endovascular sensor navigates through a vessel, e.g., the SVC and the caval-atrial junction, which is in the field of view of the imaging transducer, the energy emitted by the imaging transducer interferes with the energy emitted by the endovascular probe and the Doppler system connected to the endovascular probe generates signal patterns representative of the interference. Based on these patterns, a user observing the Doppler signals generated by the endovascular probe can infer that the endovascular sensor is situated in the field of view of the imaging probe looking towards the caval-atrial junction. Thus the position of the sensor in the caval-atrial junction is confirmed without having to visualize the catheter in the ultrasound image and without the need of a chest X-ray.

In a further embodiment a Duplex ultrasound imaging system like the Aspen model from Acuson Siemans, Inc. (Mountain View, Calif.) is operated in a Duplex mode: simultaneous imaging and pulsed wave (PW) Doppler or continuous wave (CW) Doppler. The 2D imaging window can show the blood vessel where the endovascular probe is located and the Doppler window shows the Doppler velocity information. In PW mode the sample window is shown over the 2D image. When the endovascular sensor is in the field of view of the CW or in the sample window of the PW mode, a Doppler artifact showing velocity patterns representative of the interference between the two energy elements is shown in the Doppler window. Thus the position of the endovascular sensor is detected.

In a further embodiment a transcutaneous CW or PW pencil probe is used to monitor blood flow in a peripheral blood vessel, e.g., the internal jugular vein. A Doppler-capable endovascular probe is advanced through the internal jugular vein. When the endovascular and the transcutaneous probes are within the field of view of the other, each detects Doppler velocity artifacts representative of the interference patterns. A similar technique applies in the case of multiple endovascular probes.

In a further embodiment the two or more energy elements can be synchronized, such that one emits at a certain delay with respect to the other, e.g., in the receive window of the other. This allows for calculating the distance between probes by knowing the transmit delay and assuming a certain velocity in the anatomy. Thus depth and distance separation/resolution can be achieved. The two energy elements can communicate with each further using coded excitation. If one of the elements generates a certain code pattern, the other one receiving it can identify the presence and location of the transmitting element.

In a further embodiment several locating energy elements can be used to calculate the location of a target energy element by using triangulation. In such a situation the multiple locating elements serve also as reference or as a coordinate system. Alternatively only one locating energy element can be used to locate a target energy element by triangulation if the locating element is moved from place to place in a controlled manner; such that each time the target is located the position is calculated and stored. After a number of such computations taken with the same locating element at different times and from different locations, the position of the target can be reconstructed. In such a case the reference/coordinate system is determined by anatomical landmarks relative to which both the single locating element and the target can be positioned.

2.2 Transducer Placement Concepts

There exist at least two important concepts with respect to optimizing data acquisition from the transducer: radial distance from the inside vessel wall, and axial alignment with respect to blood flow. Each factor influences the quantity and quality of data acquired by the ultrasound transducer.

2.2.1 Radial Distance

Figure 12:
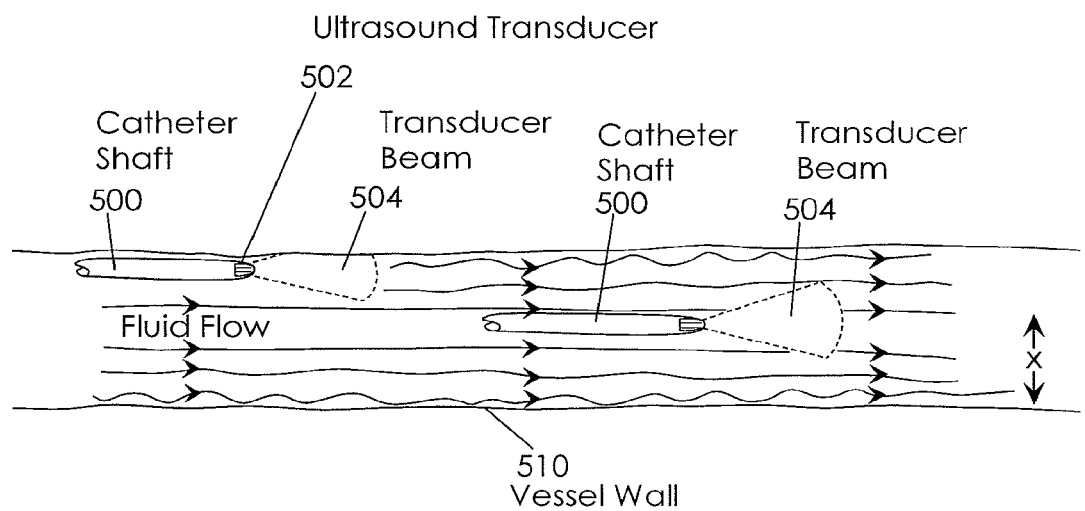

Fluid flowing through the inner diameter of a lumen has different characteristics with respect to flow velocities nearer to the vessel wall than farther towards the center of the lumen: the flow may be more turbulent and slower at the periphery. To take advantage of this known difference thereby avoiding undesirable data acquisition, is the concept of orienting the transducer a minimum distance from the vessel wall as seen in FIG. 12. FIG. 12 includes catheter shaft 500, ultrasound transducer 502, transducer beam 504 and vessel wall 510.

The minimum distance, x, may be determined empirically, or it may be determined by traditional fluid dynamics calculations. This distance may be expressed as a percentage of the lumen diameter, or it may be an absolute number irrespective of lumen dimension.

This application describes several concepts of achieving this radial distance in the following device embodiments.

2.2.2 Axial Alignment

Figure 13A:
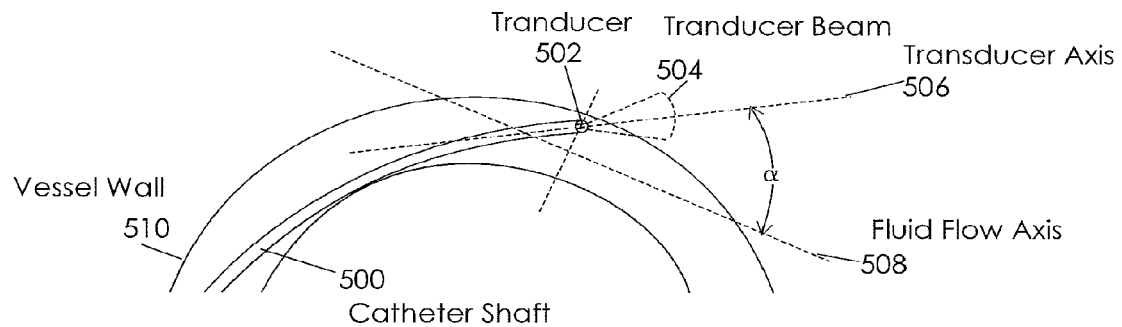
Figure 13B:
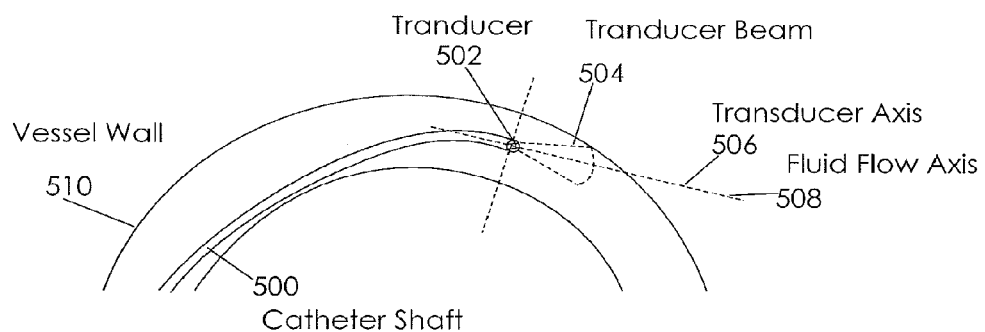

Fluid flowing through the inner diameter of a lumen has a 'preferred' axis of flow that mostly follows the shape of the vessel axis it is flowing within. This preferred axis may be described as that which facilitates the largest magnitude velocity flow vector. Therefore, different characteristics with respect to flow velocities may be found as alignment shifts in an angular sense from the central vector. To take advantage of this known difference thereby avoiding undesirable data acquisition, is the concept of aligning the transducer at an angle from the flow axis as shown in FIGS. 13A and 13B. FIGS. 13A and 13B include vessel wall 510, transducer 502, transducer beam 504, catheter shaft 500, transducer axis 506 and fluid flow axis 508.

The axial offset angle may be expressed as an angular value, $\alpha$, and this may again be empirically determined or be expressed by traditional fluid dynamics calculations. The angle may be expressed as a percentage of vessel curvature, or it may be an absolute irrespective of vessel configuration.

Several general concepts of achieving this axial alignment can be applied to the embodiments described in this application. These embodiments allow for a more flexible portion of the device just proximal to the transducer, and relative to the remaining portion of the catheter, that can be manipulated by the flow in the vessel. Because these sections are able to be biased by fluid flow, the transducer is more likely to find a position in the position of maximum flow.

Figure 14:
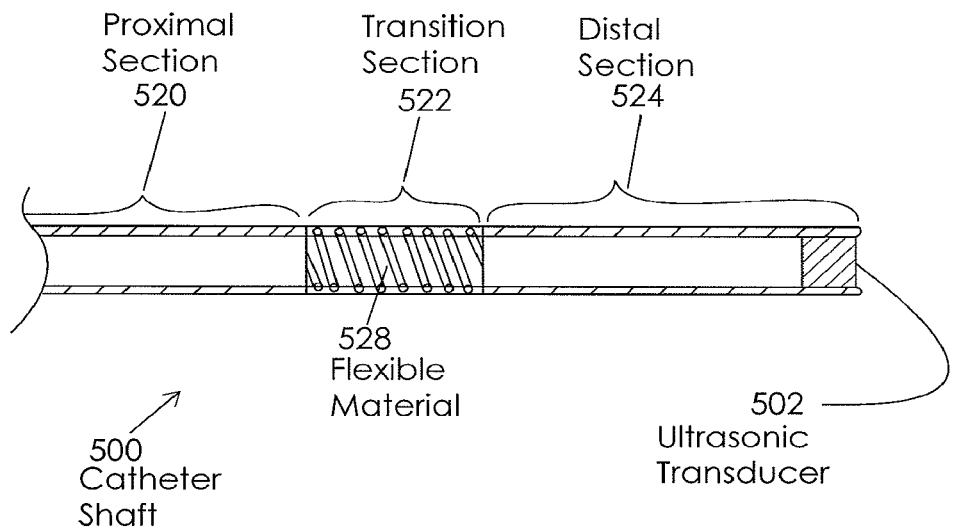

FIG. 14 shows a transition section 522 made of a relatively much more flexible material 528 than what the proximal 520 or distal 524 sections are made of FIG. 14 includes catheter shaft 500 comprising a proximal section 520, transition section 522, distal section 524, flexible material 528 and ultrasonic transducer 502. However to prevent likely kinking of a softer material is the concept of sandwiching a stiffening member to provide maximum kink-resistance yet impact flexibility as little as possible. This may be accomplished with a coil or braid or other axially-involved members. The stiffening material may be metallic or polymeric in nature.

Figure 15:
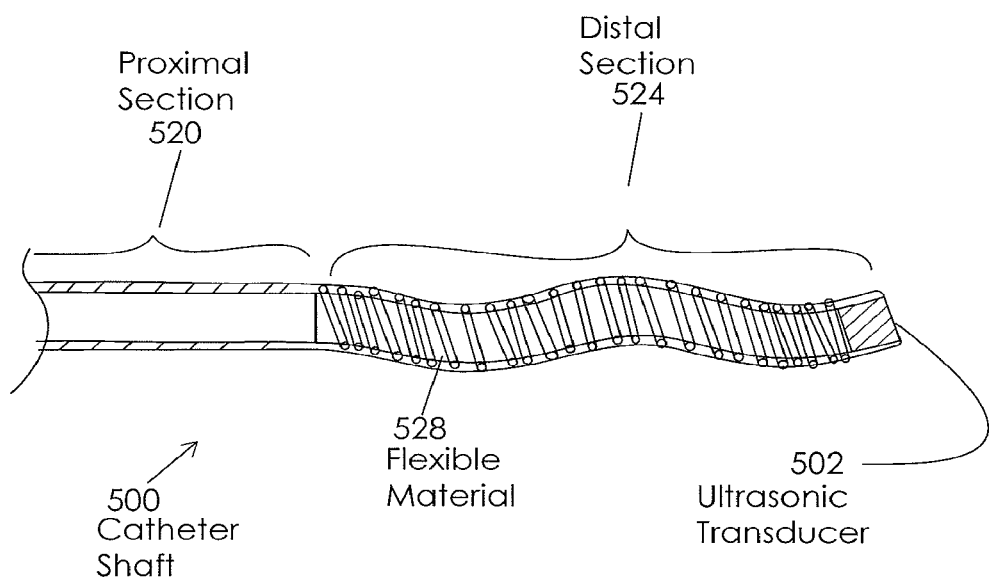
FIG. 15 shows a concept similar to the transition tube, except that the transition tube essentially becomes the entire distal section of the catheter shaft.

FIG. 15 shows a concept similar to the transition tube, except that the transition section essentially becomes the entire distal section 524 of the catheter shaft 500. FIG. 15 includes catheter shaft 500 comprising a proximal section 520, distal section 524, flexible material 528 and ultrasonic transducer 502. Again, this could be reinforced with a coil or braid of a metal or a polymer.

Figure 16:
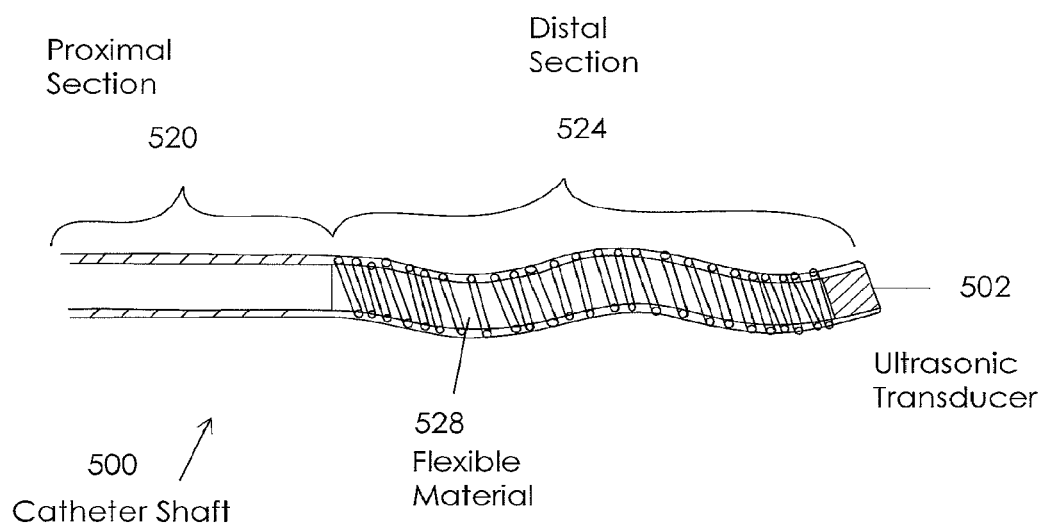
FIG. 16 depicts another concept of axial alignment in that instead of the distal section being tubing, it is made mostly out of a solid flexible material, such as a polymer.

FIG. 16 depicts another concept of axial alignment in that instead of the distal section 524 being tubing, it is made mostly out of a solid flexible material, such as a polymer. FIG. 16 includes catheter shaft 500 comprising a proximal section 520, distal section 524, flexible material 528 and ultrasonic transducer 502.

Figure 17:
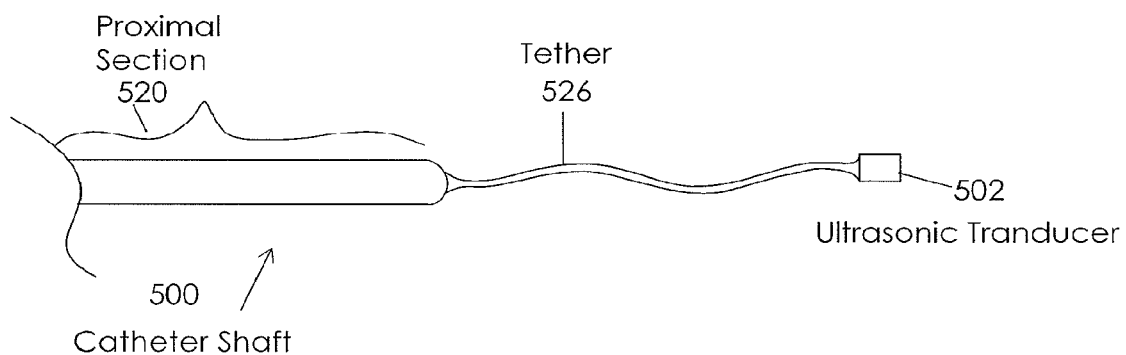
FIG. 17 shows another concept of axial alignment facilitated by a tether component.

FIG. 17 shows another concept of axial alignment facilitated by a tether component. The tether is again very flexible in nature and affixed tightly to the distal end of the proximal shaft. FIG. 17 includes catheter shaft 500 comprising a proximal section 520, tether 526 and ultrasonic transducer 502. The tether can be made of metal or polymer, and the polymer may be reinforced to increase tensile strength.

2.3 Catheter Type

Embodiments of the inventive device include three basic forms: catheter-based, stylet-based & guidewire-based. Some embodiments of the vascular access device may be considered catheter-based, utilizing no removable components. Other embodiments are stylet-based, utilizing a removable component designed to work within the catheter. Other embodiments are guidewire-based, utilizing a removable component designed to work without the catheter. Combinations of the three basic forms are also possible.

Figure 18A:
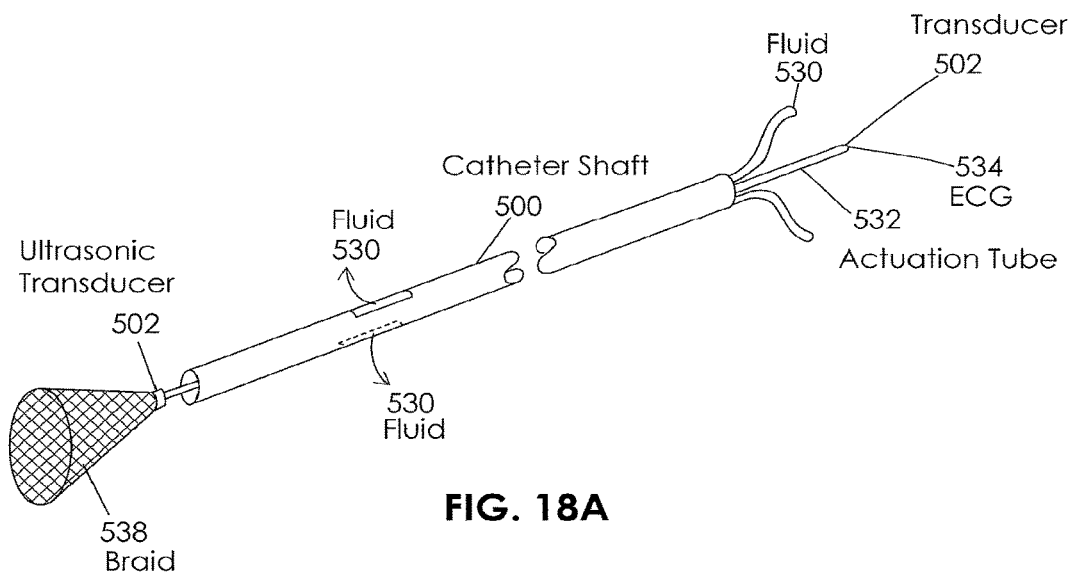
FIGS. 18A and 18B shows a preferred embodiment of two power-injectable lumens each with one side port for fluid delivery adjacent to the closed distal tip.
Figure 18B:
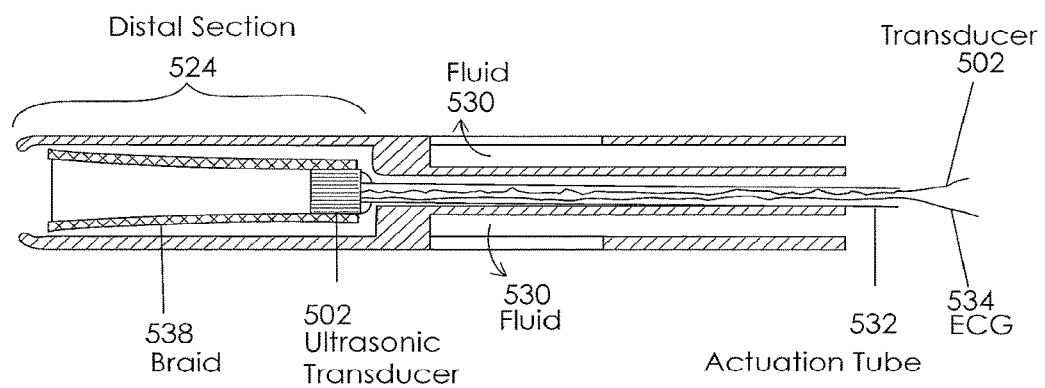

Fluid delivery can be achieved through the catheter shaft in any of the configurations described here within in a number of ways. In a preferred embodiment, the catheter has a closed distal end, is power-injectable and has distal side ports for fluid delivery. These side port(s) can be located along the catheter shaft to comply with pressure and flow rate requirements as well as to provide for optimal access location. Each lumen can have one or more ports and each catheter can have one or more lumens. FIGS. 18A and 18B show preferred embodiments of two power-injectable lumens each with one side port for fluid delivery adjacent to the closed distal tip. In another preferred embodiment, the power-injectable catheter has fluid ports that exit straight out the distal catheter tip. FIG. 18A includes catheter shaft 500, ultrasonic transducer 502, braid 538, fluid 530, ECG 534 and actuation tube 532. FIG. 18B includes a distal section 524, ultrasonic transducer 502, braid 538, fluid 530, ECG 534 and actuation tube 532.

2.3.1 Catheter-Based

Catheter-based devices are "all-in-one" type devices in which no component is completely removable. These remain entirely intact during catheter advancement, drug delivery and subsequent implant dwell time.

Embodiments of the catheter-based inventive device include three basic forms: flow-directed, sensor-directed (passive) and sensor-directed (active). Some embodiments of the catheter-based vascular access device have catheter tips directed mostly by fluid flow within the vasculature. Other embodiments are passively directed by the sensor(s) during catheter advancement through the vasculature. Other embodiments require active manipulation of the catheter tip to acquire and or optimize the data collected by the sensor(s).

2.3.1.1.1 Flow-Directed

In the flow-directed embodiments of the catheter-based vascular access device, placement of the device is 'automatic' in that minimal user interaction is required to position the catheter at the target site. The catheter is positioned 'automatically' by utilizing the blood flowing adjacent to and around it. The sensor(s) are therefore used to verify catheter tip placement at the desired target site as opposed to providing information during advancement to facilitate the advancement itself.

2.3.1.1.1.1 Shaft Surface-Mounted, Balloon Embodiments

In these embodiments, blood flow is utilized by way of a flow-directable member mounted onto the catheter shaft surface that takes the form of a balloon. The balloon is inflated from a proximally-located port by techniques well-known to those skilled in the art of balloon catheters.

Figure 19:
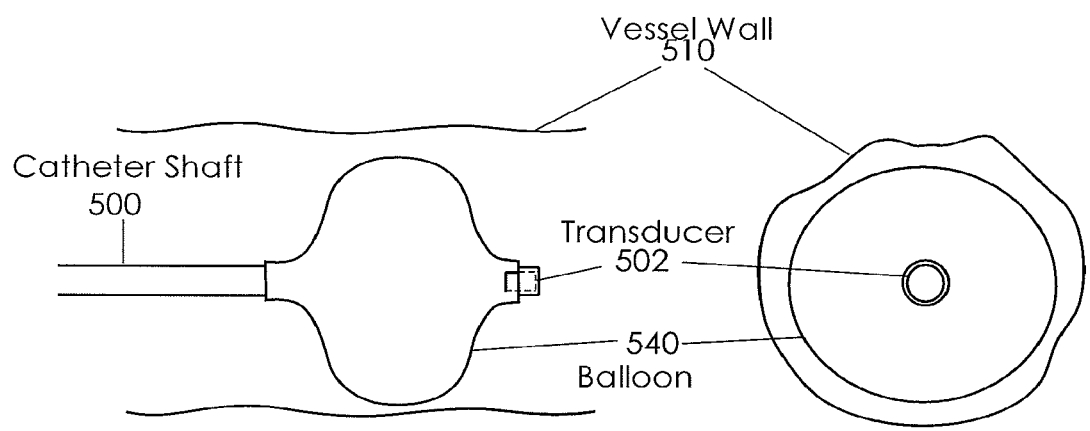
FIG. 19 is a side view of a shaft surface-mounted balloon embodiment.
Figure 20:
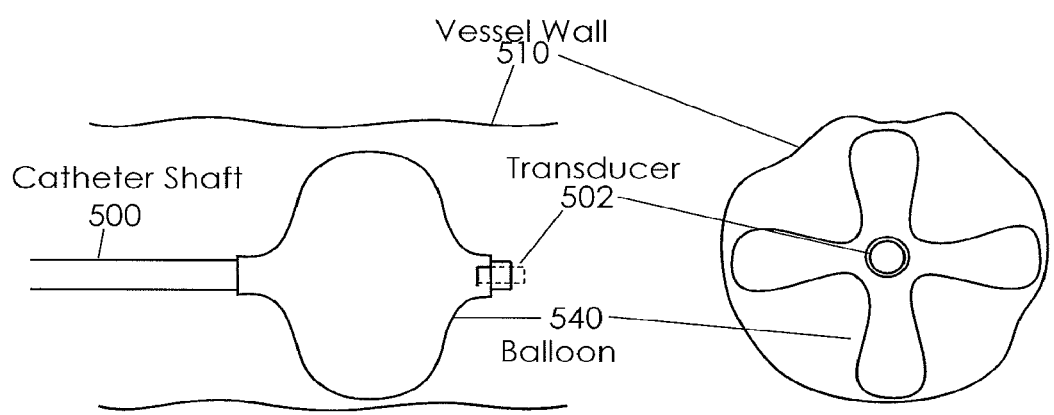
FIG. 20 illustrates a profiled balloon is mounted to the catheter shaft surface.

FIG. 19 is a side view of a shaft surface-mounted balloon embodiment. FIG. 19 includes vessel wall 510, catheter shaft 500, transducer 502 and balloon 540. The balloon 540 material, either compliant or non-compliant, is mounted onto the catheter shaft 500, and the transducer 502 is left at the distal tip. In one embodiment, the balloon 540 is considered symmetrical in both the axial and radial directions. Balloon embodiments may impede blood flow around the transducer causing a signal substandard to that which could otherwise be obtained were more blood allowed to flow around and adjacent to the transducer. In another embodiment, a profiled balloon 540 is mounted to the catheter shaft 500 surface, as shown in the side and end views of FIG. 20. FIG. 20 includes vessel wall 510, catheter shaft 500, transducer 502 and balloon 540. It is believed that the profiled shape facilitates blood flow near the transducer 502.

Figure 21:
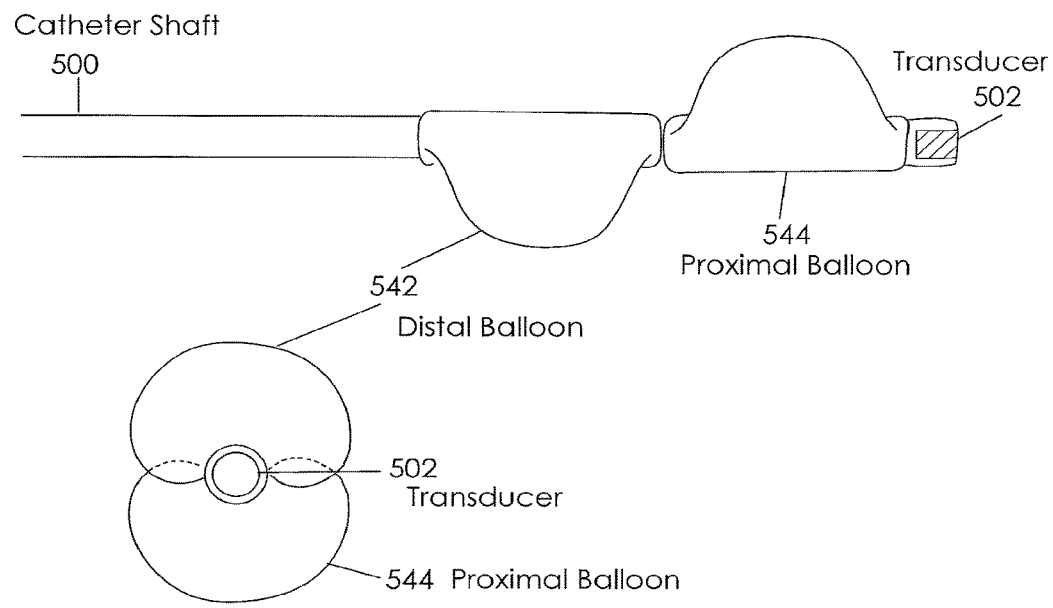
FIG. 21 shows an alternate embodiment of a catheter shaft surface-mounted balloon embodiment with 2 radially asymmetric balloons placed on the catheter shaft.

FIG. 21 shows an alternate embodiment of a catheter shaft 500 surface-mounted balloon embodiment with 2 radially asymmetric balloons placed on the catheter shaft 500. FIG. 21 includes catheter shaft 500, transducer 502 and proximal balloon 540 and distal balloon 542. From a radial perspective, the flow is circumferentially captured to maximize the use of a balloon 542 or 544 as a sail. The balloons 542 and 544 are staggered from an axial point of view to facilitate more blood flow around and adjacent to the transducer. While two balloons are shown, more or less may be used.

Figure 22A:
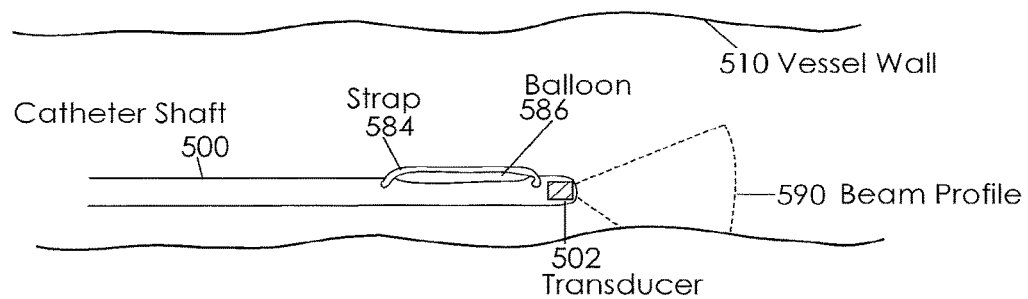
FIGS. 22A, 22B and 22C depict embodiments in which a balloon is mounted onto a catheter shaft such that less than 180 deg, measured circumferentially with respect to the catheter shaft, is covered by the balloon material.
Figure 22B:
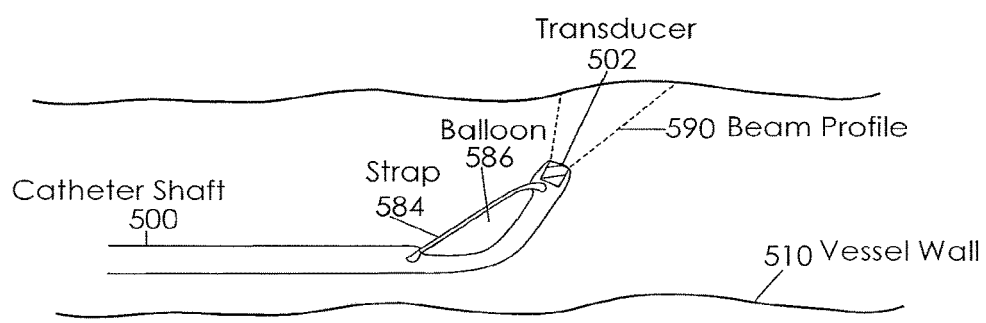
Figure 22C:
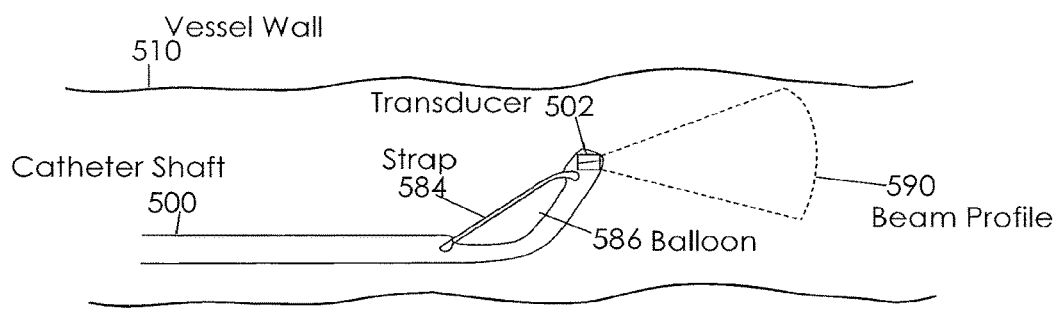

FIGS. 22A, 22B, and 22C depict embodiments in which a balloon 586 is mounted onto a catheter shaft 500 such that less than 180 degree, measured circumferentially with respect to the catheter shaft 500, is covered by the balloon material. FIGS. 22A, 22B and 22C include vessel wall 510, catheter shaft 500, transducer 502, balloon 586, strap 584 and beam profile 590. A non-distensible member, i.e. a 'strap' 584, is placed over the balloon 586 in an axial direction to facilitate mostly catheter 500 shaft bending and minimally balloon 586 inflation. The assembly is straight when the balloon 586 is uninflated. Once inflation is complete, the distal catheter 500 shaft is deflected and becomes a flow-directable member, thereby moving the catheter tip into the blood flow facilitating movement through the blood vessel.

2.3.1.1.1.2 Shaft Surface-Mounted, Non-Balloon Embodiments

In these embodiments, blood flow is utilized not by balloons, but by flow-directable members mounted onto the catheter shaft surface and actuated from the proximal handle via several methods well-known to those skilled in the art of catheter actuation, i.e.: push/pull tube or wire, outer diameter sheath, etc.

Figure 23:
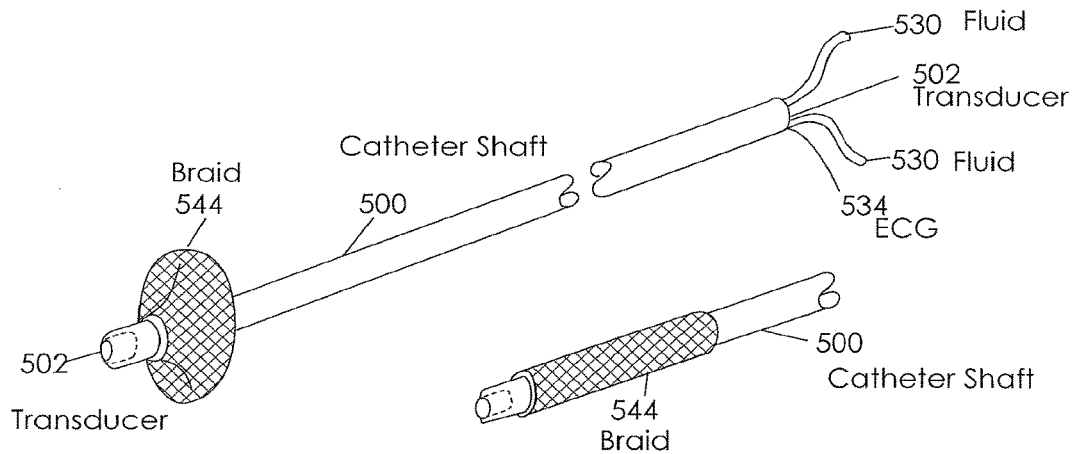
FIG. 23 shows an embodiment of the catheter-based flow-directed vascular access device in which a flow-directable component.

FIG. 23 shows an embodiment of the catheter-based flow-directed vascular access device in which a flow-directable component, shown in the figure as an axially-compressed braid 544, is mounted directly on the exterior surface of the catheter 500 shaft. FIG. 23 includes catheter shaft 500, ultrasonic transducer 502, braid 544, fluid 530, ECG 534. In one embodiment, the braid 544 component is manufactured in such a way such that the radial expansion of the fibers is maximized. The braid 544 material can be metallic or polymer-based. The amount of flow captured by the braid 544 can be varied depending upon the number of filaments used or the diameter of same.

Figure 24:
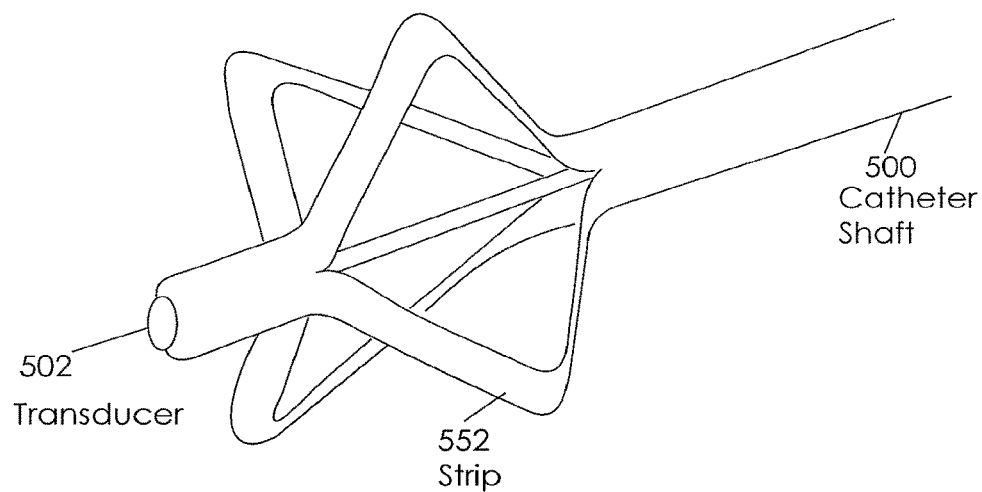
FIG. 24 shows proximally-actuated and shaft surface-mounted embodiment in which the catheter shaft itself is split such that movement of the distal tip in a proximal direction will cause the shaft to splay outward thereby creating a flow-directable component.

FIG. 24 shows another proximally-actuated and shaft surface-mounted embodiment in which the catheter 500 shaft itself is split such that movement of the distal tip in a proximal direction will cause the shaft 500 to splay outward thereby creating a flow-directable component. FIG. 24 includes catheter shaft 500, transducer 502, strip 552.

The flow-directability of any of the configurations described in the previous figures can be augmented by placing a covering of some sort to capture more of the flow. The amount captured may be fine-tuned by varying such features as the density (i.e.: placing perforations in the material), or flexibility as well.

Figure 25:
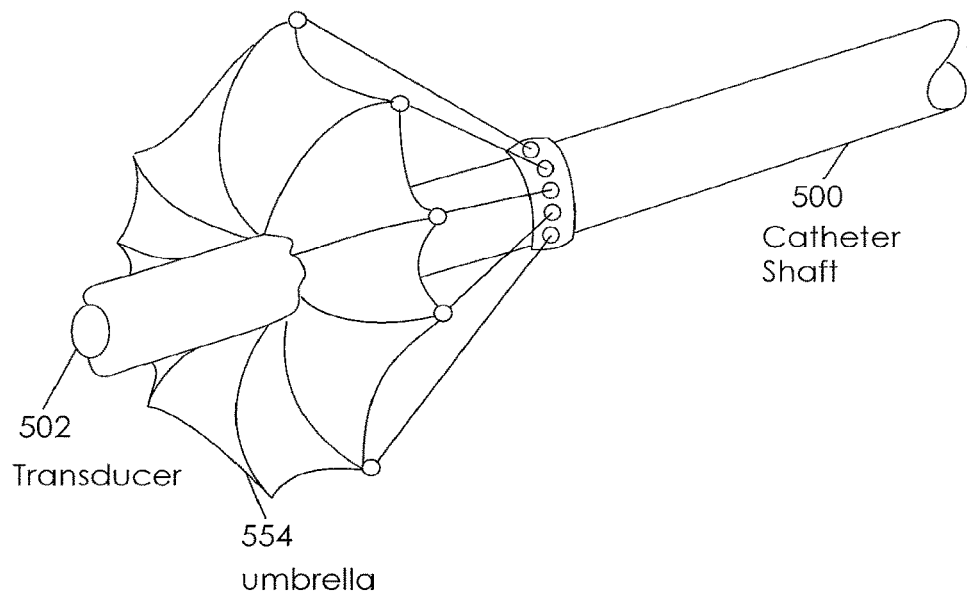
FIG. 25 shows yet another proximally-actuated and shaft surface-mounted embodiment in which an umbrella-like component acts as the flow-directable member.

FIG. 25 shows yet another proximally-actuated and shaft surface-mounted embodiment in which an umbrella-like component acts as the flow-directable member. FIG. 25 includes catheter shaft 500, transducer 502, umbrella 554.

2.3.1.1.2 Tip-Mounted Embodiments

In these embodiments, blood flow is utilized by way of a flow-directable member mounted directly onto the catheter tip instead of the shaft surface.

Any of the configurations shown in FIGS. 15, 16 and 17 as alignment examples are also candidates for embodiments relating to tip-mounting, with no retraction. The concept is that the lighter the transducer assembly is, the more likely it will be to float in the vasculature.

2.3.1.1.2.1 Distally-Housed Embodiments

In these embodiments, blood flow is again utilized by flow-directable members, but instead of being mounted onto the catheter shaft surface, they are mounted to an internally-based actuation tube that is actuated from the proximal handle via methods well-known to those skilled in the art of catheter actuation. Once the flow-directable member is no longer needed, it may be retracted into the distal catheter shaft.

FIG. 18A shows a perspective view of an embodiment of the flow-directed catheter-based vascular access device in which a flow-directable component is 'housed' inside the distal end of a catheter shaft. In this particular embodiment, the flow-directable component is an open-ended braid shaped similar to the 'Lacrosse' basket. It is predisposed to an expanded or open configuration, and collapses when pulled inside the distal catheter housing. The transducer is mounted within the braid, and both are mounted onto an actuation tube. The actuation tube houses the transducer wire and the ECG wire as well. The braid and actuation tube may be made entirely out of a polymer, entirely out of a metal or a combination of both. If the tube was made of a conductive material or encapsulated a conductor of some sort, it could double as the ECG lead as well. The actuation tube is actuated from the proximal catheter handle.

In this particular embodiment, the braid is designed such that it captures the majority of blood flowing through the lumen, in order to facilitate movement of the device through the vasculature, yet still allows enough blood to flow through it to provide data for the transducer to utilize. This concept may facilitate device movement in the correct direction (with flow), averting the need to influence or steer the tip. Then as the need for influencing or steering the tip diminishes, the importance of catheter shaft torque-ability is also reduced. This in turn facilitates the use of a softer, more flexible catheter shaft compliant to the vessel and more comfortable to the patient.

FIG. 18B shows a close-up cross-sectional view of the distal catheter shaft of FIG. 18A. The catheter shaft is made of a proximal and distal section. The proximal section is made up of at least 3 lumens: two for separate fluid delivery ports and one for the actuation tube. The distal section may be a single lumen tubing that 'houses' the collapsed braid.

By relocating the fluid ports just proximal of the distal 'house' (as shown in FIG. 18B), precious catheter 'real estate' is optimized: the distal section is reserved for a bulky flow-directable member, while the slimmer actuation member follows the fluid lumens back to the proximal handle.

The 'Lacrosse' braid design may be made by turning a simple braided tube back onto itself. In this configuration, the very distal or most expanded end may be difficult to retract into the housing in terms of the pull force required. To minimize this force, the very distal end may be asymmetrical in nature so that the entire circumference isn't pulled into the distal house concurrently.

Figure 26:
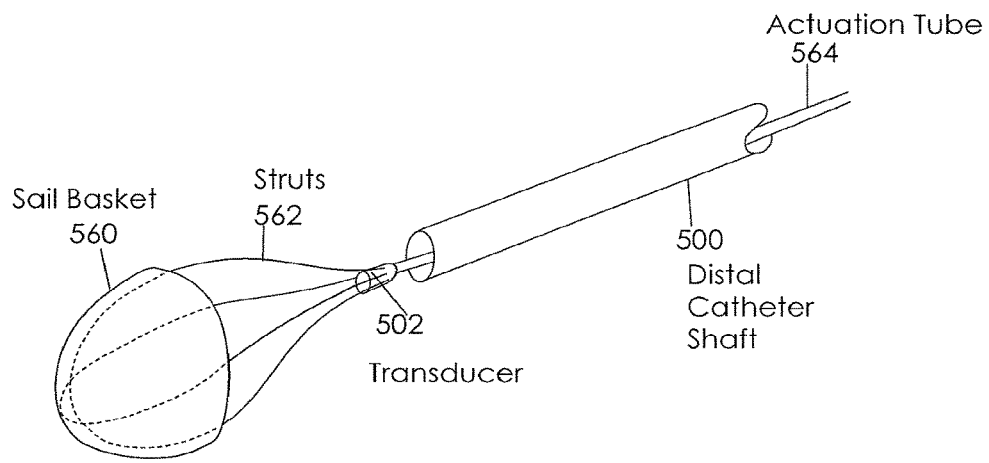
FIG. 26 illustrates that the flow-directable member can be made up of self-expanding struts covered by a sail material.

Alternatively, the flow-directable member can be made up of self-expanding struts covered by a sail material, such as a biocompatible flexible material, e.g., ePTFE or other suitable biocompatible sheet, as shown in FIG. 26. FIG. 26 includes distal catheter shaft 500, transducer 502, struts 562, sail basket 560 and actuation tube 564.

Figure 27:
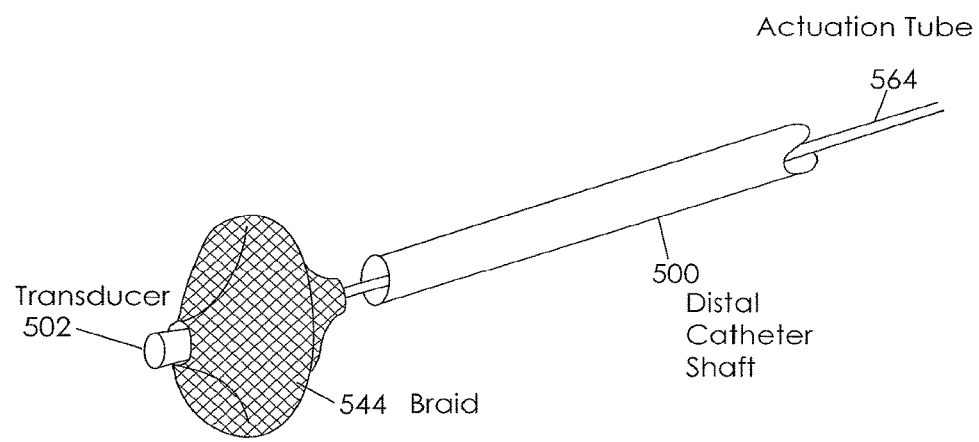
FIG. 27 shows another perspective view of another embodiment of a distally-housed flow-directed device that uses an axially-compressed braid as a flow-directable member.

FIG. 27 shows another perspective view of another embodiment of a distally-housed flow-directed device that uses an axially-compressed braid as a flow-directable member. FIG. 27 includes distal catheter shaft 500, transducer 502, braid 544 and actuation tube 564.

Figure 28:
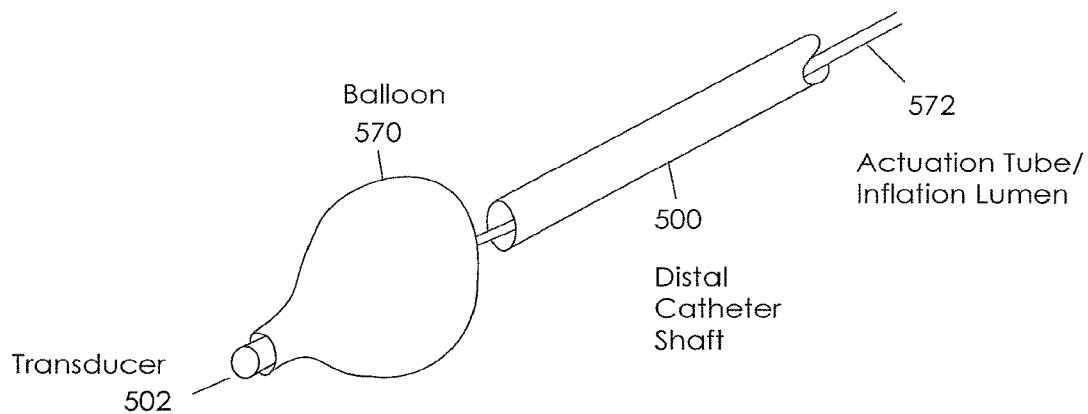
FIG. 28 shows a perspective view of another embodiment of a distally-housed flow-directed device that uses a balloon as a flow-directable member.

FIG. 28 shows a perspective view of another embodiment of a distally-housed flow-directed device that uses a balloon as a flow-directable member. FIG. 28 includes distal catheter shaft 500, balloon 570, transducer 502 and actuation tube 572. In this concept, the distal catheter section may not facilitate collapse of the flow-directable member, as in the case of the other described embodiments, it may simply house the flow-directable member.

In any of the described configurations, the transducer may be mounted on the flow-directed component in such a way to optimize the signal acquired, in other words, distal to the component or so that the transducer signal is not attenuated by the component's presence.

Figure 29:
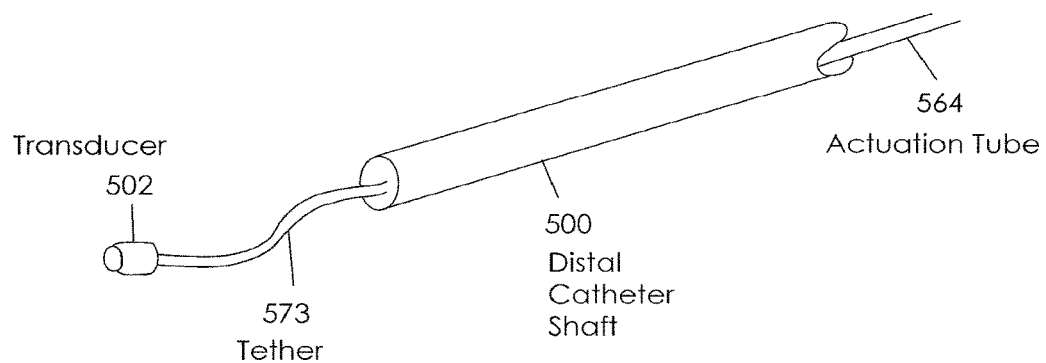
FIG. 29 illustrates a transducer tether embodiment.

Alternatively, the transducer could be mounted on a tether (as previously described in FIG. 20). FIG. 29 illustrates a transducer tether embodiment. FIG. 29 includes distal catheter shaft 500, transducer 502, tether 573 and actuation tube 564.

2.3.1.2 Sensor-Directed (Passive)

In the passive sensor-directed embodiments of the catheter-based vascular access devices, placement of the device is facilitated by data received passively from the sensor(s) located on the catheter shaft during catheter advancement. User interaction is required to advance the catheter according to the data received and displayed by the sensor(s), and the sensor(s) are again used to verify catheter tip placement at the desired target site. However, no user interaction is required to optimize the sensor(s) information received in these embodiments: this function is passively accomplished by virtue of the catheter design.

To accomplish passive acquisition of sensor data or data acquisition that does not require user interaction to facilitate either its basic acquisition or optimization of, the distal catheter design needs to accomplish two things. First, the distal catheter design needs to facilitate placement of the sensor a minimum distance, when measured radially, from the vessel wall to insure that enough flow, as well as steady flow is experienced in the area directly adjacent to the sensor (as described in section 2.3.1). Second, the distal catheter design needs to facilitate axial alignment of the ultrasound sensor with respect to the flow of blood adjacent to it (as described in section 2.3.2).

Shaft Surface-Mounted Balloon Embodiments

In these embodiments, radial distance from the vessel wall and/or axial alignment is achieved by a balloon member mounted onto the catheter shaft. The balloon is inflated from a proximally-located port by techniques well-known to those skilled in the art of balloon catheters.

FIGS. 19, 20 and 21, as previously described, are examples of shaft-mounted balloon embodiments that could facilitate radial distance from the vessel wall.

Figure 30A:
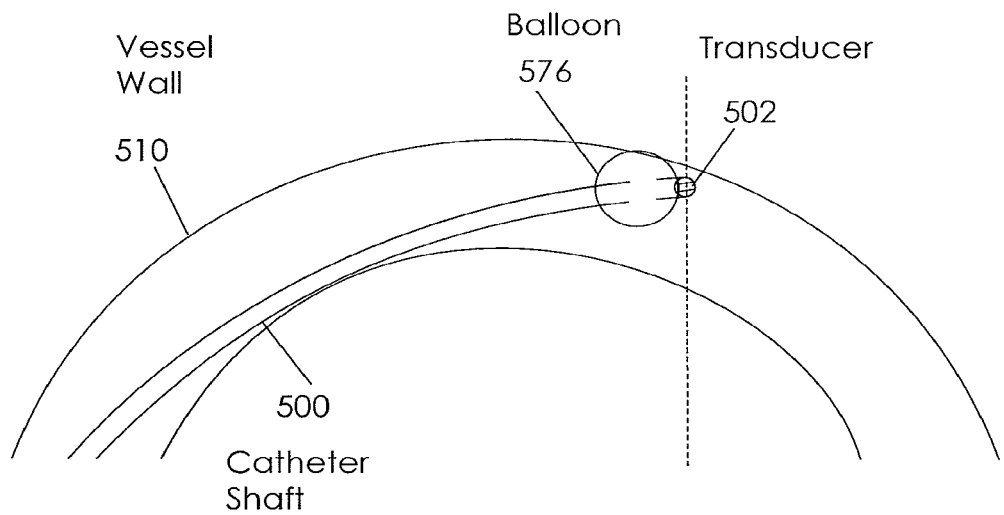
FIG. 30A illustrated a sensor may still be positioned against the wall even when the balloon is inflated and when the balloon is mounted too far proximal on the catheter shaft with respect to the sensor location.
Figure 30B:
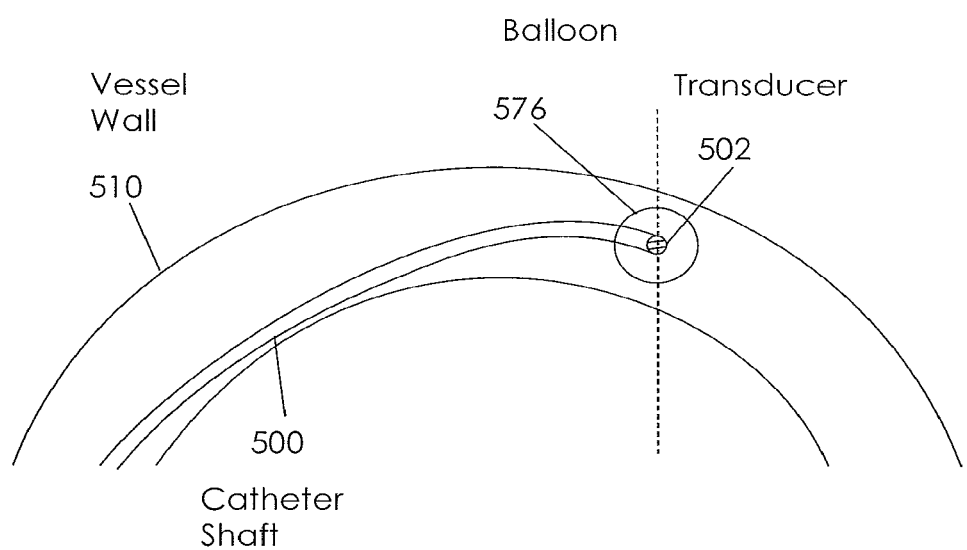
FIG. 30B illustrates one of the ways in which a balloon embodiment can address this issue is by being mounted as far distal, with respect to the sensor, as possible.

One of the challenges in achieving the desired radial distance with the embodiments shown in FIGS. 19 and 20 is when the tip is adjacent to the vessel wall 510 while in a curve. As illustrated in FIG. 30A, when the balloon 576 is mounted too far proximal on the catheter shaft 500 with respect to the sensor location, the sensor may still be positioned against the wall 510 even when the balloon is inflated. One of the ways in which a balloon embodiment can address this issue is by being mounted as far distal, with respect to the sensor, as possible, as shown in FIG. 30B. Both FIGS. 30A and 30B include catheter shaft 500, transducer 502, balloon 576, vessel wall 510.

Figure 31:
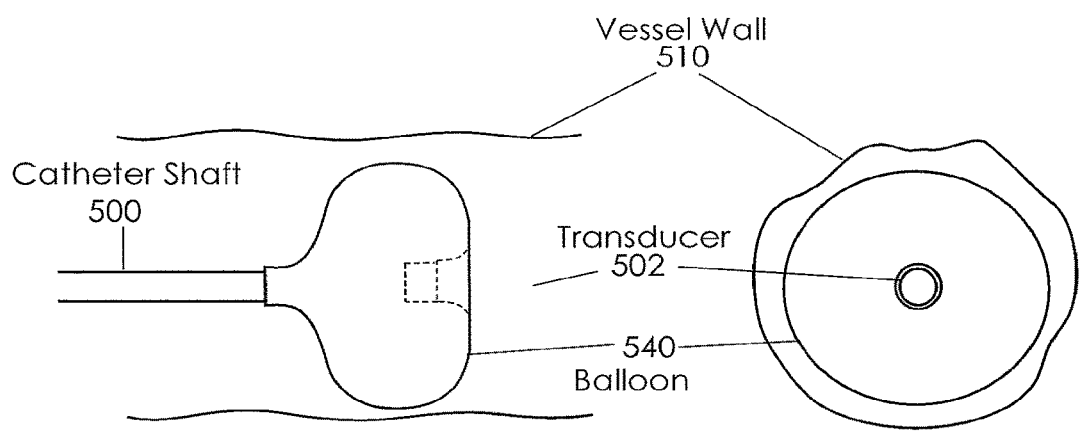
FIG. 31 shows a shaft surface-mounted balloon embodiment, building on the idea described in FIGS. 30A and 30B.

FIG. 31 shows a shaft surface-mounted balloon embodiment, building on the idea described in FIGS. 30A and 30B, in which the balloon 540 is mounted on the catheter shaft 500 so that it extends distally beyond the location of the sensor.

Figure 32:
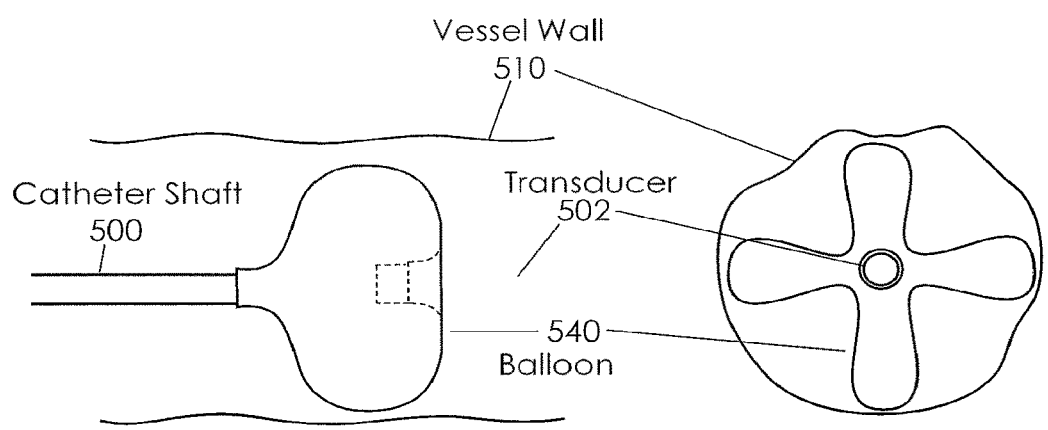
FIG. 32 illustrates a profiled balloon when a flow restriction becomes an issue and prevent the sensor from acquiring a signal.

Should flow restriction again become an issue and prevent the sensor from acquiring a signal, as previously described, a profiled balloon could be used as shown in FIG. 32.

Figure 33:
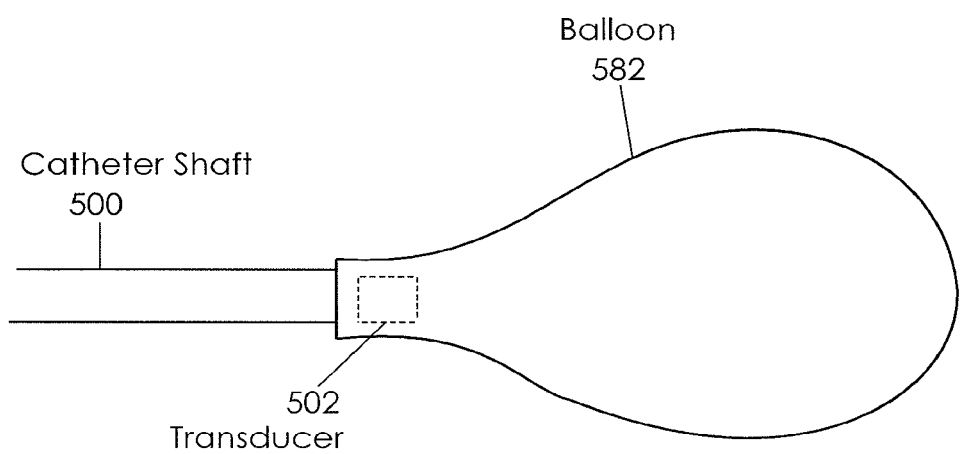
FIG. 33 illustrated another balloon embodiment may include a balloon mounted entirely on the distal catheter tip, completely covering the sensor.

Another balloon embodiment may include a balloon mounted entirely on the distal catheter tip, completely covering the sensor, as shown in FIG. 33. In this embodiment, the balloon 582 would need to be filled with a medium transparent to the ultrasound frequencies of the sensor used, i.e.: saline or water.

Further, any of the balloon embodiments could offer adjustable radial distances depending upon the amount of fluid injected into the proximal port and the resulting amount of balloon inflation.

Shaft Surface-Mounted, Non-Balloon Embodiments

In these embodiments, radial distance from the vessel wall and/or axial alignment is achieved by radially expanding members mounted onto the catheter shaft surface and actuated from the proximal handle via several methods well-known to those skilled in the art of catheter actuation, i.e.: push/pull tube or wire, outer diameter sheath, etc.

FIGS. 23, 24 and 25, previously described, show embodiments of catheter-based and sensor-directed vascular access devices in which shaft surface-mounted components facilitating passive data acquisition by the sensor provide a circumferential radial offset of the catheter tip with respect to the vessel wall.

Distally-Housed Embodiments

In these embodiments, radial distance from the vessel wall and/or axial alignment is achieved by radially expanding members mounted to an internally-based actuation tube that is actuated from the proximal handle via methods well-known to those skilled in the art of catheter actuation. Once the radially expanding member is no longer needed, it may be retracted into the distal catheter shaft.

The embodiments shown in FIGS. 18A, 26, 27 and 28, previously described, show embodiments of the catheter-based and flow-directed vascular access devices, however these same embodiments can be used for the passive sensor-directed embodiments as well. The same expanding members may facilitate radial expansion and axial alignment for passive data acquisition.

As previously described, relocating the fluid ports just proximal of the distal 'house' conserves precious catheter 'real estate': the distal section is reserved for a bulky flow-directable member, while the slimmer actuation member follows the fluid lumens back to the proximal handle.

2.3.1.3 Sensor-Directed, Active

In the active sensor-directed embodiments of the catheter-based vascular access devices, placement of the device is facilitated by data received from the sensor(s) located on the catheter shaft during catheter advancement by actively manipulating the catheter shaft and subsequently the catheter tip. User interaction is required to advance the catheter according to the data received and displayed by the sensor(s), and the sensor(s) are again used to verify catheter tip placement at the desired target site. User interaction is also required to optimize the sensor(s) information received in these embodiments as this function cannot be accomplished by virtue of the catheter design alone.

The distal catheter design may be modified to accomplish active acquisition of sensor data, or data acquisition that utilizes user interaction to facilitate either its basic acquisition or optimization. The distal catheter design may facilitate placement of the sensor a minimum distance, when measured radially, from the vessel wall to insure that enough flow, as well as steady flow is experienced in the area directly adjacent to the sensor (as described in section 2.3.1). The distal catheter design may facilitate axial alignment of the ultrasound sensor with respect to the flow of blood adjacent to it (as described in section 2.3.2). Further, the distal catheter design may facilitate radial distance and axial alignment on demand, by the user.

2.3.1.3.1 Shaft Surface-Mounted, Balloon Embodiments

In these embodiments, radial distance from the vessel wall and/or axial alignment is achieved by a balloon member mounted onto the catheter shaft. The balloon is inflated from a proximally-located port by techniques well-known to those skilled in the art of balloon catheters.

FIGS. 22A, 22B and 22C, previously described, depict embodiments in which the distal catheter shaft is deflected and the sensor is moved away from the vessel wall. This movement may not only optimize the data the ultrasound sensor is to acquire, but facilitate the very acquisition of that data in the first place. Furthermore, to facilitate sensor axis alignment to the blood flow once tip actuation has taken place, the sensor can be mounted in an off-axis or skewed manner. The angular difference depends on the amount of catheter bend created by balloon inflation, and this can be pre-determined. FIG. 22A shows the un-inflated non-skewed transducer mounted embodiment, and likely the resulting beam profile. FIG. 22B shows the inflated state of the device and the resultant improved transducer position away from the vessel wall; however an unimproved beam profile may still remain. FIG. 22C shows the inflated state of the device couple with an off-axis mounted transducer that provides for a more optimum beam profile.

FIG. 21, previously described, shows at least 2 'staggered' balloons that facilitate flow around the catheter shaft, however were just one balloon placed and further inflated, it could provide a means by which the user could actively reposition the catheter with respect to the vessel wall as needed during catheter advancement and subsequent placement at the target site.

2.3.1.3.2 Shaft Surface-Mounted, Non-Balloon Embodiments

In these embodiments, radial distance from the vessel wall and/or axial alignment is achieved by radially expanding members mounted onto the catheter shaft surface and actuated from the proximal handle via several methods well-known to those skilled in the art of catheter actuation, i.e.: push/pull tube or wire, outer diameter sheath, etc.

FIGS. 23, 24 and 25, previously described, show embodiments of catheter-based and sensor-directed vascular access devices in which shaft surface-mounted components facilitate passive data acquisition by the sensor by providing a circumferential radial offset of the catheter tip with respect to the vessel wall. However, were these members asymmetrical with respect to the radial direction, they may also facilitate the ability to manually offset the distal tip from a proximal actuation thereby creating active direction to the sensor.

2.3.1.3.3 Distally-Housed Embodiments

In these embodiments, radial distance from the vessel wall and/or axial alignment is achieved by radially expanding members mounted to an internally-based actuation tube that is actuated from the proximal handle via methods well-known to those skilled in the art of catheter actuation. Once the radially expanding member is no longer needed, it may be retracted into the distal catheter shaft.

FIGS. 18A, 26, 27 and 28, previously described, show embodiments of catheter-based and flow-directed vascular access devices in which distally-housed components facilitate passive data acquisition by the sensor by providing a circumferential radial offset of the catheter tip with respect to the vessel wall. However, were these members asymmetrical with respect to the radial direction, they may also facilitate the ability to manually offset the distal tip from a proximal actuation, thereby creating active direction to the sensor.

As previously described, relocating the fluid ports just proximal of the distal 'house' conserves precious catheter 'real estate': the distal section is reserved for a bulky flow-directable member, while the slimmer actuation member follows the fluid lumens back to the proximal handle.

2.3.1.3.4 Steerable Embodiments

In these embodiments, radial distance from the vessel wall is achieved by a steerable distal catheter section actuatable from the proximal handle by techniques well-known to those skilled in the art of steerable catheters, i.e.: a distally-mounted pull-wire. Once tip deflection is no longer needed, it may be relaxed into a straight position. It is to be appreciated that steering techniques may be used to provide desired transducer orientation within the vessel.

Figure 34A:
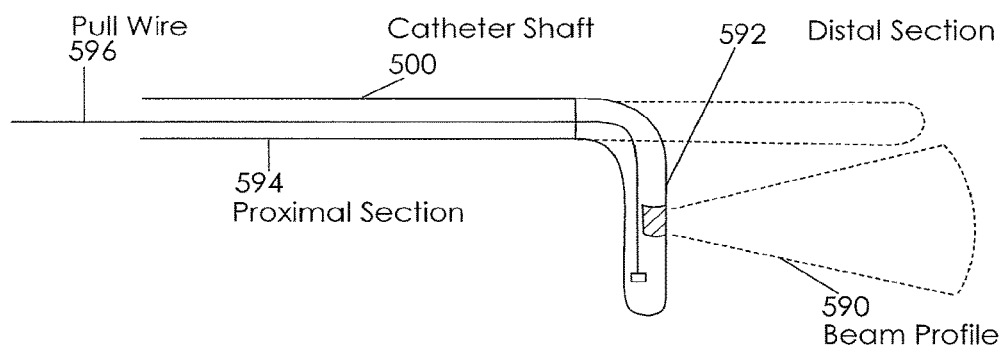
FIGS. 34A and 34B show a catheter-based vascular access device in which the proximal section is made of a relatively stiffer material when compared to the distal section to facilitate the columnar strength required during distal steering actuation.
Figure 34B:
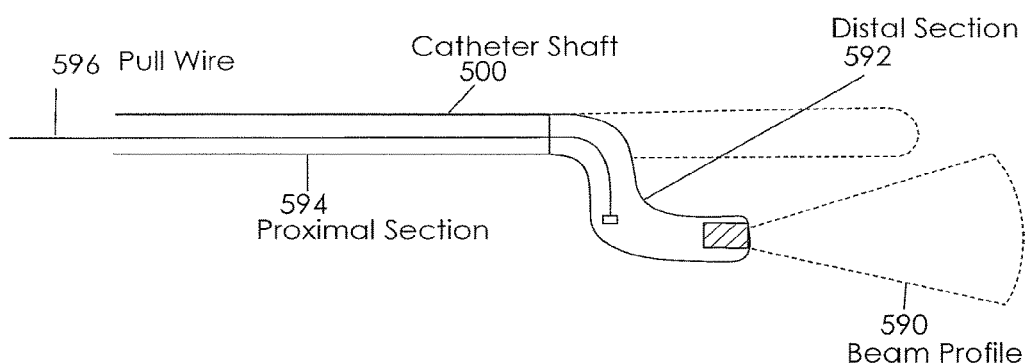

FIGS. 34A and 34B show a catheter-based vascular access device in which the proximal section is made of a relatively stiffer material when compared to the distal section to facilitate the columnar strength required during distal steering actuation. FIGS. 34A and 34B include catheter shaft 500, proximal section 594, pull wire 596, distal section 592 and beam profile 590. The pull-wire 596 would be affixed to the distal section 592, either proximal or distal to the sensor. The sensor could be mounted off-center with respect to the catheter shaft 500, any where from about 0 degrees to about 180 degrees, depending upon the angle created by the pull-wire 596, as shown in FIG. 34A, or the sensor could remain axially-oriented while the pull-wire 596 is affixed to the distal catheter shaft 500 in a axially-aligned position, as shown in FIG. 34B. Alternatively, the sensor could be positioned such that it faces a backward direction as well.

2.3.2 Stylet-Based

Stylet-based devices allow the catheter to have characteristics it normally wouldn't have without the stylet, i.e.: stiffness or shape. Moreover, the stylet affords that catheter the additional benefit of having these characteristics at certain times, only when needed.

An additional benefit of the stylet-based device is that a fluid lumen may be utilized for passage of the stylet since the stylet will be removed once the catheter has been appropriately placed. Since a lumen would not need to be dedicated to sensor(s) or other functionality, precious 'real estate' of an approximately 5 F or smaller catheter is optimized. The stylet embodiments in the following sections can be used both with fluid lumens that exit out the distal tip or out through side slots.

Embodiments of the inventive device include two basic forms. Some embodiments of the stylet-based vascular access device are passively directed by the sensor(s) during stylet/catheter advancement through the vasculature. Other embodiments require active manipulation of the stylet/catheter tip to acquire and or optimize the data collected by the sensor(s).

2.3.2.1 Sensor-Directed, Passive

In the passive sensor-directed embodiments of the stylet-based vascular access devices, placement of the device is facilitated by data received passively from the sensor(s) located on either the catheter or stylet shaft during catheter advancement. User interaction is required to advance the catheter according to the data received and displayed by the sensor(s), and the sensor(s) are again used to verify catheter tip placement at the desired target site. However, no user interaction is required to optimize the sensor(s) information received in these embodiments: this function is passively accomplished by virtue of the stylet/catheter design.

The stylet design may be modified to accomplish passive acquisition of sensor data, or data acquisition that does not require user interaction to facilitate either its basic acquisition or optimization. The stylet may facilitate placement of the sensor a minimum distance, when measured radially, from the vessel wall to insure that enough flow, as well as steady flow is experienced in the area directly adjacent to the sensor (as described in section 2.3.1). The stylet may also facilitate axial alignment of the ultrasound sensor with respect to the flow of blood adjacent to it (as described in section 2.3.2).

Figure 35A:
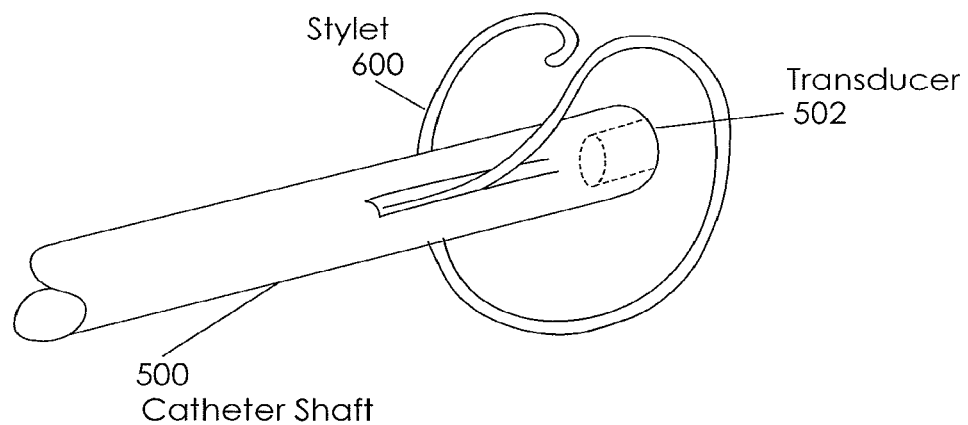
FIGS. 35A and 35B show an embodiment of a sensor-directed vascular access device in which a mostly circular pre-formed stylet is advanced through a catheter lumen to create a passive mechanism by which transducer position is maintained so that data can be acquired.
Figure 35B:
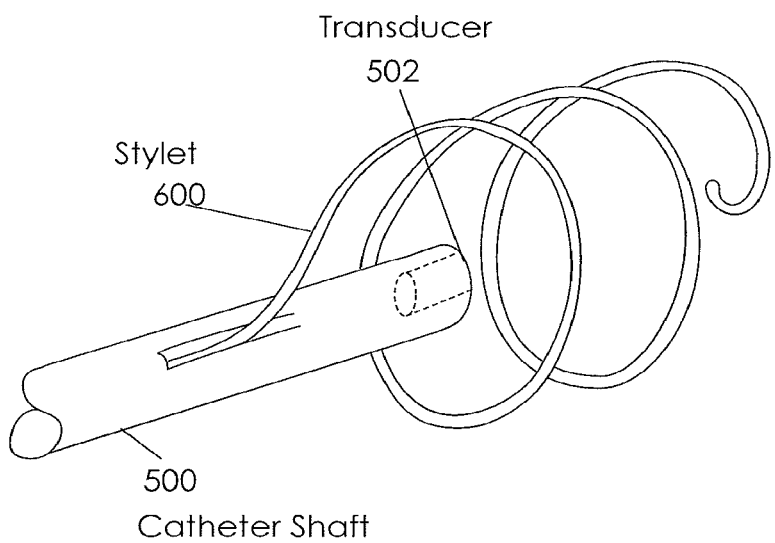

FIGS. 35A and 35B show an embodiment of a sensor-directed vascular access device in which a mostly circular pre-formed stylet is advanced through a catheter lumen to create a passive mechanism by which transducer position is maintained so that data can be acquired. This is achieved via the stylet's 600 exit out a distally-placed port, either out the side of the catheter shaft 500 or directly out the tip. FIGS. 35A and 35B include catheter shaft 500, transducer 502 and stylet 600. FIG. 35A shows a single loop, similar to a 'halo' in shape exiting a side port and FIG. 35B shows multiple loops, similar to a 'pig-tail', also exiting out a side port. Like a pig-tail, the loops diameters can get smaller, remain the same, or get larger as one moves distally on the stylet body.

Figure 36A:
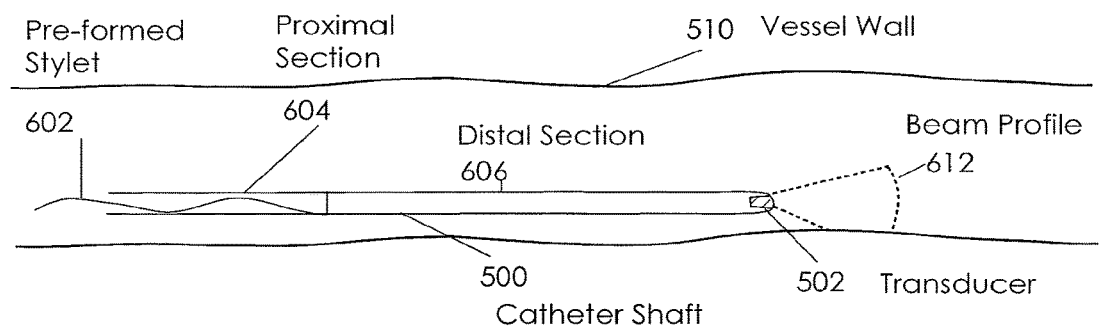
FIGS. 36A and 36B show another embodiment utilizing a pre-formed stylet to shape the catheter shaft itself without exiting a side port.
Figure 36B:
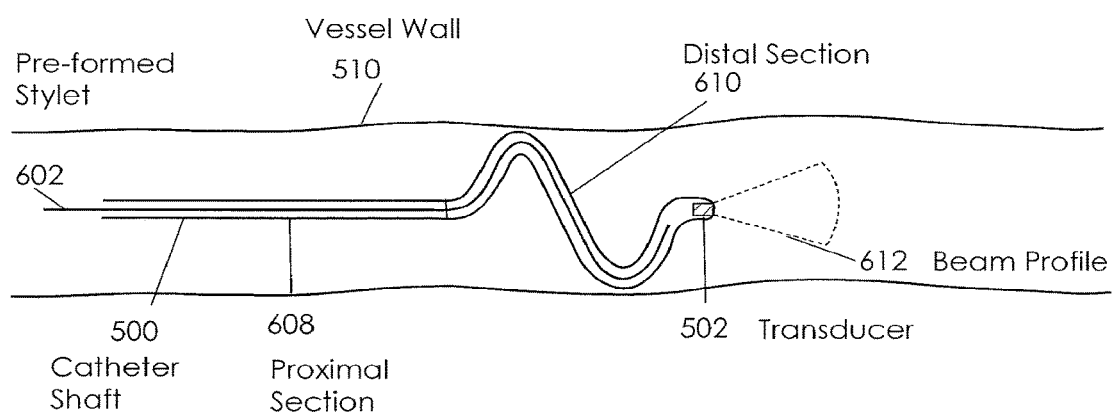

FIGS. 36A and 36B show another embodiment utilizing a pre-formed stylet to shape the catheter shaft itself without exiting a side port. In this embodiment, the catheter would have to accommodate a separate lumen for stylet delivery. FIG. 36A illustrates the pre-formed stylet prior to entering the distal section. FIG. 36B shows the shaped distal section with the stylet in place. FIGS. 36A and 36B include catheter shaft 500, proximal section 604, distal section 606, pre-formed stylet 602, transducer 502, beam profile 612 and vessel wall 510.

2.3.2.2 Sensor-Directed, Active

In the active sensor-directed embodiments of the stylet-based vascular access devices, placement of the device is facilitated by data received from the sensor(s) located on the catheter shaft or stylet tip during catheter advancement by actively manipulating the catheter shaft and subsequently the catheter tip. User interaction is required to advance the catheter according to the data received and displayed by the sensor(s), and the sensor(s) are again used to verify catheter tip placement at the desired target site. User interaction is also required to optimize the sensor(s) information received in these embodiments as this function cannot be accomplished by virtue of the catheter design alone.

Figure 40:
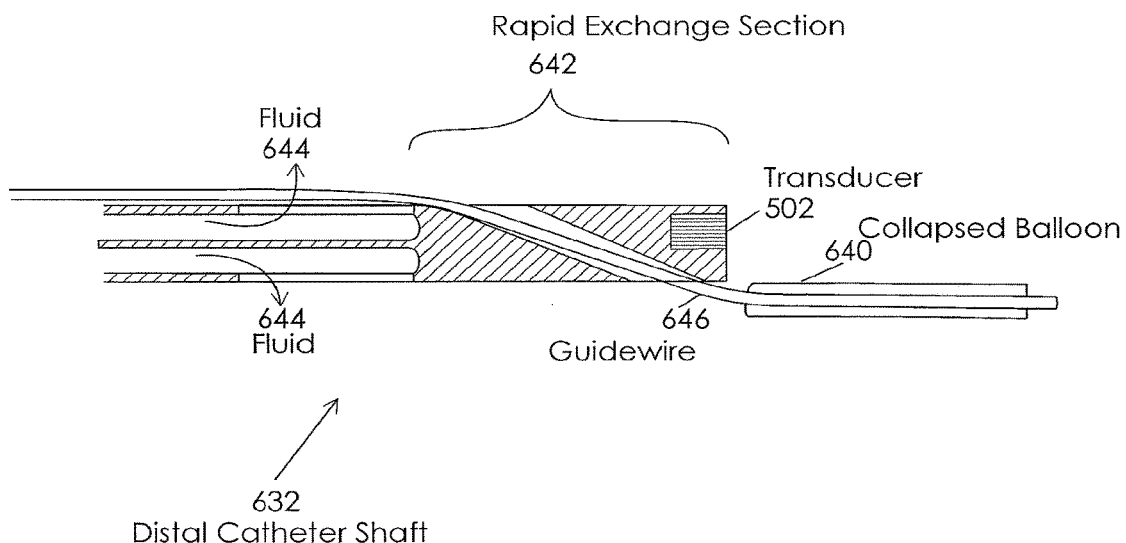
FIG. 40 shows an embodiment of a rapid exchange guidewire-based device, as previously described, in which the sensor(s) is again mounted on the catheter.

Coupled with a torque-able main/proximal catheter shaft 500, any of the FIG. 40 designs may be utilized for actively placing the sensor-directed catheter into the vessel, centrally with respect to blood flow.

2.3.3 Guidewire-Based Devices

Guidewire-based devices may be used independently of the catheter it is designed to work with; it may be used with other catheters, assuming the sizing needs, i.e.: the inner diameter of the catheter lumen accommodates the largest outer diameter of the guidewire, are met.

Embodiments of the guidewire-based inventive device include three basic forms. Some embodiments have tips directed mostly by fluid flow within the vasculature. Other embodiments are passively directed by the sensor(s) during guidewire/catheter advancement through the vasculature. Other embodiments require active manipulation of the guidewire/catheter tip to acquire and or optimize the data collected by the sensor(s).

2.3.3.1 Flow-Directed

As previously described in both the catheter and stylet-based devices, in the flow-directed embodiments of guidewire-based vascular access devices, placement of the device is 'automatic' in that minimal user interaction is required to position the catheter at the target site. The guidewire, and subsequently the catheter itself, is positioned 'automatically' by utilizing the blood flowing adjacent to and around it. The sensor is therefore used to verify guidewire/catheter tip placement at the desired target site as opposed to providing information during advancement to facilitate the advancement itself.

In these embodiments, blood flow is again utilized by flow-directable members mounted directly onto the guidewire. The guidewire is advanced into the vasculature, the flow-directable component is actuated, and the guidewire is allowed to 'float' to the desired target site. Once the target site is believed to have been reached, the user can verify position with the sensor(s). Then when the guidewire is no longer required, it can be removed leaving only the catheter shaft (with fluid delivery capability).

2.3.3.1.1 Guidewire-Mounted Sensor, Over the Wire

As described previously in Section 2.2, the catheter, once placed, may be able to deliver at least 2 different fluids through at least 2 dedicated lumens simultaneously. Further, the guidewire should be able to enter the vasculature alone and first, and then be completely removed. In an "over-the-wire" configuration, the guidewire may further be able to be removed entirely within the catheter shaft.

Figure 37:
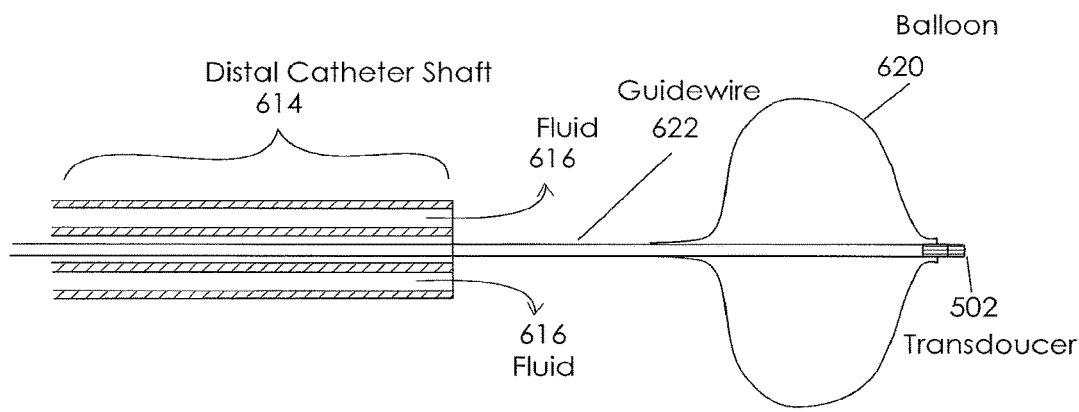
FIG. 37 shows an embodiment of an over-the-wire guidewire-based device in which the sensor(s) is also mounted on the guidewire.

FIG. 37 shows an embodiment of an over-the-wire guidewire-based device in which the sensor(s) is also mounted on the guidewire 622. FIG. 37 includes distal catheter shaft 614, fluid 616, guidewire 622, balloon 620 and transducer 502. In this embodiment, the guidewire 622 would be advanced into the vasculature, the balloon 620 would be inflated, the guidewire 622 would 'float' to the target site, the position would be verified with the attached sensor(s), the catheter (with fluid lumens) would be advanced to the target site, the balloon would be deflated, and the guidewire would be pulled out of the catheter.

Although this embodiment specifically illustrates a balloon-based flow-directed member, other such members as previously described that can collapse small enough to run through an internal catheter lumen could also be utilized.

2.3.3.1.2 Catheter-Mounted Sensor, Over the Wire

Figure 38A:
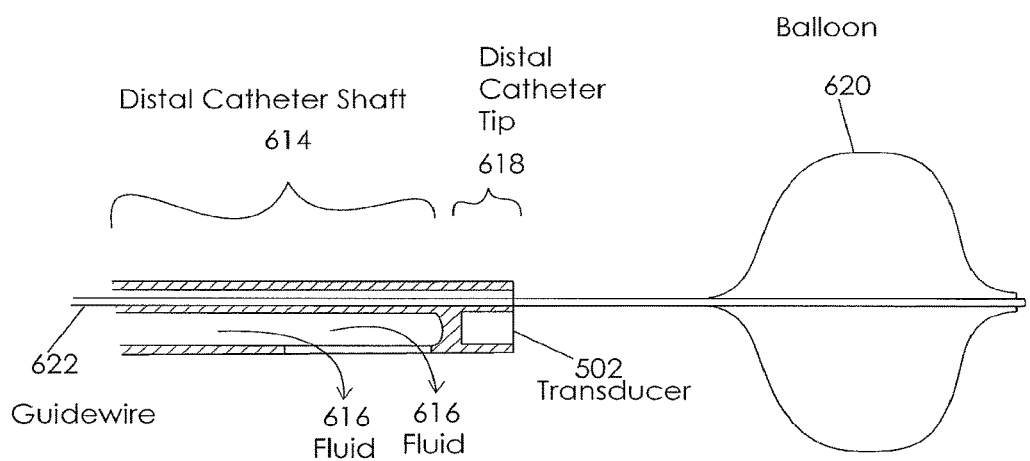
FIG. 38A shows an embodiment of an over-the-wire guidewire-based device in which the sensor(s) is mounted on the catheter.
Figure 38B:
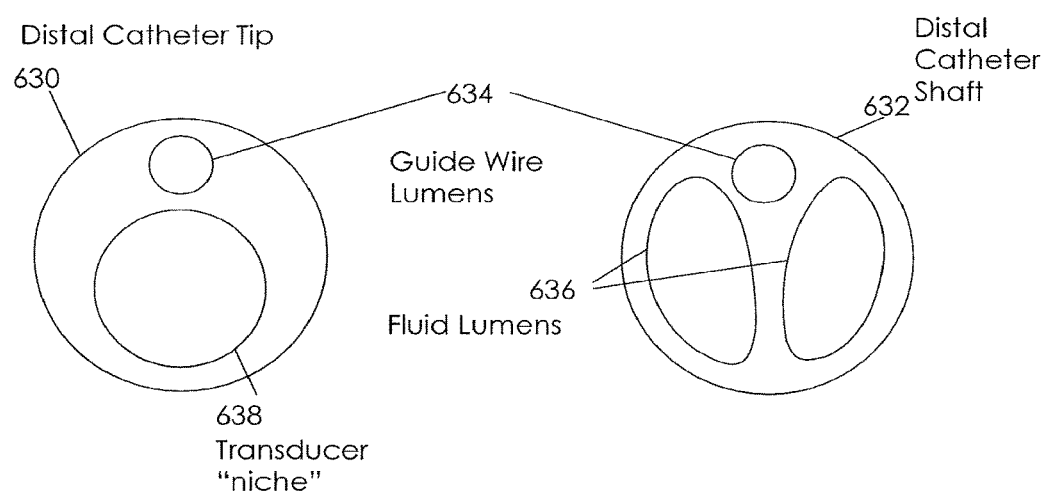
FIG. 38B shows an example of a possible cross-sectional configuration of the distal catheter shaft (right-side of Figure) vs. the very distal catheter tip (left side of Figure).

FIG. 38A shows an embodiment of an over-the-wire guidewire-based device in which the sensor(s) is mounted on the catheter. FIG. 38A includes distal catheter shaft 614, fluid 616, distal catheter tip 618, guidewire 622, balloon 620 and transducer 502. FIG. 38B shows an example of a possible cross-sectional configuration of the distal catheter shaft (right-side of Figure) vs. the very distal catheter tip (left side of Figure). FIG. 38B includes distal catheter tip 630, distal catheter shaft 632, fluid lumens 636, guidewire lumens 634 and transducer niche 638. In this embodiment, the wire would be advanced into the vasculature, the balloon would be inflated, the guidewire would 'float' to the apparent target site, the catheter (with fluid lumens and sensor(s)) would be advanced to the apparent target site, the position would be verified with the attached sensor(s), the balloon would be deflated, and the guidewire would be pulled out of the catheter.

Although this embodiment specifically illustrates a balloon-based flow-directed member, other such members as previously described that can collapse small enough to run through an internal catheter lumen could also be utilized.

2.3.3.1.3 Guidewire-Mounted Sensor, Rapid Exchange

Figure 39:
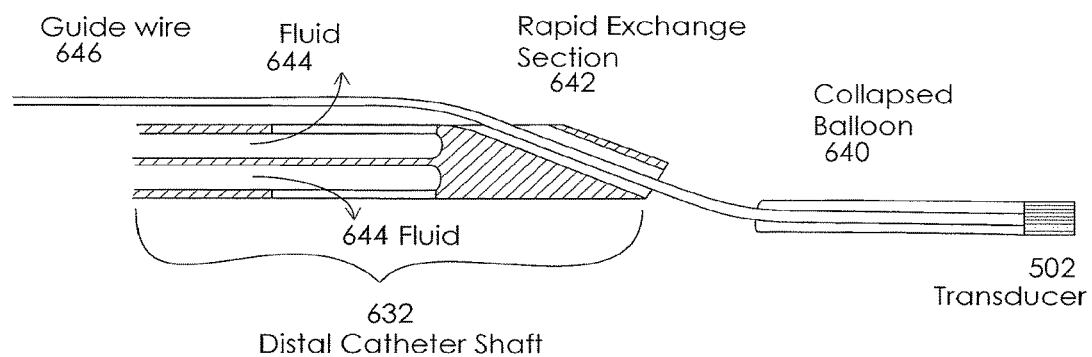
FIG. 39 shows an embodiment of a rapid exchange guidewire-based device in which the sensor(s) is again mounted on the guidewire.

FIG. 39 shows an embodiment of a rapid exchange guidewire-based device in which the sensor(s) is again mounted on the guidewire 646, however the guidewire would not reside completely within the entire catheter shaft 632 as in the over-the-wire devices; instead, the guidewire 646 could reside only within a small lumen located at the distal catheter tip. FIG. 39 includes distal catheter shaft 632, fluid 644, guidewire 646, collapsed balloon 640, rapid exchange section 642 and transducer 502. This may allow larger fluid delivery lumens since a lumen dedicated for the guidewire need not travel the entire catheter length. In this embodiment, the wire 646 would be advanced into the vasculature, the balloon would be inflated, the guidewire 646 would 'float' to the target site, the position would be verified with the attached sensor(s), the catheter (with fluid lumens) would be advanced to the target site, the balloon would be deflated, and the guidewire 646 would be pulled out of the catheter.

Although this embodiment specifically illustrates a balloon-based flow-directed member, other such members as previously described that can collapse small enough to run through a rapid exchange lumen could also be utilized.

2.3.3.1.4 Catheter-Mounted Sensor, Rapid Exchange

FIG. 40 shows an embodiment of a rapid exchange guidewire-based device, as previously described, in which the sensor(s) is again mounted on the catheter. FIG. 40 includes distal catheter shaft 632, fluid 644, guidewire 646, collapsed balloon 640, rapid exchange section 642 and transducer 502. This may allow larger fluid delivery lumens since a lumen dedicated for the guidewire 646 need not travel the entire catheter length. In this embodiment, the wire 646 would be advanced into the vasculature, the balloon would be inflated, the guidewire would 'float' to the apparent target site, the catheter (with fluid lumens and sensor) would be advanced to the apparent target site, the position would be verified with the attached sensor(s), the balloon would be deflated, and the guidewire would be pulled out of the catheter.

Alternatively, the distal catheter shaft where the rapid exchange lumen is located in FIG. 40 could be split in a longitudinal fashion so as to facilitate removal of the guidewire without needing the entire balloon assembly to retract through the rapid exchange lumen.

Figure 41:
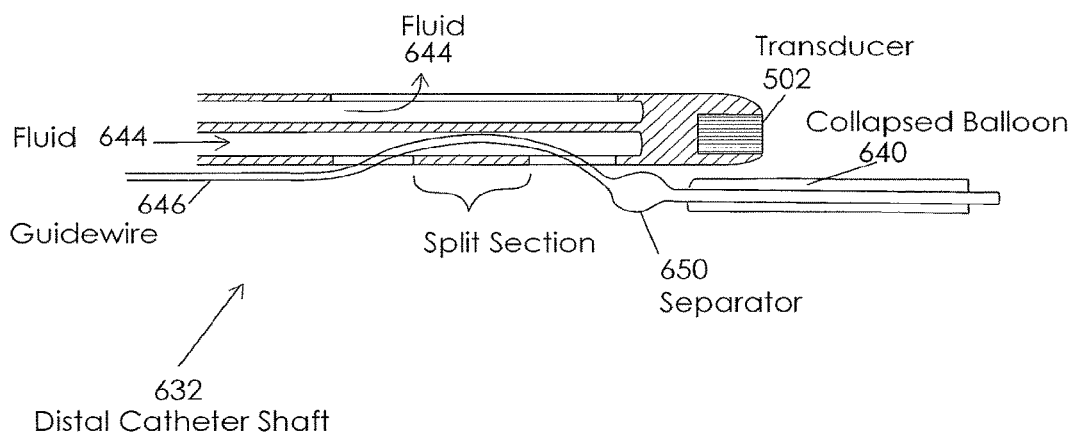
FIG. 41 shows another embodiment of FIG. 40 in which one of the distal fluid lumen ports could have a section that is split in a longitudinal fashion as opposed to being completely open.

FIG. 41 shows another embodiment of FIG. 40 in which one of the distal fluid lumen ports could have a section that is split in a longitudinal fashion as opposed to being completely open. FIG. 41 includes distal catheter shaft 632, fluid 644, guidewire 646, collapsed balloon 640, separation 650 and transducer 502. The distal guidewire 646 is retracted through the distal section of the split port until the separator 650 feature reaches the split section. The separator 650 then spreads and separates the entire port length such that the entire guidewire 646 is freed from the lumen and can be removed separately from the catheter shaft 632.

Although these embodiments specifically illustrate balloon-based flow-directed members, other such members as previously described that can collapse small enough to run through a rapid exchange lumen could also be utilized.

2.3.3.2 Sensor-Directed (Passive)

In the passive sensor-directed embodiments of the guidewire-based vascular access devices, placement of the device is facilitated by data received passively from the sensor(s) located on the guidewire or catheter shaft during catheter advancement. User interaction is required to advance the catheter according to the data received and displayed by the sensor(s), and the sensor(s) are again used to verify catheter tip placement at the desired target site. However, no user interaction is required to optimize the sensor(s) information received in these embodiments: this function is passively accomplished by virtue of the guidewire/catheter design.

Any of the embodiments described in FIGS. 37, 38A, 38B, 39, 40 and 41 may be utilized to facilitate a passive sensor-directed catheter positioning technique.

2.3.3.3 Sensor-Directed (Active)

In the active sensor-directed embodiments of the catheter-based vascular access devices, placement of the device is facilitated by data received from the sensor(s) located on the catheter shaft during catheter advancement by actively manipulating the catheter shaft and subsequently the catheter tip. User interaction may be needed to advance the catheter according to the data received and displayed by the sensor(s), and the sensor(s) are again used to verify catheter tip placement at the desired target site. User interaction may be utilized to optimize the sensor(s) information received in these embodiments.

Figure 42:
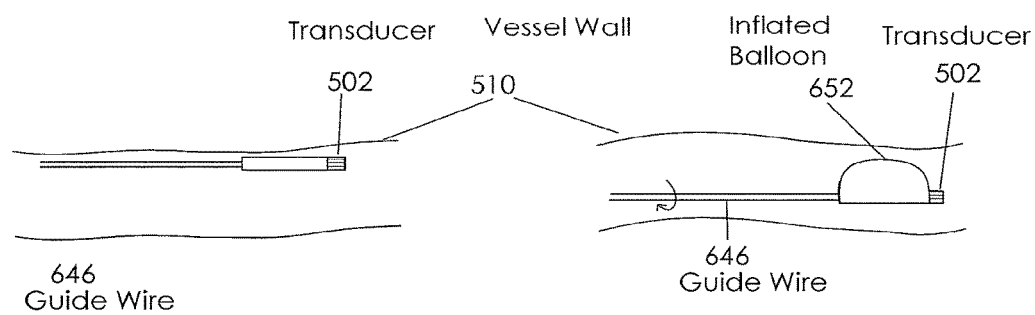
FIG. 42 shows an embodiment of a sensor-directed guidewire based device advanced to the target site via active manipulation of the guidewire during advancement by the user.

FIG. 42 shows an embodiment of a sensor-directed guidewire based device advanced to the target site via active manipulation of the guidewire 646 during advancement by the user. FIG. 42 includes guidewire 646, vessel wall 510, inflated balloon 652 and transducer 502. Assuming a torquable guidewire shaft is available, a radially-asymmetric balloon could be mounted on the distal guidewire end. Once inflated, the guidewire 646 could be actively 'steered' through the vasculature by using the off-set created by the balloon 652. The left side of the figure shows an uninflated balloon; the right side shows an inflated balloon 652.

Many of the previously described embodiments may also be utilized to facilitate an active sensor-directed catheter positioning technique.

3.0 Device for Securement of Proximal End of Access Device

Once the vascular access device has been placed and its distal tip position confirmed, a means by which to secure the proximal catheter shaft is needed. This proximal securement device may hold the catheter hub in place and prevent migration with respect to the skin incision, and may manage the connections, whether electrical, fluid or actuation/inflation in nature.

A securement device is affixed to the patient's skin at a suitable location near the puncture site using a suitable biocompatible pressure sensitive adhesive. The securement device has a mounting surface adapted to engage with the device hub described herein. The device hub may be affixed to the mounting surface using any suitable mechanical attachment, e.g. snaps, friction lock or keyed surfaces. The device hub and/or the securement device may include suitable RFID tags as described in section 7.0.

Various details of the design for a securement device may be appreciated through reference to U.S. Pat. Nos. 7,153,291 and 7,223,256, incorporated herein by reference in their entirety.

Figure 43:
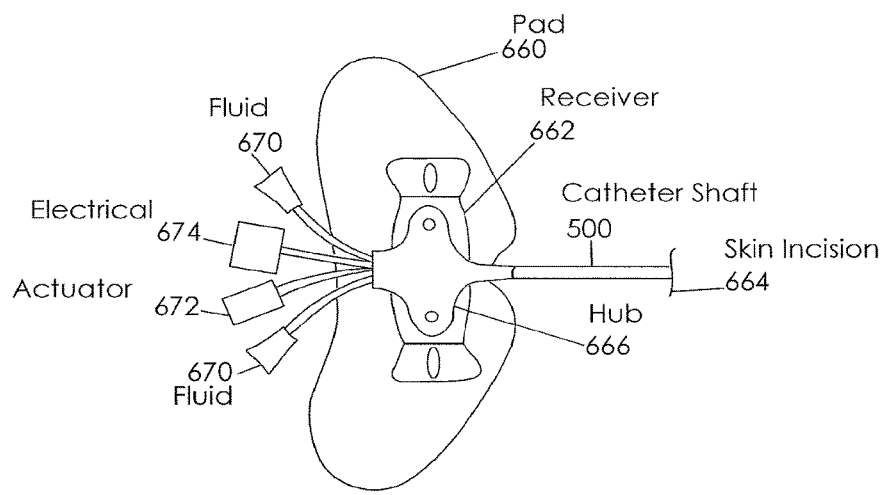
FIG. 43 shows an embodiment of a securement device that attaches to the proximal catheter shaft thereby minimizing catheter tip migration from the target site.

FIG. 43 shows an embodiment of a securement device that attaches to the proximal catheter shaft 500 thereby minimizing catheter tip migration from the target site. FIG. 43 includes pad 660, receiver 662, catheter shaft 500, hub 666 and skin incision 664 as well as connections such as fluid 670, electrical 674 and actuator 672. To facilitate ease of use, connections may remain on the catheter hub 666 itself, i.e., as 'pigtails', such as: electrical 674 (to make the transducer and ECG connections), fluid 670 (to a luer fitting to facilitate inflation/deflation and fluid delivery), or mechanical 672 (to facilitate some sort of distal component actuation or manipulation).

Figure 44A:
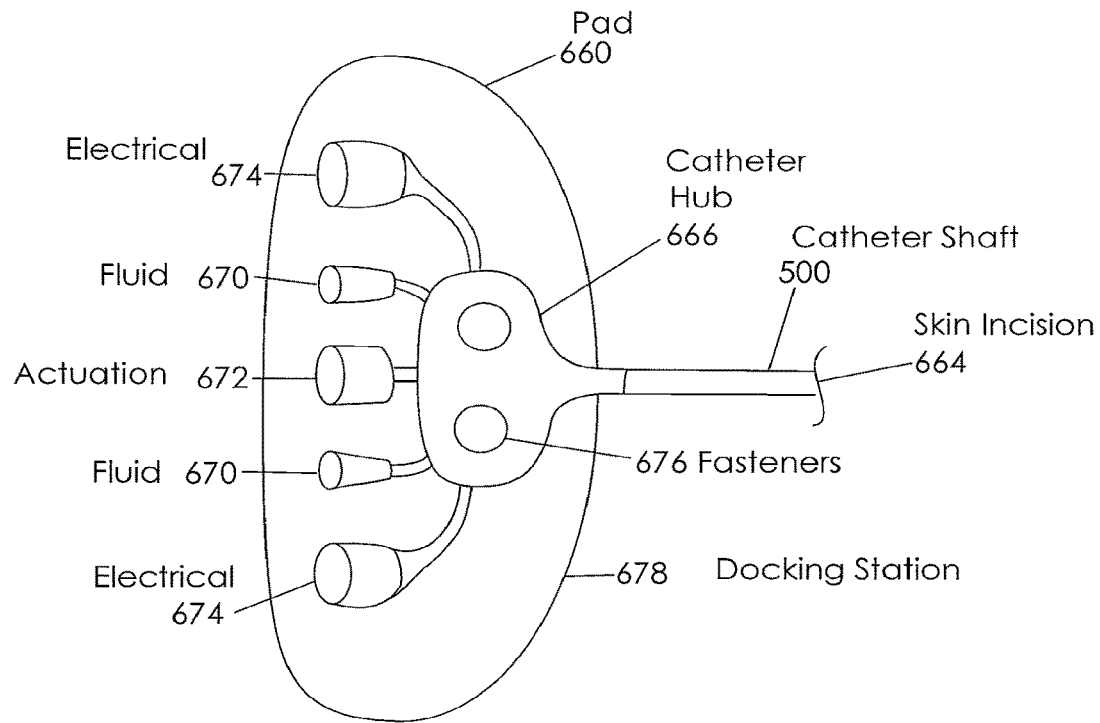
FIGS. 44A and 44B show top and end views, respectively, of an alternative embodiment of a securement device.
Figure 44B:
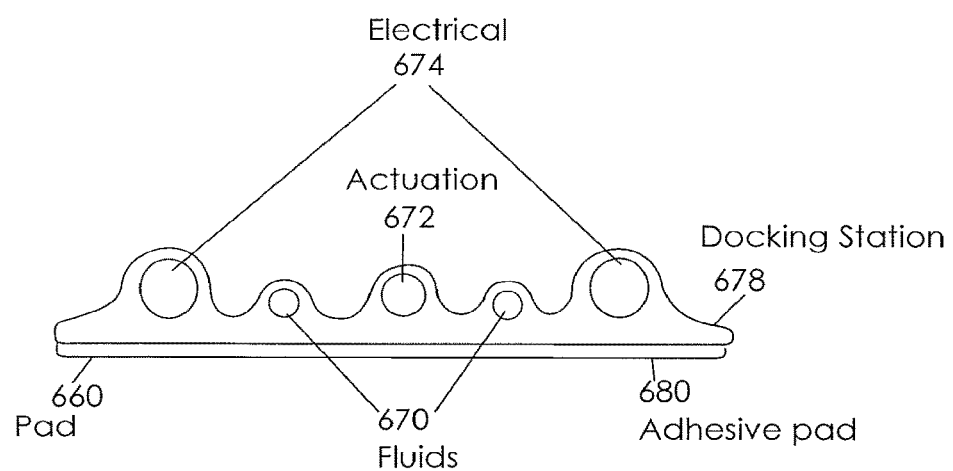

FIGS. 44A and 44B show top and end views, respectively, of an alternative embodiment of a securement device. FIG. 44A includes pad 660, receiver 662, catheter shaft 500, catheter hub 666, fasteners 676, docketing station 678 and skin incision 664 as well as connections such as fluid 670, electrical 674 and actuation 672. FIG. 44B includes adhesive epad 680, docket station 678, pad 660 and connections such as fluid 670, electrical 674 and actuation 672. In this embodiment, a smart catheter hub 666 is positioned on the proximal end of the vascular access device. The smart hub 666 is designed such that the placement of the hub 666 into the receiver would facilitate the necessary connections, i.e.: transducer, electrical activity, fluid delivery . . . etc. This could be accomplished by any number of methods, for example, the hub could be snapped in place, held with Velcro or engaged with a keyed mechanism. The smart catheter hub 666 includes all of the connections for the added functionalities used in the vascular access device. Once connected, the smart catheter hub 666 establishes the appropriate conductivity between the vascular access device and the guiding system. In the illustrated embodiment, the smart hub makes 666 connections for two electrical 674, two fluid 670 and one actuation 672 interfaces.

4.0 Device and Method for Improving Workflow Efficiency of Bedside Patient Care

An aspect of the invention describes RFID and or barcode based labeling and identification of devices and players in the bedside care workflow. The invention also describes a method for making use of such devices for workflow optimization. In particular the invention relates to using two or more focused energy transmitters and receivers in order to detect each others presence in each others field of view.

Other aspects of the following embodiments share some or all of the following characteristics:

The use of RFID concepts and RFID based devices (tags, readers, synchronization and optimization) in medical care workflow.

Tagging devices using RFID, barcodes or other suitable machine readable indicators as well as using such tags for players in the medical care workflow. Players include any of a variety of heath care providers that interact with the patient and/or the device, are responsible for dispensing the device or ensuring the device is or remains properly placed during use.

Optimize medical workflow by maintaining and integrating records of devices and activities, by programming activities on a "just-in-time" basis as needed and as resources are available.

These and other aspects of the various embodiments of the invention will be appreciated in the description that follows.

The VasoNova PICC system may provide for workflow tracking, which is important for optimizing operational efficiency. More PICCs can be placed in a given time period by identifying and avoiding significant down time. To help in analyzing workflow and time management during the PICC placement and confirmation process, the VasoNova PICC system enables tracking by recording the time at various key steps during the process.

A simple but comprehensive tracking system is setup with three key time entries and various work types that are identified and entered into the system by the operator.

In one embodiment, the three key time entries are:
Receive consult request
Start 'work' on case
Stop 'work' on case
Non-limiting examples of primary work types are:
Gather patient data (check history, allergies, labs, etc.)
Transportation to case (cart/supplies) and patient consent
Sterile setup
Venipuncture Catheter insertion/placement
Verification of tip position
Secure catheter
Order/wait for x-ray
Confirm catheter ready for use Other work types can be added as desired and work types can be combined. For example sterile setup, venipuncture, catheter insertion, verification, and securing catheter may be grouped together as a single work type called 'procedure'.

Data entry for tracking can be done by means of pressing buttons located on a small mobile device that is to be worn as one carries a pedometer or digital pager. The device interfaces with the VasoNova handheld unit and it may be connected to the handheld by a cord or it may have a wireless connection. Alternatively, scanning bar codes or electromagnetic strips for example could accomplish the data entry.

Figure 45:
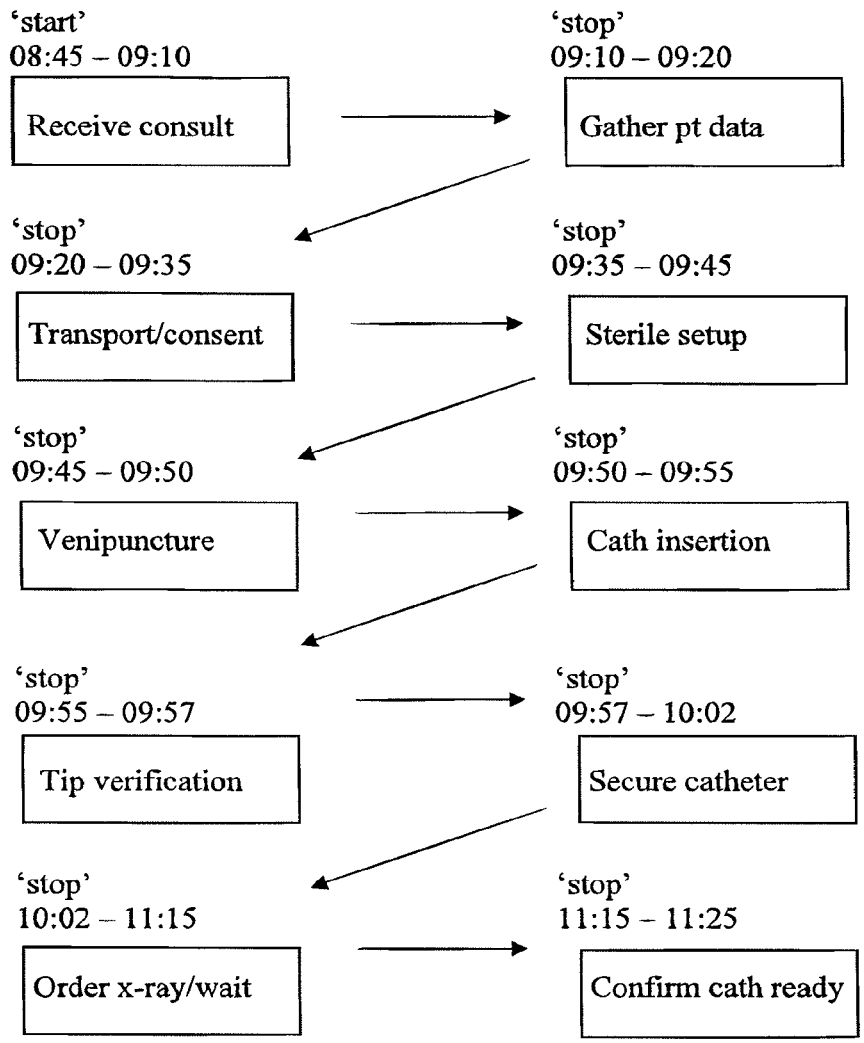
FIG. 45 shows an example of workflow tracking on a Vasonova handheld GUI.

In the case of a data entry device with buttons, specific tasks are tracked by pushing a 'start' button followed by 'task' button that is highlighted by using 'up' and 'down' buttons that are easily located on the device by their position and confirmed on the GUI of the handheld. Once the task is completed, the 'stop' button is pushed, which then records the stop time for that task, which is simultaneously recorded as the start time for the next task in the process as illustrated in FIG. 45.

The VasoNova handheld GUI has a menu feature that indicates which workflow interval is being tracked and the operator can modify or change the present task by using the 'up' and 'down' buttons on the data entry device as shown in FIG. 46. FIG. 46 includes handheld GUI 690, start button 692, stop button 694, up button 696, enter button 698 and down button 700.

The buttons have different shapes and sizes that are easily memorized by the operator so that they can be located and pressed through a sterile gown if the device is clipped to the operator's belt for example The GUI will display the tasks and with the present task highlighted as illustrated in FIG. 47. The task can be changed at any time by pressing the up/down buttons on the data entry device.

Figure 48:
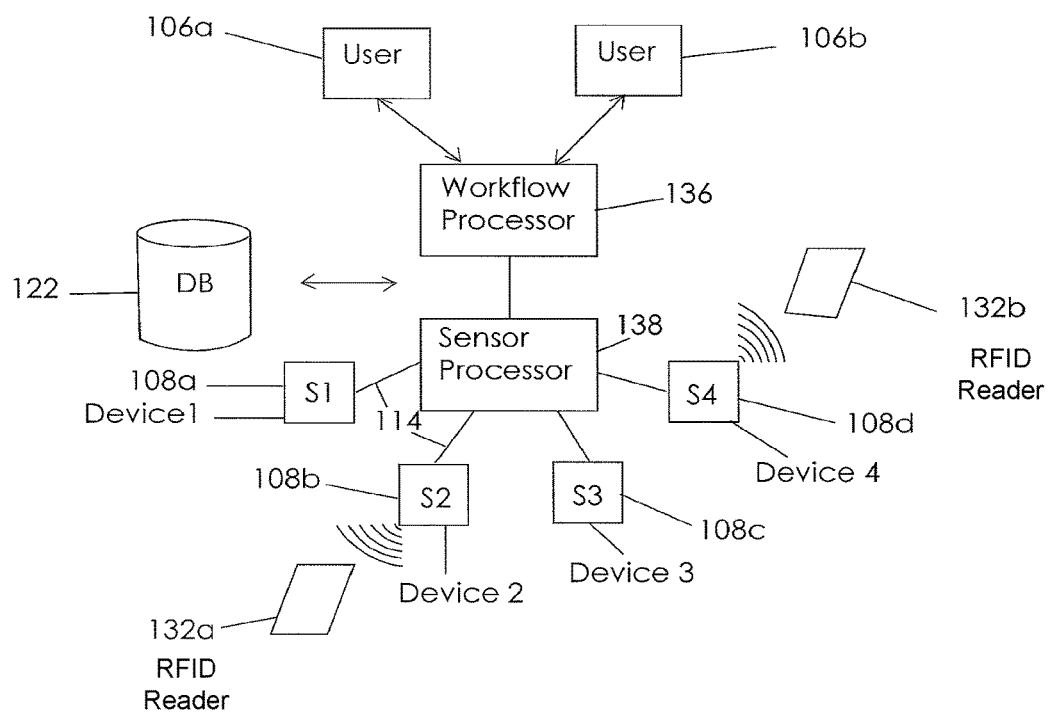
FIG. 48 shows the players in a medical workflow.

FIG. 48 shows the players in a medical workflow. According to an embodiment of the invention, users e.g., hospital medical personnel or players wear RFID tags or other machine detectable labels. FIG. 48 includes users 106a and 106b, devices 108a, 108b, 108c and 108d, database 122, RFID reader 132a and 132b, workflow processor 136 and sensor processor 138. Players may have their ID integrated provided as a separate article of may be integrated into an existing article used by the player, e.g., on their pager, phone, PDA, nametag, and the like. Devices (S) have RFID tags or barcodes on packaging labels. Patients have RFID tags associated with them and on their documents. A Sensor Processor is integrated with the VasoNova Guiding System (e.g., RFID tag reader). An individual Workflow Processor 136 is integrated with the VasoNova Guiding System. A centralized Optimization Processor is residing on the server and makes use of the hospital database. RFID tags can be placed on other pieces of equipment or with other players of the bedside care system: radiologists, X-ray systems, etc. The VasoNova RFID reader 132a/132b, the Sensor Processor 138 and the Workflow Processor 136 integrated in the VasoNova Guiding System allow for coordination of all players and for workflow optimization.

While RFID tags are used in the above description, the invention is not limited only to the use of RFID tags but may include the use of any suitable machine readable or detectable device that may be configured for use in tracking the progress of a medical procedure.

The U.S. Pat. No. 5,311,871 entitled "Smart Needle" by Paul Yock is also incorporated by reference.

U.S. Pat. No. 6,860,422 "Method and Apparatus for Tracking Documents in a Workflow" by—Hull et al. is also incorporated herein by reference in its entirety.

Further, the following patents and published application are incorporated herein by reference in their entirety:

U.S. Pat. No. 5,546,949
U.S. Pat. No. 4,706,681
U.S. Pat. No. 5,515,853
U.S. Pat. No. 5,830,145
U.S. Pat. No. 6,259,941
U.S. Pat. No. 6,298,261
U.S. Pat. No. 6,958,677
U.S. Pat. No. 7,054,228
U.S. Published Patent Application 20030036696.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An endovascular device, comprising:
    a torquable elongate body sized for insertion into the vasculature, the torquable elongate body having a proximal end and a distal end terminating in a distal tip;
    a sensor on the distal end of the torquable elongate body, the sensor configured to measure a characteristic of blood flow within a blood vessel;
    a structure on or in the torquable elongate body that is configured to radially expand to move the distal tip of the torquable elongate body away from a peripheral inner surface of the blood vessel while maintaining blood flow within the blood vessel when the structure is radially expanded within the blood vessel; and
    a signal processor connected to the sensor and the structure, the signal processor being configured to:
        receive the measured characteristic of blood flow within the blood vessel,
        determine that the sensor is within a minimum lateral distance from the peripheral inner surface when the peripheral inner surface is peripheral of the sensor based on the measured characteristic of blood flow within the blood vessel, and
        cause active manipulation of the structure to move the distal tip of the torquable elongate body laterally away from the peripheral inner surface of the blood vessel to the minimum lateral distance to avoid measuring the characteristic of blood flow at a periphery of the blood vessel.

2. The device of claim 1, wherein the torquable elongate body further comprises a distal segment that is flexible and made of a polymer, and the polymer being reinforced to increase tensile strength.

3. The device of claim 1, wherein the structure is a star shaped balloon on or about the torquable elongate body.

4. The device of claim 1, wherein the structure is a deployable circular braid.

5. The device of claim 1, wherein the structure is a deployable balloon.

6. The device of claim 1, wherein the structure comprises strips cut in the torquable elongate body that are radially expanded.

7. The device of claim 1, wherein the structure comprises a deployable basket.

8. The device of claim 1, wherein the signal processor is configured to cause active manipulation of the torquable elongate body within the blood vessel to align the sensor with the blood flow.

9. The device of claim 1, wherein the structure comprises a tether component attached to the torquable elongate body.

10. The device of claim 1, wherein the sensor is an ultrasound transducer.

11. The device of claim 10, wherein the ultrasound transducer is a pulsed wave Doppler or continuous wave Doppler sensor.

12. The device of claim 2, wherein the polymer is reinforced with a coil within the polymer of the torquable elongate body.

13. The device of claim 1, wherein the distal end of the torquable elongate body is closed and defines side ports for fluid delivery.

14. The device of claim 1, wherein the sensor is distal to the structure on or in the torquable elongate body.

15. The device of claim 1, wherein the sensor is within the structure on or in the torquable elongate body.

16. The device of claim 1, wherein proximal end of the torquable elongate body is made of a stiffer material than the distal end of the torquable elongate body.

17. The device of claim 1, wherein the structure is radially offset about the torquable elongate body.

18. The device of claim 1, wherein the measured characteristic of blood flow within the blood vessel comprises velocity of blood flow within the blood vessel.

19. The device of claim 18, wherein the measured characteristic of blood flow within the blood vessel further comprises pulsatility pattern of blood flow within the blood vessel.

* * * * *